United States Patent
Hogan et al.

(10) Patent No.: US 10,946,047 B2
(45) Date of Patent: Mar. 16, 2021

(54) EXTRACELLULAR VESICLES WITH ENHANCED POTENCY

(71) Applicant: United Therapeutics Corporation, Silver Spring, MD (US)

(72) Inventors: Sarah Hogan, Raleigh, NC (US); Roger Marquez Ilagan, Durham, NC (US); Maria Pia Rodriguez, Durham, NC (US); Carolina Medrano, Durham, NC (US); John Cheadle, Durham, NC (US)

(73) Assignee: United Therapeutics Corporation, Silver Spring, MD (US)

( * ) Notice: Subject to any disclaimer, the term of this patent is extended or adjusted under 35 U.S.C. 154(b) by 13 days.

(21) Appl. No.: 15/967,714

(22) Filed: May 1, 2018

(65) Prior Publication Data

US 2018/0296606 A1   Oct. 18, 2018

Related U.S. Application Data

(63) Continuation-in-part of application No. 15/625,961, filed on Jun. 16, 2017, now abandoned.

(60) Provisional application No. 62/351,627, filed on Jun. 17, 2016.

(51) Int. Cl.

| C12N 9/14 | (2006.01) |
|---|---|
| A61K 35/28 | (2015.01) |
| A61P 9/12 | (2006.01) |
| C12N 9/12 | (2006.01) |
| C12N 5/0775 | (2010.01) |
| C07K 14/47 | (2006.01) |
| A61K 31/519 | (2006.01) |
| C12N 5/071 | (2010.01) |
| C12N 5/077 | (2010.01) |
| A61K 48/00 | (2006.01) |

(52) U.S. Cl.
CPC ............ *A61K 35/28* (2013.01); *A61K 31/519* (2013.01); *A61P 9/12* (2018.01); *C07K 14/47* (2013.01); *C12N 5/0662* (2013.01); *C12N 5/0669* (2013.01); *C12N 5/0691* (2013.01); *C12N 9/1205* (2013.01); *C12N 9/14* (2013.01); *C12Y 207/0104* (2013.01); *C12Y 306/01003* (2013.01); *A61K 48/00* (2013.01); *C12N 2310/141* (2013.01); *C12N 2502/1394* (2013.01)

(58) Field of Classification Search
CPC .......... A61K 35/28; A61K 35/45; C12N 9/14; C12N 15/113
See application file for complete search history.

(56) References Cited

FOREIGN PATENT DOCUMENTS

| WO | WO 2012/108842 A1 | 8/2012 |
|---|---|---|
| WO | WO 2012/125471 A1 | 9/2012 |
| WO | WO 2014/022373 A1 | 2/2014 |
| WO | WO 2015/016761 A2 | 2/2015 |
| WO | WO 2015/179227 A1 | 11/2015 |

OTHER PUBLICATIONS

"Second European Consensus Document on Chronic Critical Leg Ischemia", Circulation, Nov. 1991, 84(4 Suppl.):IV-1-IV-26.
Boeing et al,. "Single-step isolation of extracellular vesicles by size-exclusion chromatography," Journal of Extracellular Vesicles, Sep. 8, 2014, 3:1:23430.
D'Alonzo et al., "Survival in Patients with Primary Pulmonary Hypertension," Ann. Intern. Med., Sep. 1, 1991, 115(5):343-349.
DiMauro et al., "Mitochondrial DNA Mutations in Human Disease," Am. J. Med. Genet., 2001, 106:18-26.
Dormandy et al., "Chronic Critical Limb Ischemia," J. Vasc. Surg. 2000, 31:S168-S175.
Eneroth et al., "Amputation for occlusive arterial disease, A prospective multicentre study of 177 amputees," Int. Orthop. (SICOT), 1992, 16:383-387.
Humbert et al., "Cellular and Molecular Pathobiology of Pulmonary Arterial Hypertension," J. Am. Coll. Cardiol., 2004, 43(12:SupplS):13S-24S.
Keily et al., "Pulmonary hypertension: diagnosis and management," BMJ, 2013, 346:f2028, 1-12.
Lee et al., "Exosonnes Mediate the Cytoprotective Action of Mesenchymal Stromal Cells on Hypoxia-Induced Pulmonary Hypertension," Circulation, Nov. 27, 2012 (Oct. 31, 2012), 126(22):2601-2611.
Leonard et al., "Mitochondrial respiratory chain disorders I : mitochondrial DNA defects," Lancet, 2000, 355:299-304.
Rissanen et al., "Gene therapy for therapeutic angiogenesis in critically ischaemic lower limb—on the way to the clinic," European Journal of Clinical Investigation, 2001, 31:651-666.
Thery et al., "Isolation and Characterization of Exosomes from Cell Culture Supernatants and Biological Fluids," Current Protocols in Cell Biol., 2006, 3.22.1-3.22.29.
Tyrrell et al., "Critical leg ischaemia: an appraisal of clinical definitions," Br. J. Surg., February 1003, 80:177-180.
Zhou et al., "Collection, storage, preservation, and normalization of human urinary exosomes for biomarker discovery," Kidney International, 2006, 69:1471-1476.

*Primary Examiner* — Karen Cochrane Carlson
(74) *Attorney, Agent, or Firm* — Foley & Lardner LLP

(57) ABSTRACT

Provided are methods for isolating potent extracellular vesicle or exosome populations from mesenchymal stromal cells, and the use of the isolated extracellular vesicles or exosomes in treating vasculopathy, including pulmonary hypertension, bronchopulmonary dysplasia, and disease and conditions associated with mitochondrial dysfunction.

20 Claims, 61 Drawing Sheets

| Pathway | Proteins |
|---|---|
| Glycolysis | AGI, ALDO, TPI, GAPDH, ENO, PGAM, PK |
| TCA Cycle | OGDH |
| Electron Transport Chain | ETFA, ATPase |

FIG. 4

| Pathway | Genes |
|---|---|
| Glycolysis | ALDOA, ENO3, GPI, HK2,3, PFK, PGM, PK |
| TCA Cycle | MDH2, OGDH, PC, PDHA1, PDHB, SDHA, SDHC, SUCLG2 |
| Electron Transport Chain | Complex I (NDUFC2, NDUFB1, NDUFS5, NDUFA8, NDUFA9, NDUFS2); Complex II (SDHA, SDHC); Complex III (UQCRH1); Complex IV (Cox 6c1, Cox10); Complex V (39 ATPase genes enriched) |

Mouse Histology:
* 7 days 75% O2
* 7 days normoxia

Normoxia     HYRX (75 O$_2$%)

FIG. 18
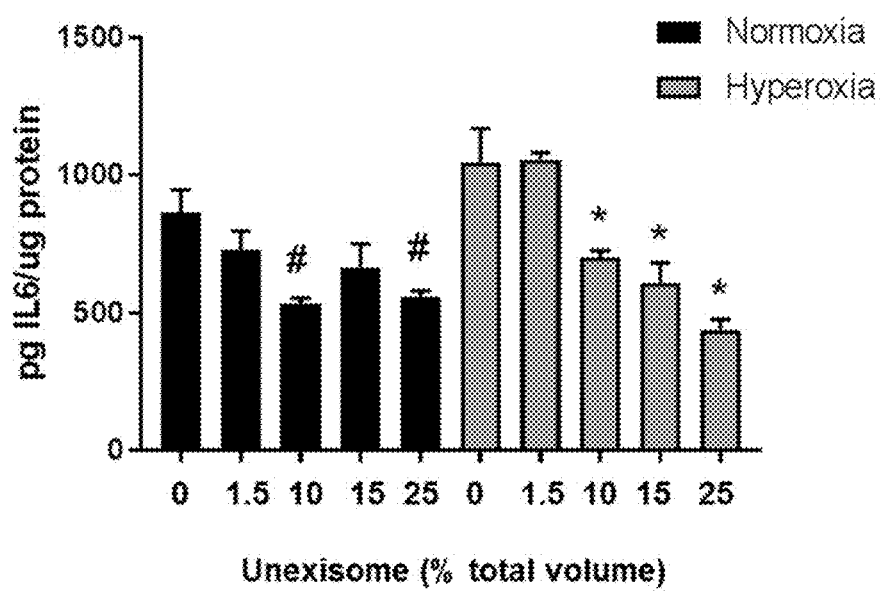
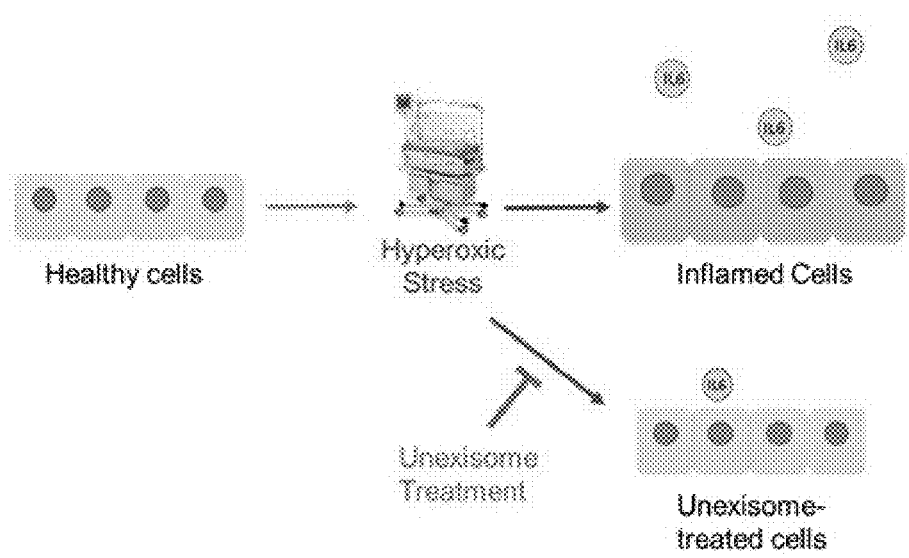

FIG. 19
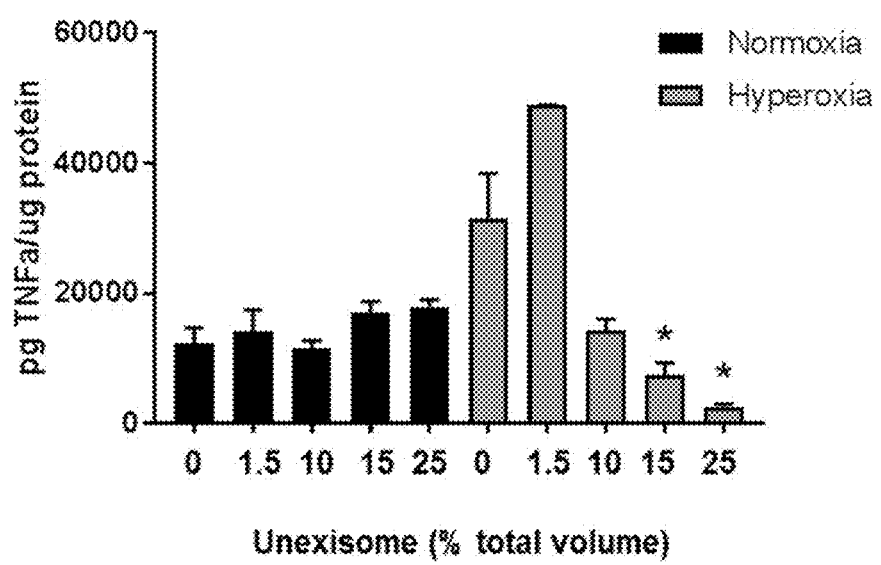
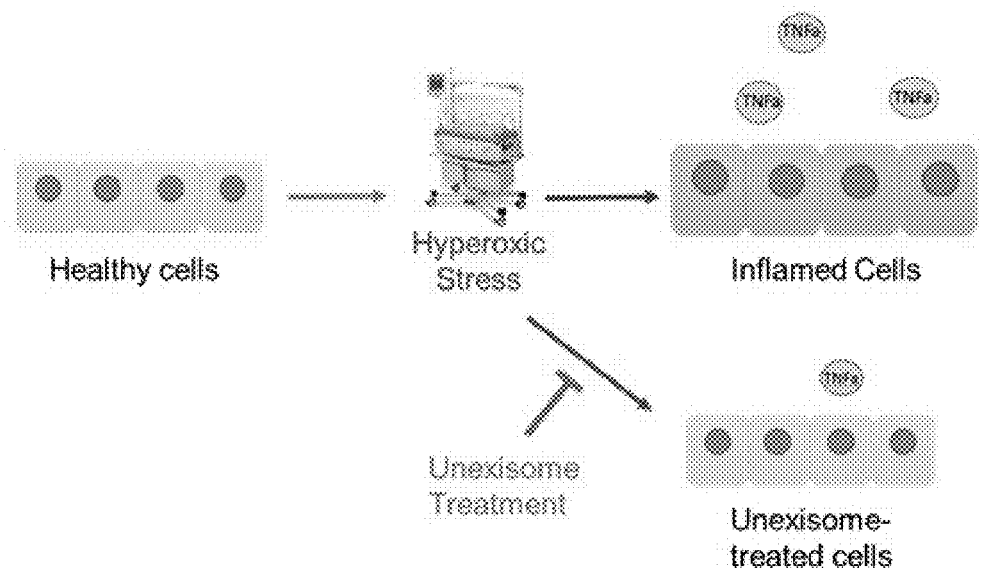

FIG. 20
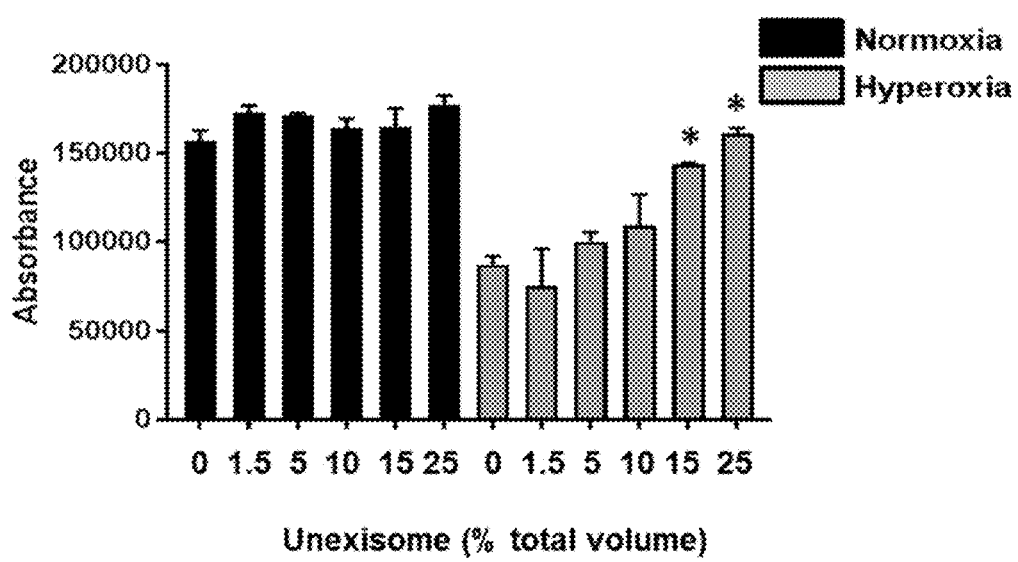
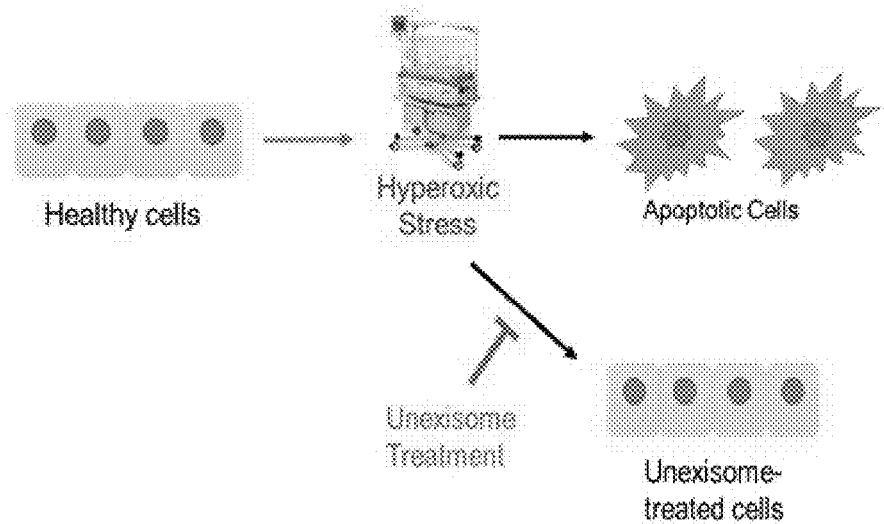

FIG. 21
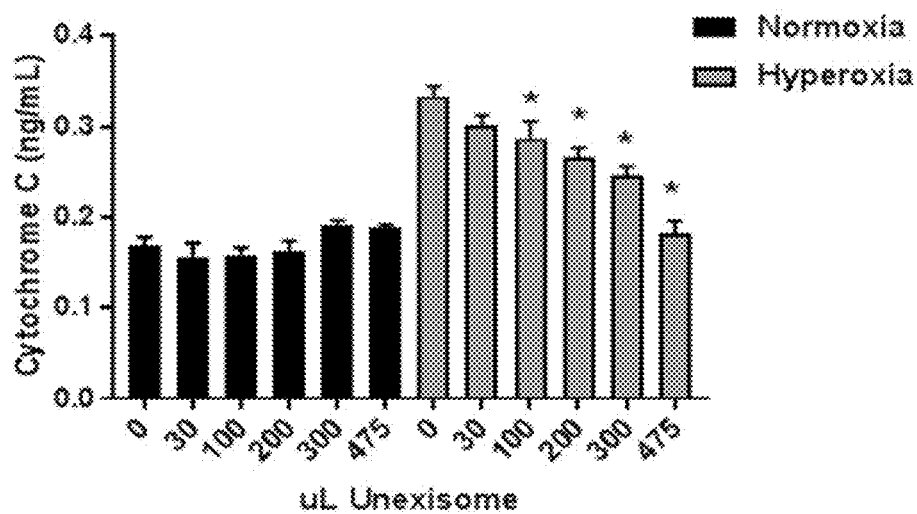
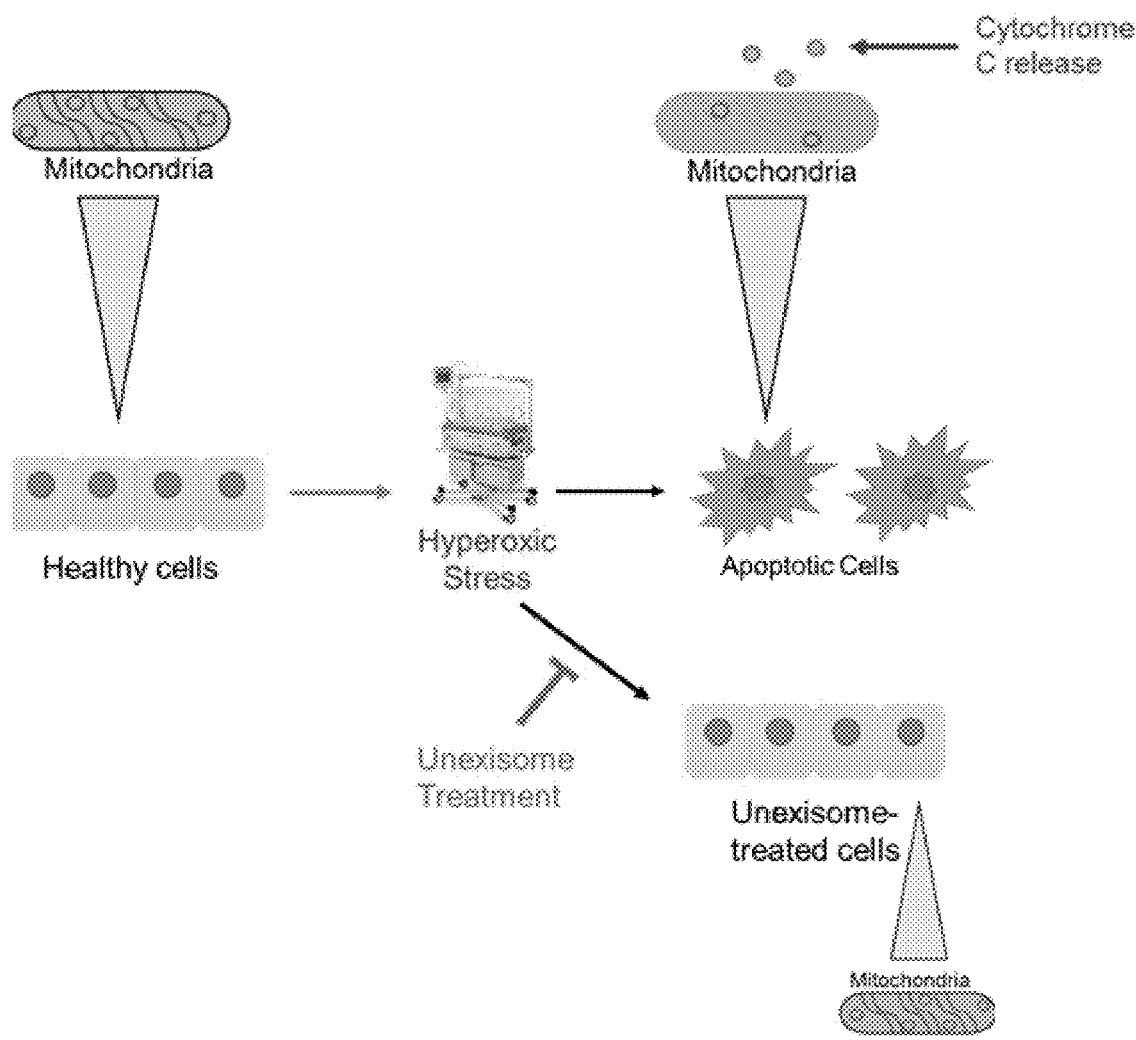

FIG. 29
Ultracentrifuged pellet
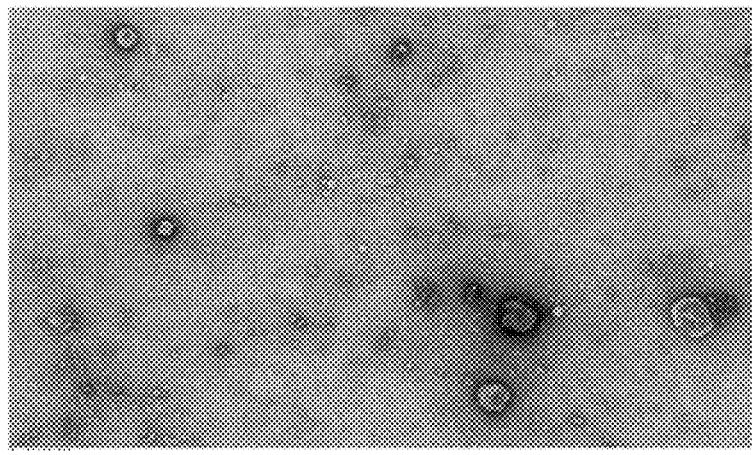
Size Exclusion Chromatography : COM001
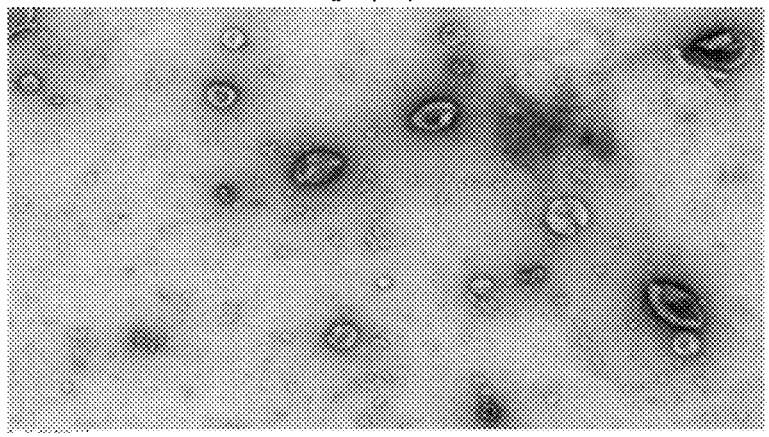
Size Exclusion Chromatography: COM002
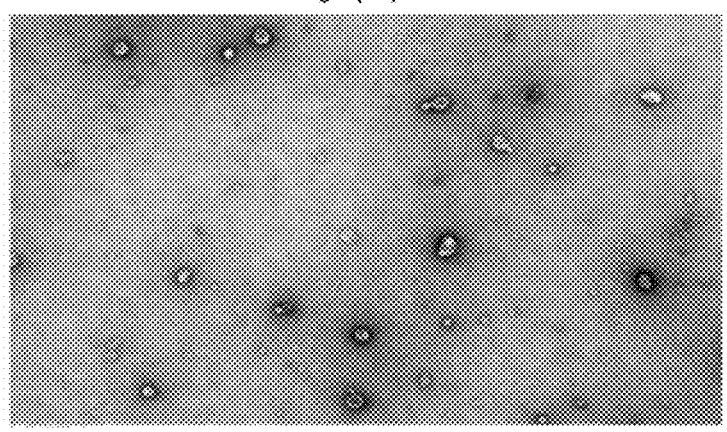

FIG. 31A
A) Fibronectin 263kDa
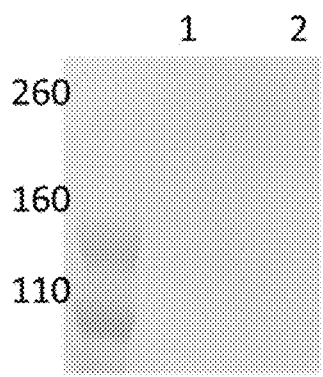
1. EXSM-20170330A-SRB001-COM001
2. EXSM-20170330A-SRB001-COM002
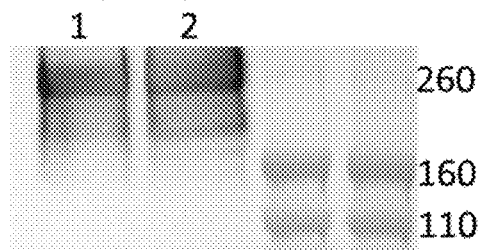
1. ZenBio: human placental MSC exosomes
2. ZenBio: human peradipocyte exosomes
FIG. 31B
B)
Ponceau stain
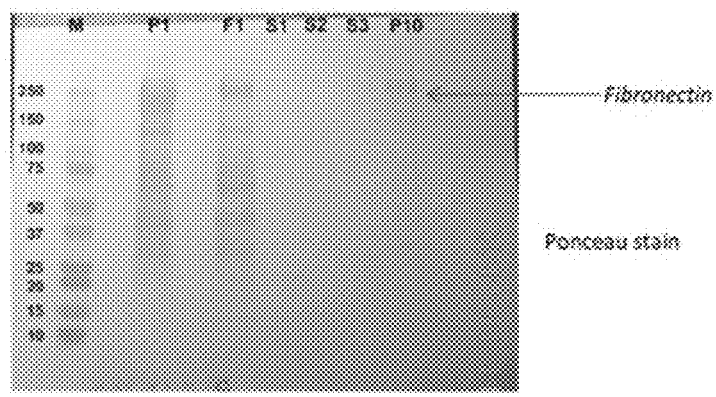
M: Marker
P1: Ultracentrifuged pellet
F1: 50X concentrated condition media
S1: Size Exclusion Chromatography: COM 001
S2: Size Exclusion Chromatography: COM 002

FIG. 41A
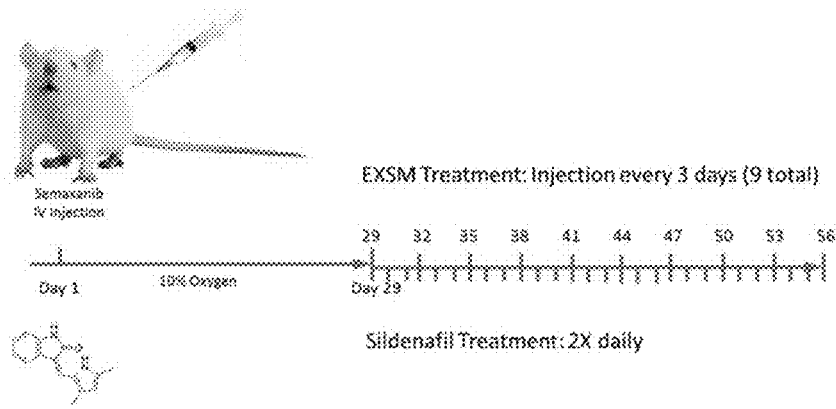
FIG. 41B
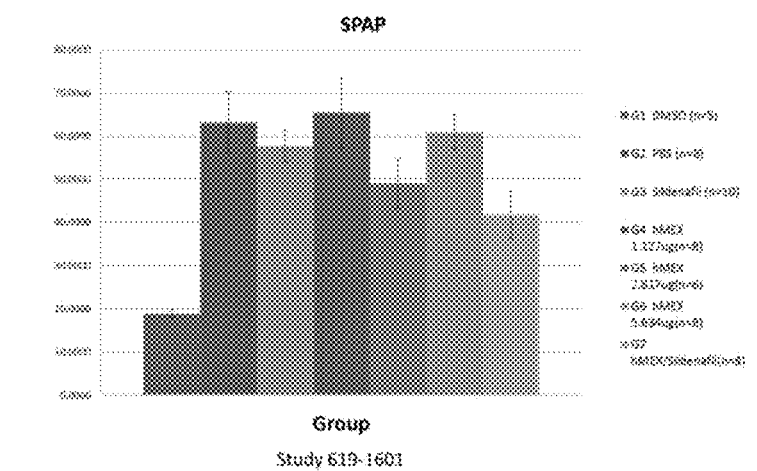
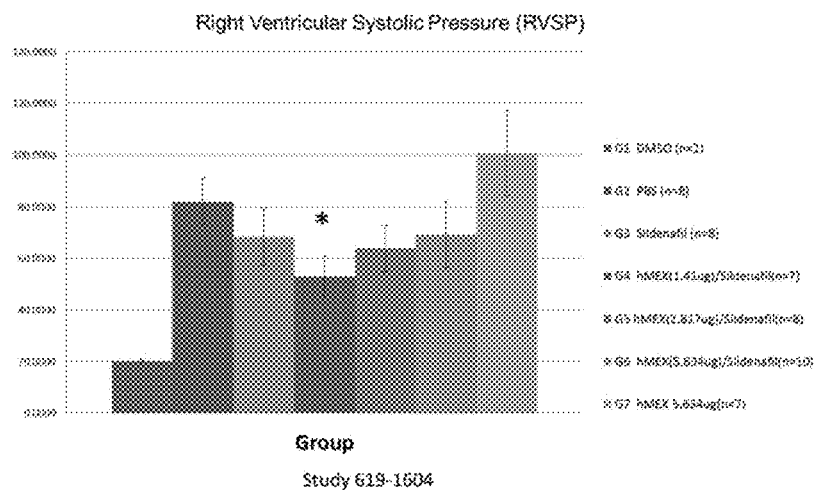

FIG. 42

1) Metabolite analysis was performed on ground heart and pulmonary artery tissue from rats

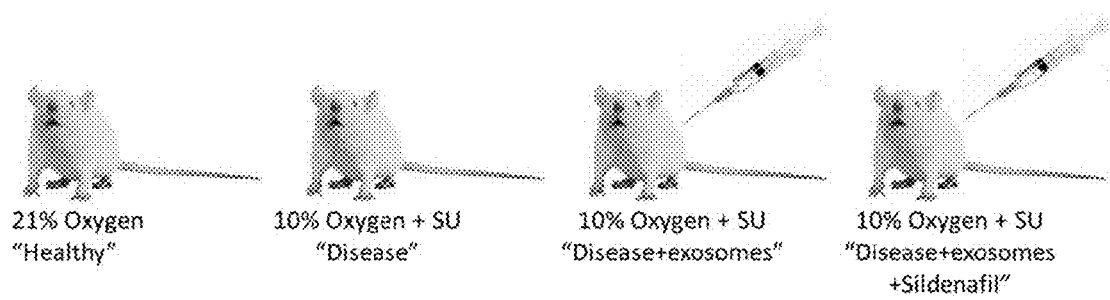

21% Oxygen
"Healthy"

10% Oxygen + SU
"Disease"

10% Oxygen + SU
"Disease+exosomes"

10% Oxygen + SU
"Disease+exosomes
+Sildenafil"

2) Metabolite and global gene expression analysis were performed on an in vitro model of PAH (chronic 2 week hypoxia exposure in human pSMCs)

Pulmonary Artery Smooth Muscle Cells

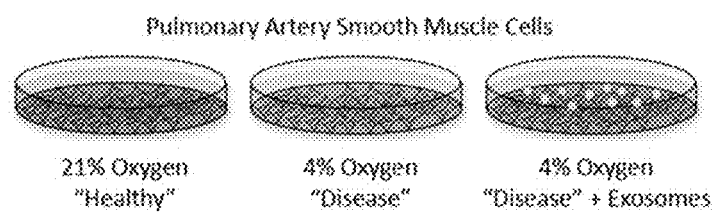

21% Oxygen
"Healthy"

4% Oxygen
"Disease"

4% Oxygen
"Disease" + Exosomes

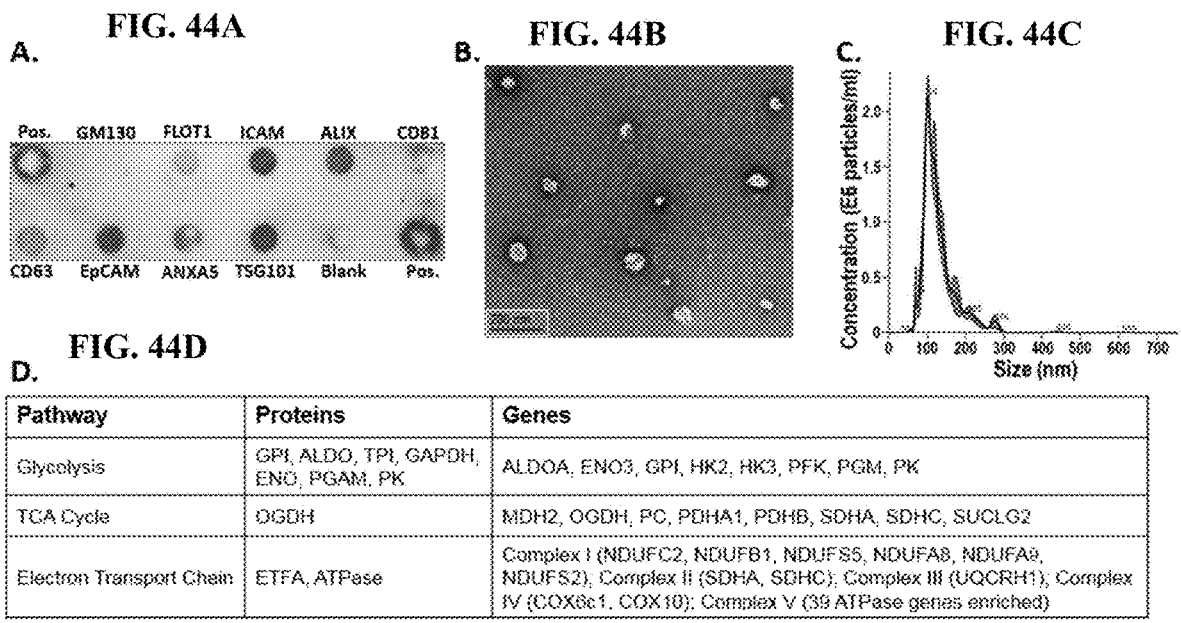

FIG. 50A.
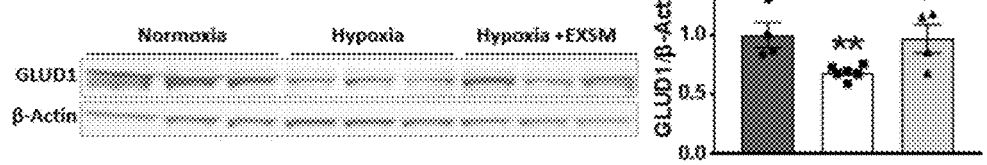
FIG. 50B.
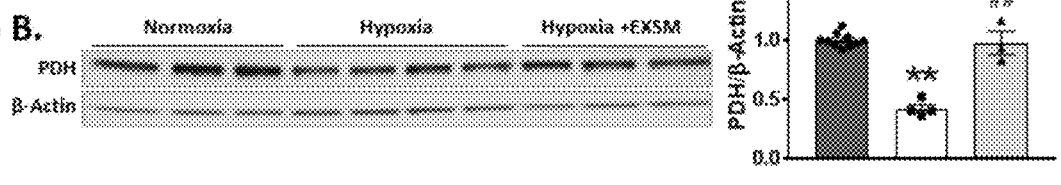
FIG. 50C.
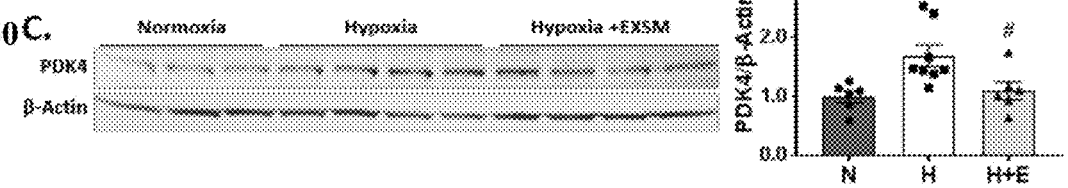
FIG. 50D.
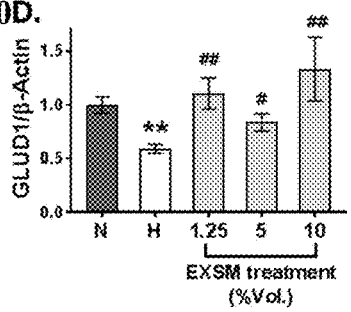
E. FIG. 50E
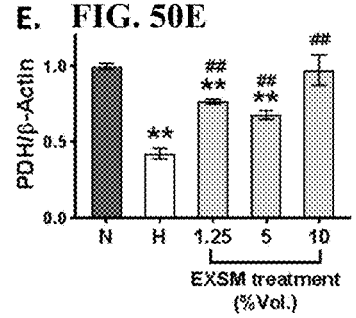
F. FIG. 50F
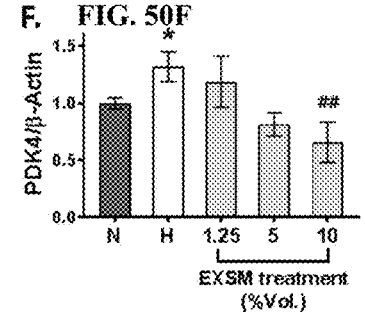

FIG. 51A
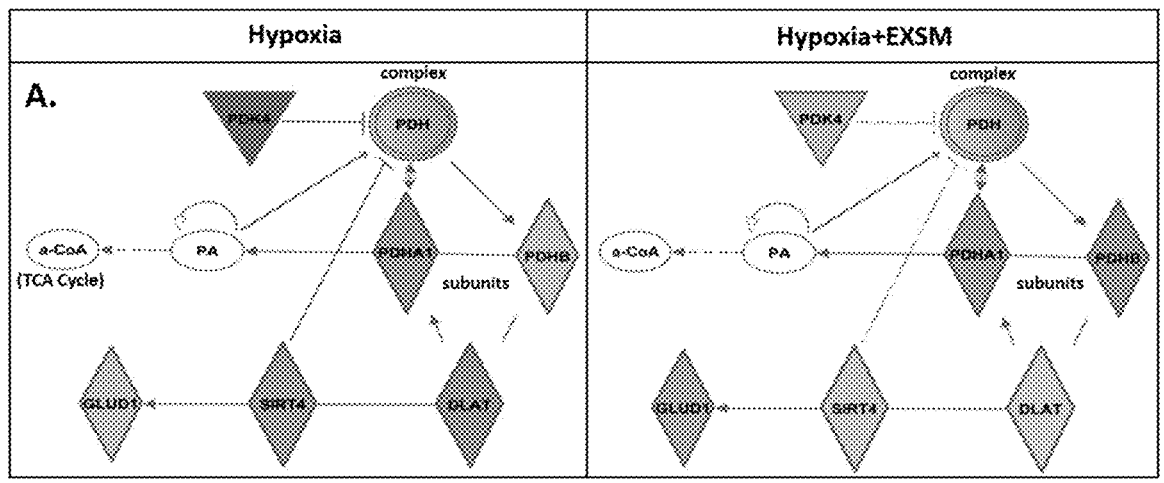
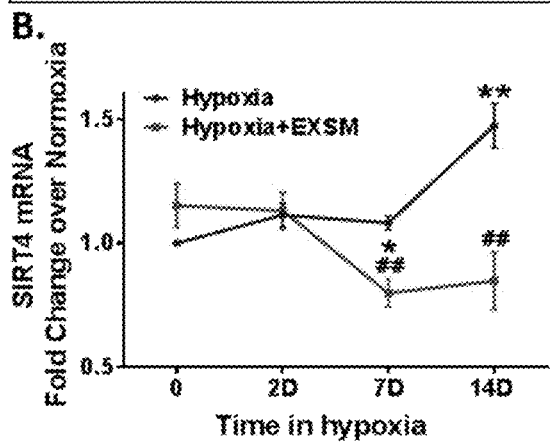
FIG. 51B
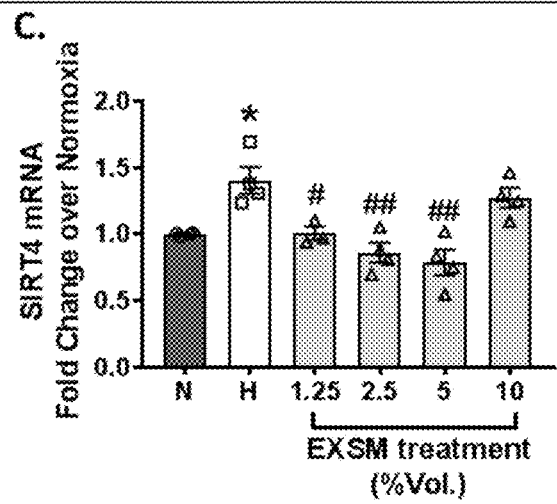
FIG. 51C

FIG. 54A
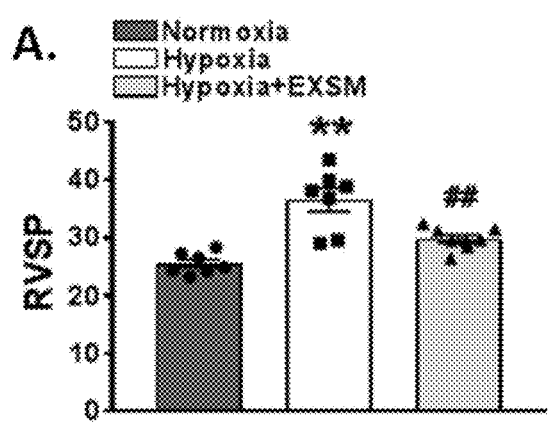
FIG. 54B
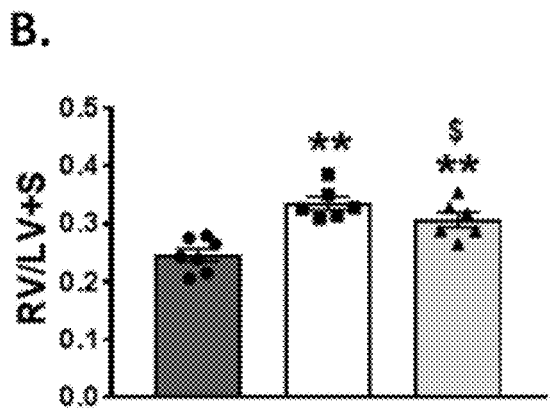
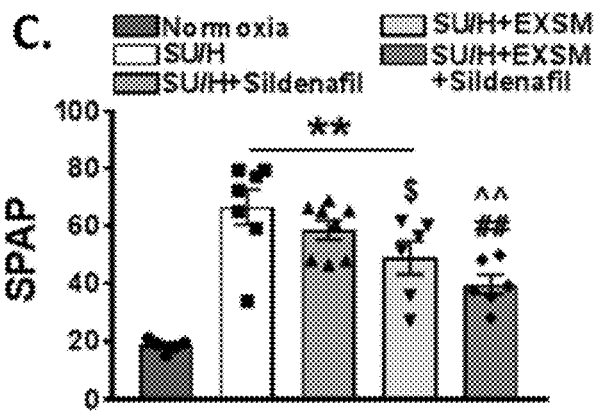
FIG. 54C
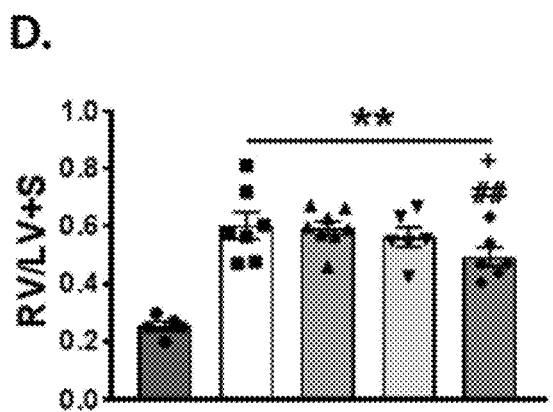
FIG. 54D

FIG. 55A
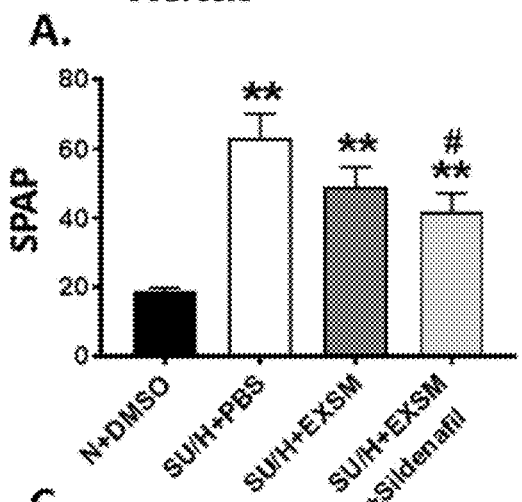
FIG. 55B
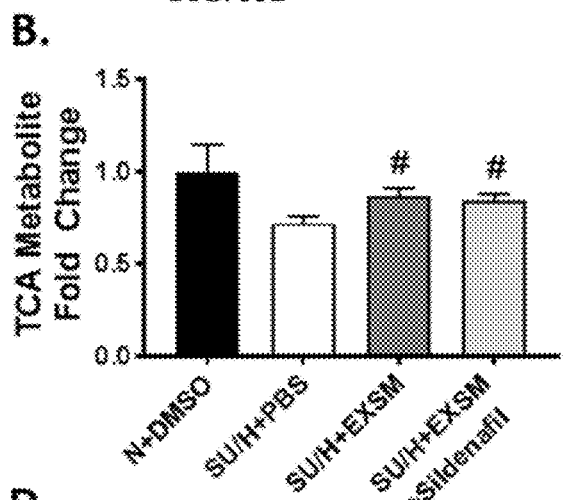
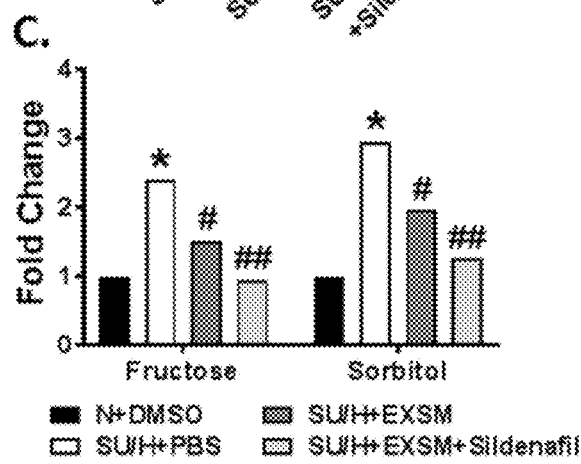
FIG. 55C
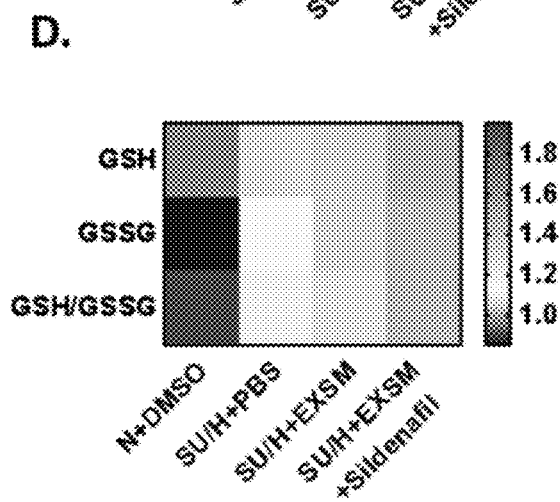
FIG. 55D

EXTRACELLULAR VESICLES WITH ENHANCED POTENCY

CROSS REFERENCE TO RELATED APPLICATIONS

This application is a continuation-in-part of U.S. patent application Ser. No. 15/625,961 filed Jun. 16, 2017, which claims priority to U.S. Provisional Patent Application No. 62/351,627 filed Jun. 17, 2016, which is hereby incorporated by reference in its entirety.

BACKGROUND

The present application relates to methods of isolating potent extracellular vesicles, including exosomes, and the use of extracellular vesicles or exosomes in treatment of pulmonary hypertension, including pulmonary arterial hypertension (PAH), and conditions and diseases associated with mitochondrial dysfunction.

Pulmonary hypertension is a progressive and often fatal disease characterized by increased pressure in the pulmonary vasculature. An increasing constriction of the pulmonary circulation leads to increased stress on the right heart, which may develop into right heart failure. By definition, the mean pulmonary arterial pressure (mPAP) in a case of chronic pulmonary hypertension is >25 mmHg at rest or >30 mmHg during exertion (normal value <20 mmHg). For example, pulmonary arterial hypertension, untreated, leads to death on average within 2.8 to 5 years after being diagnosed (Keily et al. (2013) *BMJ* 346:f2028). The pathophysiology of pulmonary arterial hypertension is characterized by vasoconstriction and remodeling of the pulmonary vessels. In chronic PAH there is neomuscularization of initially unmuscularized pulmonary vessels, and the vascular muscles of the already muscularized vessels increase in circumference. This resulting increase in pulmonary arterial pressures results in progressive stress on the right heart, which leads to a reduced output from the right heart and eventually ends in right heart failure (M. Humbert et al., *J. Am. Coll. Cardiol.* 2004, 43, 13S-24S). PAH is a rare disorder, with a prevalence of 1-2 per million. The average age of the patients has been estimated to be 36 years, and only 10% of the patients were over 60 years of age. Distinctly more women than men are affected (G. E. D'Alonzo et al., *Ann. Intern. Med.* 1991, 115, 343-349). Numerous mechanisms have been implicated in the pathogenesis of PAH. Importantly, a suppression of global metabolism has been described downstream of aberrant mitochondrial glucose oxidation in this disease. Diminished mitochondrial function could unify many apparently unrelated abnormalities in PAH, such as the involvement of multiple cell types, the cancer-like proliferation of pulmonary vascular cells, and resistance of these cells to apoptosis. Despite evidence supporting the role of mitochondrial dysfunction in PAH, therapeutic targeting of mitochondrial function has proven difficult.

Thus, a need exists to develop improved therapeutic compositions and methods for treating pulmonary hypertension, such as by targeting mitochondrial function.

SUMMARY

In one aspect, the present disclosure provides a method of treating (including preventing) pulmonary hypertension, comprising administering to a subject in need thereof isolated extracellular vesicles or exosomes obtained from mesenchymal stromal cells, wherein the isolated extracellular vesicles or exosomes comprise extracellular vesicles or exosomes having increased expression of one or more expression products selected from the group consisting of (a) genes in the glycolysis pathway, (b) genes in the TCA cycle, and (c) genes in the electron transport chain as compared to the average amount of the expression products in all extracellular vesicles or exosomes obtained from the mesenchymal stromal cells. In some embodiments, the extracellular vesicles or exosomes comprise at least 10%, 20%, 30%, 50%, or 100% more expression of the expression products compared to the average level of the same expression product in all extracellular vesicles or exosomes obtained from the mesenchymal stromal cells.

In some embodiments, the isolated extracellular vesicles or exosomes have increased expression of protein(s) of one or more genes selected from the group consisting of (a) genes in the glycolysis pathway, (b) genes in the TCA cycle, and (c) genes in the electron transport chain. In some embodiments, the isolated extracellular vesicles or exosomes have increased expression of RNA(s) of one or more genes selected from the group consisting of (a) genes in the glycolysis pathway, (b) genes in the TCA cycle, (c) genes in the electron transport chain.

In some embodiments, (a) the gene in the glycolysis pathway is selected from the group consisting of PK, AGI, ALDO, ALDOA, ENO3, GPI, HK2, HK3, PFK, PGM, TPI, GAPDH, ENO, and PGAM, (b) the gene in the TCA cycle is selected from the group consisting of MDH2, OGDH, PC, PDHA1, PDHB, SDHA, SDHC, and SUCLG2, and (c) the gene in the electron transport chain is selected from the group consisting of ETFA, ATPase, NDUFC2, NDUFB1, NDUFS5, NDUFA8, NDUFA9, NDUFS2, SDHA, SDHC, UQCRH1, Cox 6c1, and Cox10.

In some embodiments, the gene is PK. In some other embodiments, the gene is ATPase.

In some embodiments, the isolated extracellular vesicles or exosomes normalizes glucose oxidation in the subject. In some embodiments, the isolated extracellular vesicles or exosomes normalize glucose oxidation in lung tissue of the subject. In some embodiments, the isolated extracellular vesicles or exosomes has a PK activity of at least 0.15 nmol/min/mL.

In some embodiments, isolated extracellular vesicles or exosomes are capable of reducing Right Ventricular Systolic Pressure (RVSP) of mice subjected to a three-week chronic hypoxia exposure by at least 10%, compared to control mice subjected to a three-week chronic hypoxia exposure and treated with PBS.

In some embodiments, the isolated extracellular vesicles or exosomes are capable of increasing $O_2$ consumption by smooth muscle cell (SMC) cell lysates subjected to a 24-hour hypoxia exposure by at least 20% compared to control SMC cell lysates subjected to a 24-hour hypoxia exposure and treated with PBS control.

In some embodiments, the isolated extracellular vesicles or exosomes express one or more of FLOT1, ICAM, ALIX, CD81, CD63, EpCAM, ANXA5, and TSG101. In some embodiments, the isolated extracellular vesicles or exosomes do not express GM130.

In some embodiments, the isolated extracellular vesicles or exosomes are effective for upregulating GLUD1 gene expression in the subject. In some embodiments, the isolated extracellular vesicles or exosomes are effective for upregulating PDH gene expression in the subject. In some embodiments, the isolated extracellular vesicles or exosomes are effective for downregulating PDK4 gene expression in the subject. In some embodiments, the isolated extracellular vesicles or exosomes are effective for downregulating SIRT4 gene expression in the subject.

In some embodiments, the subject suffers from increased expression of HSP90 associated with mitochondria damage, and the isolated extracellular vesicles or exosomes are effective for downregulating the expression of HSP90. In some embodiments, the subject suffers from increased expression of TNF associated with mitochondria damage, and the isolated extracellular vesicles or exosomes are effective for downregulating the expression of TNF. In some embodiments, the subject suffers from increased expression of FASLG associated with mitochondria damage, and the isolated extracellular vesicles or exosomes are effective for downregulating the expression of FASLG. In some embodiments, the subject suffers from decreased expression of COX4 associated with mitochondria damage, and the isolated extracellular vesicles or exosomes are effective for upregulating the expression of COX4. In some embodiments, the subject suffers from decreased expression of LMX1B associated with mitochondria damage, and the isolated extracellular vesicles or exosomes are effective for upregulating the expression of LMX1B. In some embodiments, the subject suffers from decreased expression of TP53 associated with mitochondria damage, and the isolated extracellular vesicles or exosomes are effective for upregulating the expression of TP53.

In some embodiments, the subject suffers from increased proliferation of PASMC, and the isolated extracellular vesicles or exosomes are effective for downregulating the proliferation of PASMC.

In some embodiments, the subject suffers from increased heart rate associated with PAH, and the isolated extracellular vesicles or exosomes are effective for downregulating the heart rate. In some embodiments, the subject suffers from decreased cardiac output associated with PAH, and the isolated extracellular vesicles or exosomes are effective for upregulating the cardiac output.

In some embodiments, the subject suffers from increased right ventricular weight associated with PAH, and the isolated extracellular vesicles or exosomes are effective for downregulating the right ventricular weight. In some embodiments, the subject suffers from increased right ventricular to left ventricular and septum weight ratio associated with PAH, and the isolated extracellular vesicles or exosomes are effective for downregulating the right ventricular to left ventricular and septum weight ratio.

In some embodiments, the subject suffers from decreased expression of TFAM associated with mitochondria damage, and the isolated extracellular vesicles or exosomes are effective for upregulating the expression of TFAM.

In another aspect, the present disclosure provides a method of treating a disease or condition associated with mitochondrial dysfunction, comprising administering to a subject in need thereof isolated extracellular vesicles or exosomes obtained from mesenchymal stromal cells, wherein the isolated extracellular vesicles or exosomes comprise extracellular vesicles or exosomes having increased expression of one or more expression products selected from the group consisting of (a) genes in the glycolysis pathway, (b) genes in the TCA cycle, and (c) genes in the electron transport chain as compared to the average level of the expression product in all extracellular vesicles or exosomes obtained from the mesenchymal stromal cells.

In some embodiments, the isolated extracellular vesicles or exosomes have increased expression of protein(s) of one or more genes selected from the group consisting of (a) genes in the glycolysis pathway, (b) genes in the TCA cycle, and (c) genes in the electron transport chain. In some embodiments, the isolated extracellular vesicles or exosomes have increased expression of RNA(s) of one or more genes selected from the group consisting of (a) genes in the glycolysis pathway, (b) genes in the TCA cycle, and (c) genes in the electron transport chain.

In some embodiment, (a) the gene in the glycolysis pathway is selected from the group consisting of PK, AGI, ALDO, ALDOA, ENO3, GPI, HK2, HK3, PFK, PGM, TPI, GAPDH, ENO, and PGAM, (b) the gene in the TCA cycle is selected from the group consisting of MDH2, OGDH, PC, PDHA1, PDHB, SDHA, SDHC, and SUCLG2, and (c) the gene in the electron transport chain is selected from the group consisting of ETFA, ATPase, NDUFC2, NDUFB1, NDUFS5, NDUFA8, NDUFA9, NDUFS2, SDHA, SDHC, UQCRH1, Cox 6c1, and Cox10.

In some embodiments, the gene is PK. In some other embodiments, the gene is ATPase. In some embodiments, the isolated extracellular vesicles or exosomes normalize glucose oxidation in lung tissue of the subject. In some embodiments, the isolated extracellular vesicles or exosomes have a PK activity of at least 0.15 nmol/min/mL.

In some embodiments, the disease or condition associated with mitochondrial dysfunction is associated with decreased mitochondrial glucose oxidation in the subject. In some embodiments, the disease or condition associated with mitochondrial dysfunction is selected from the group consisting of Friedreich's ataxia, Leber's Hereditary Optic Neuropathy, Kearns-Sayre Syndrome, Mitochondrial Encephalomyopathy with Lactic Acidosis and Stroke-Like Episodes, Leigh syndrome, obesity, atherosclerosis, amyotrophic lateral sclerosis, Parkinson's Disease, cancer, heart failure, myocardial infarction (MI), Alzheimer's Disease, Huntington's Disease, schizophrenia, bipolar disorder, fragile X syndrome, and chronic fatigue syndrome.

In some embodiments, the isolated extracellular vesicles or exosomes express one or more of FLOT1, ICAM, ALIX, CD81, CD63, EpCAM, ANXA5, and TSG101. In some embodiments, the isolated extracellular vesicles or exosomes do not express GM130.

In some embodiments, the isolated extracellular vesicles or exosomes are effective for upregulating GLUD1 gene expression in the subject. In some embodiments, the isolated extracellular vesicles or exosomes are effective for upregulating PDH gene expression in the subject. In some embodiments, the isolated extracellular vesicles or exosomes are effective for downregulating PDK4 gene expression in the subject. In some embodiments, the isolated extracellular vesicles or exosomes are effective for downregulating SIRT4 gene expression in the subject.

In some embodiments, the subject suffers from increased expression of HSP90 associated with mitochondria damage, and the isolated extracellular vesicles or exosomes are effective for downregulating the expression of HSP90. In some embodiments, the subject suffers from increased expression of TNF associated with mitochondria damage, and the isolated extracellular vesicles or exosomes are effective for downregulating the expression of TNF. In some embodiments, the subject suffers from increased expression of FASLG associated with mitochondria damage, and the isolated extracellular vesicles or exosomes are effective for downregulating the expression of FASLG. In some embodiments, the subject suffers from decreased expression of COX4 associated with mitochondria damage, and the isolated extracellular vesicles or exosomes are effective for upregulating the expression of COX4. In some embodiments, the subject suffers from decreased expression of LMX1B associated with mitochondria damage, and the isolated extracellular vesicles or exosomes are effective for upregulating the expression of LMX1B. In some embodiments, the subject suffers from decreased expression of TP53 associated with mitochondria damage, and the isolated extracellular vesicles or exosomes are effective for upregulating the expression of TP53.

In some embodiments, the subject suffers from decreased expression of TFAM associated with mitochondria damage, and the isolated extracellular vesicles or exosomes are effective for upregulating the expression of TFAM.

In another aspect, the present disclosure provides a method of isolating extracellular vesicles or exosomes capable of treating or preventing pulmonary hypertension, comprising the following steps: (a) providing a culture media of mesenchymal stromal cells comprising extracellular vesicles or exosomes; (b) separating at least a portion of the extracellular vesicles or exosomes from the other components of the culture media; and (c) isolating an extracellular vesicle or exosome population from other extracellular vesicle or exosome populations, wherein the population has increased expression of one or more expression products selected from the group consisting of (a) genes in the glycolysis pathway, (b) genes in the TCA cycle, and (c) genes in the electron transport chain as compared to the average amount of the expression products in all extracellular vesicles or exosomes obtained from the mesenchymal stromal cells.

In another aspect, the present disclosure provides a method of isolating extracellular vesicles or exosomes capable of treating or preventing pulmonary hypertension, comprising the following steps: (a) providing a culture media of mesenchymal stromal cells comprising extracellular vesicles or exosomes; (b) separating at least a portion of the extracellular vesicles or exosomes from the other components of the culture media; (c) separating different populations of extracellular vesicles or exosomes based on molecular size; (d) treating hypoxia-exposed mice with the different populations of extracellular vesicles or exosomes; (e) measuring Right Ventricular Systolic Pressure (RVSP) of normoxia mice, hypoxia-exposed mice and hypoxia exposed mice treated with the extracellular vesicles or exosomes; and (f) identifying a potent population of extracellular vesicles or exosomes based on the RVSP.

In some embodiments, a population of extracellular vesicles or exosomes is potent if the ratio of RVSP of hypoxia-exposed mice treated with the extracellular vesicles or exosomes to RVSP of hypoxia-exposed mice is 0.85 or less.

In some embodiments, a population of extracellular vesicles or exosomes is potent if delta RVSP is less than 5 mmHg, wherein delta RVSP is RVSP of hypoxia-exposed mice treated with extracellular vesicles or exosomes minus RVSP of normoxia mice.

In some embodiments, in step c, different populations of extracellular vesicles or exosomes are separated by phospholipid detection.

In some embodiments, the potent population of extracellular vesicles or exosomes have increased expression of one or more expression products selected from the group consisting of (a) genes in the glycolysis pathway, (b) genes in the TCA cycle, and (c) genes in the electron transport chain as compared to the average amount of the expression products in all extracellular vesicles or exosomes obtained from the mesenchymal stromal cells. In some embodiments, the potent population of extracellular vesicles or exosomes have increased expression of protein(s) of one or more genes selected from the group consisting of (a) genes in the glycolysis pathway, (b) genes in the TCA cycle, and (c) genes in the electron transport chain. In some embodiments, the potent population of extracellular vesicles or exosomes have increased expression of RNA(s) of one or more genes selected from the group consisting of (a) genes in the glycolysis pathway, (b) genes in the TCA cycle, and (c) genes in the electron transport chain.

In some embodiments, (a) the gene in the glycolysis pathway is selected from the group consisting of PK, AGI, ALDO, ALDOA, ENO3, GPI, HK2, HK3, PFK, PGM, TPI, GAPDH, ENO, and PGAM, (b) the gene in the TCA cycle is selected from the group consisting of MDH2, OGDH, PC, PDHA1, PDHB, SDHA, SDHC, and SUCLG2, and (c) the gene in the electron transport chain is selected from the group consisting of ETFA, ATPase, NDUFC2, NDUFB1, NDUFS5, NDUFA8, NDUFA9, NDUFS2, SDHA, SDHC, UQCRH1, Cox 6c1, and Cox10.

In some embodiments, the gene is PK. In some embodiments, the gene is ATPase.

In another aspect, the present disclosure provides a method of isolating extracellular vesicles or exosomes capable of treating or preventing bronchopulmonary dysplasia, comprising the following steps: (a) providing a culture media of mesenchymal stromal cells comprising extracellular vesicles or exosomes; (b) separating at least a portion of the extracellular vesicles or exosomes from the other components of the culture media; (c) separating different populations of extracellular vesicles or exosomes based on molecular size; (d) treating hypoxia-exposed mice with the different populations of extracellular vesicles or exosomes; (e) measuring Right Ventricular Systolic Pressure (RVSP) of normoxia mice, hypoxia-exposed mice and hypoxia exposed mice treated with the extracellular vesicles or exosomes; and (f) identifying a potent population of extracellular vesicles or exosomes based on the RVSP.

In some embodiments, step (b) of the method separates a portion of the extracellular vesicles or exosomes from the other components of the culture media by size exclusion chromatography.

In another aspect, the present disclosure provides a composition comprising isolated extracellular vesicles or exosomes obtained according to any of the methods described in this disclosure. In some embodiments, the isolated extracellular vesicles or exosomes have a mean diameter of about 100 nm. In some embodiments, the isolated extracellular vesicles or exosomes have a mean diameter of about 80-120 nm. In some embodiments, at least 50%, or at least 60%, or at least 70%, or at least 80%, or at least 90%, or at least 95% of the isolated extracellular vesicles or exosomes have a size between 50 nm and 150 nm. In some embodiments, the average concentration of the isolated extracellular vesicles or exosomes is about $1\times10^7$ to $1\times10^9$ particles/ml, or about $1\times10^8$ particles/ml.

In some embodiments, the isolated extracellular vesicles or exosomes express FLOT and/or ANXA2. In some embodiments, the isolated extracellular vesicles or exosomes have increased expression of mir204, compared to the average amount of mir204 in all extracellular vesicles or exosomes of the mesenchymal stromal cells. In some embodiments, the isolated extracellular vesicles or exosomes have are secreted from MSCs containing increased expression of CD105, GAPDH, DLST, and/or ATP5A1, compared to the average amount of CD105, GAPDH, DLST, and/or ATP5A1 in all extracellular vesicles or exosomes of the mesenchymal stromal cells. In some embodiments, the isolated extracellular vesicles or exosomes have increased RNA expression of SORCS1, FHIT and/or ANKRD30BL, compared to the average amount of SORCS1, FHIT and/or ANKRD30BL in all extracellular vesicles or exosomes of the mesenchymal stromal cells. In some embodiments, the isolated extracellular vesicles or exosomes are substantially free of MHCII contaminants. In some embodiments, the isolated extracellular vesicles or exosomes are substantially free of fibronectin.

In some embodiments, the isolated extracellular vesicles or exosomes express one or more of FLOT1, ICAM, ALIX, CD81, CD63, EpCAM, ANXA5, and TSG101. In some embodiments, the isolated extracellular vesicles or exosomes do not express GM130.

In another aspect, the present disclosure provides a method of treating or preventing bronchopulmonary dysplasia, comprising administering to a subject in need thereof isolated extracellular vesicles or exosomes obtained according any of the methods described in this disclosure. In some embodiments, the isolated extracellular vesicles or exosomes increase immunomodulatory capacity of the subject. In some embodiments, the isolated extracellular vesicles or exosomes reduces IL-6 and/or TNFα expression in the subject. In some embodiments, the isolated extracellular vesicles or exosomes promote angiogenesis of the subject. In some embodiments, the isolated extracellular vesicles or exosomes reduce hyperoxia-induced apoptosis in the subject. In some embodiments, the isolated extracellular vesicles or exosomes reduces Cytochrome C level in the subject. In some embodiments, the isolated extracellular vesicles or exosomes increase mitochondrial metabolism of the subject. In some embodiments, the isolated extracellular vesicles or exosomes restore tube formation in the subject. In some embodiments, the isolated extracellular vesicles or exosomes upregulate GLUD1 and/or PDH gene expression in the subject. In some embodiments, the isolated extracellular vesicles or exosomes downregulate PDK4 gene expression in the subject. In some embodiments, the isolated extracellular vesicles or exosomes downregulate SIRT4 gene expression in the subject.

In some embodiments, the method of treating or preventing pulmonary hypertension and/or bronchopulmonary dysplasia further comprises administering sildenafil to the subject.

BRIEF DESCRIPTION OF THE DRAWINGS

The provided drawings exemplify, but do not limit, the disclosed subject matter.

FIGS. 1A-1C show isolation of exosomes from MSC culture media and their potency in preventing chronic hypoxia-induced PAH in mice. FIG. 1A shows different exosome populations isolated based on size exclusion chromatography. FIG. 1B shows overlay of exosomes isolated by phospholipid concentration detection and A280 chromatogram. FIG. 1C shows the effect of isolated exosomes in treating mice with hypoxia-induced PAH. The potent exosome population (EXM2 shown as green dot) prevented chronic hypoxia-induced PAH in mice, while the other exosome population (EXM1 shown as red dot) did not.

FIG. 2A shows pyruvate kinase activity of the exosome populations plotted against RVSP fold change between hypoxia treatment group and hypoxia control. FIG. 2B shows pyruvate kinase activity of the exosome populations plotted against delta RVSP. The red dots represent potent exosome populations that induced a significant improvement in RVSP. The blue dots represent exosome populations that are not potent in treating hypoxia induced PAH mice. FIG. 2C shows pyruvate kinase activity of the potent exosome populations graphed in a box and whisker plot.

FIG. 3A shows that in potent exosome populations, proteins involved in glycolysis, the TCA cycle, and the electron transport chain that have increased expression level. FIG. 3B shows Western blot analysis of pyruvate kinase of both the potent exosome population (EXM2) and the non-potent exosome population (EXM1).

FIG. 4 shows RNAseq analysis of different exosome populations. The results demonstrated that potent exosome populations contained an enrichment of genes involved in glycolysis, TCA cycle and electron transport chain, which suggests the potential for potent exosome population for genetic reprogramming to increase glucose oxidation (a).

FIG. 5A shows $O_2$ consumption calculated as slope normalized to PBS control. FIG. 5B shows $O_2$ consumption calculated as area under the curve normalized to PBS control. The results of FIGS. 5A and 5B show that exosomes do not significantly change the cellular $O_2$ consumption in normoxia-exposed SMCs. On the other hand, exosome treatment induces an increase in $O_2$ consumption under hypoxia stress, which indicates an increase in mitochondrial function.

FIG. 6A shows an increase in ENO1 gene expression in glycolysis after hypoxia exposure, which is normalized by exosome treatment. FIG. 6B shows an increase in PDHB and ACLY gene expression in the TCA cycle after hypoxia exposure, which is normalized by exosome treatment. FIG. 6C shows an increase in NDUFAF3, ATP2B4, ATP5H, ATP91gene expression in electron transport chain after hypoxia exposure, which is normalized by exosome treatment.

FIG. 7A shows fold change of metabolites levels in glycolysis. FIG. 7B shows fold change of metabolites levels in the TCA cycle. FIG. 7C shows fold change of metabolites levels in electron transport chain. FIG. 7D comparison of ATP production in live SMCs exposed to hypoxia with and without treatment with exosomes. (# means $p \leq 0.05$ compared to normoxia; $ means $p \leq 0.05$ compared to hypoxia; * means $p \leq 0.1$ compared to normoxia, and $p \leq 0.1$ compared to hypoxia) The results showed a buildup of metabolites in glycolysis, TCA cycle and energy metabolism after hypoxia exposure, due to decreased flux through these pathways. Exosome treatment increased flux through these pathways, which indicates that exosome treatment increases glucose oxidation and normalizes SMC stress response to acute hypoxia.

FIG. 8A shows activity of media LDH in SMC lysate after exposure to 24 hour hypoxia. FIG. 8B shows the level of media citrate in SMC lysate after exposure to 24 hour hypoxia. FIG. 8C shows activity of media LDH in SMC lysate after exposure to chronic 2 week hypoxia. FIG. 8D shows the level of media citrate in SMC lysate exposure to chronic 2 week hypoxia. FIG. 8E shows protein expression of pyruvate dehydrogenase active subunit (PDH E1α), the PDH E1α inhibitor pyruvate dehydrogenase kinase (PDK), and ATPase in SMC lysate exposure to chronic 2 week hypoxia. (# means p≤0.05 compared to normoxia; $ means p≤0.05 compared to hypoxia; * means p≤0.1 compared to normoxia, and p≤0.1 compared to hypoxia) The results show that exosome treatment normalizes mitochondrial function after acute and chronic hypoxia exposure.

Figure 9:
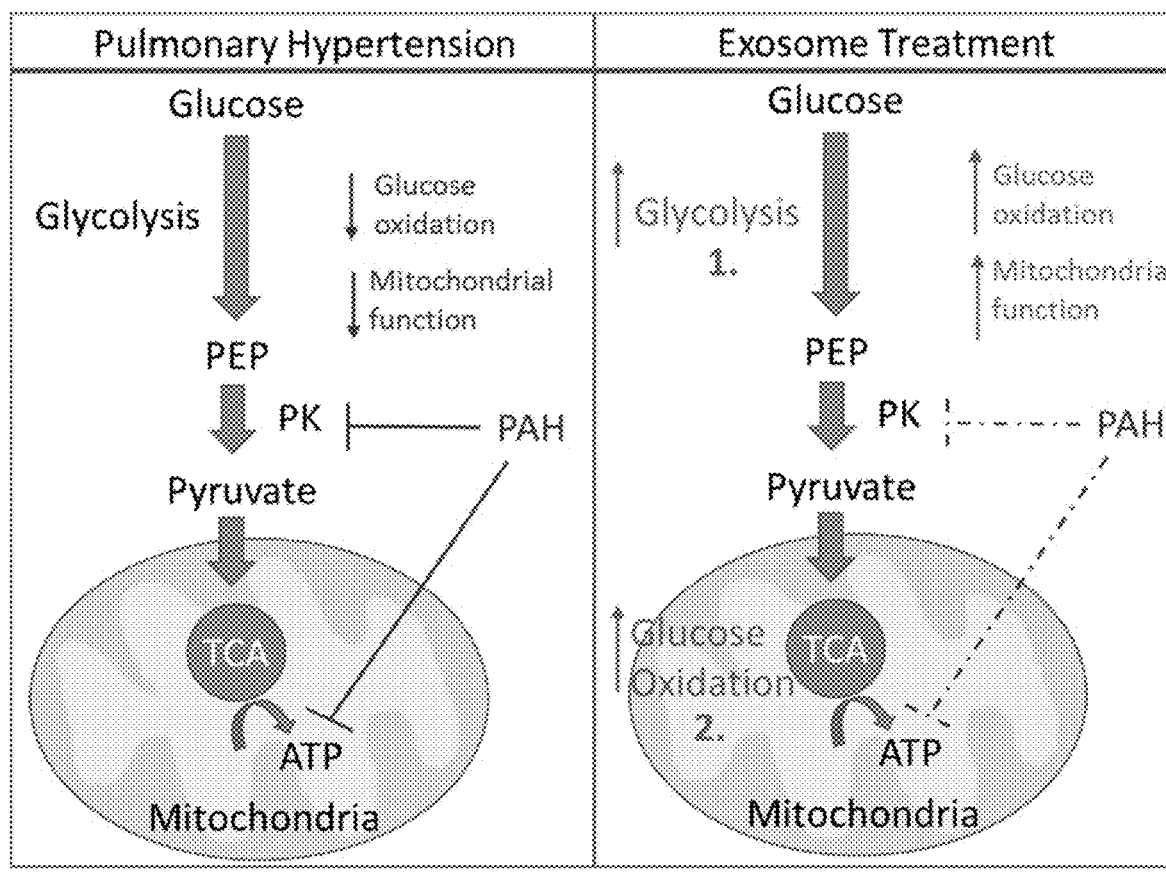

FIG. 9 shows a proposed model for exosome treatment. In particular, Pulmonary hypertension suppresses mitochondrial glucose oxidation, leads to a decrease in global mitochondrial function. Exosome treatment normalizes glucose oxidation and improve mitochondrial capacity both by acute protein integration and/or chronic genetic upregulation of enzymes in glycolysis (1) and the TCA cycle and the election transport chain within the mitochondria (2).

Figure 10:
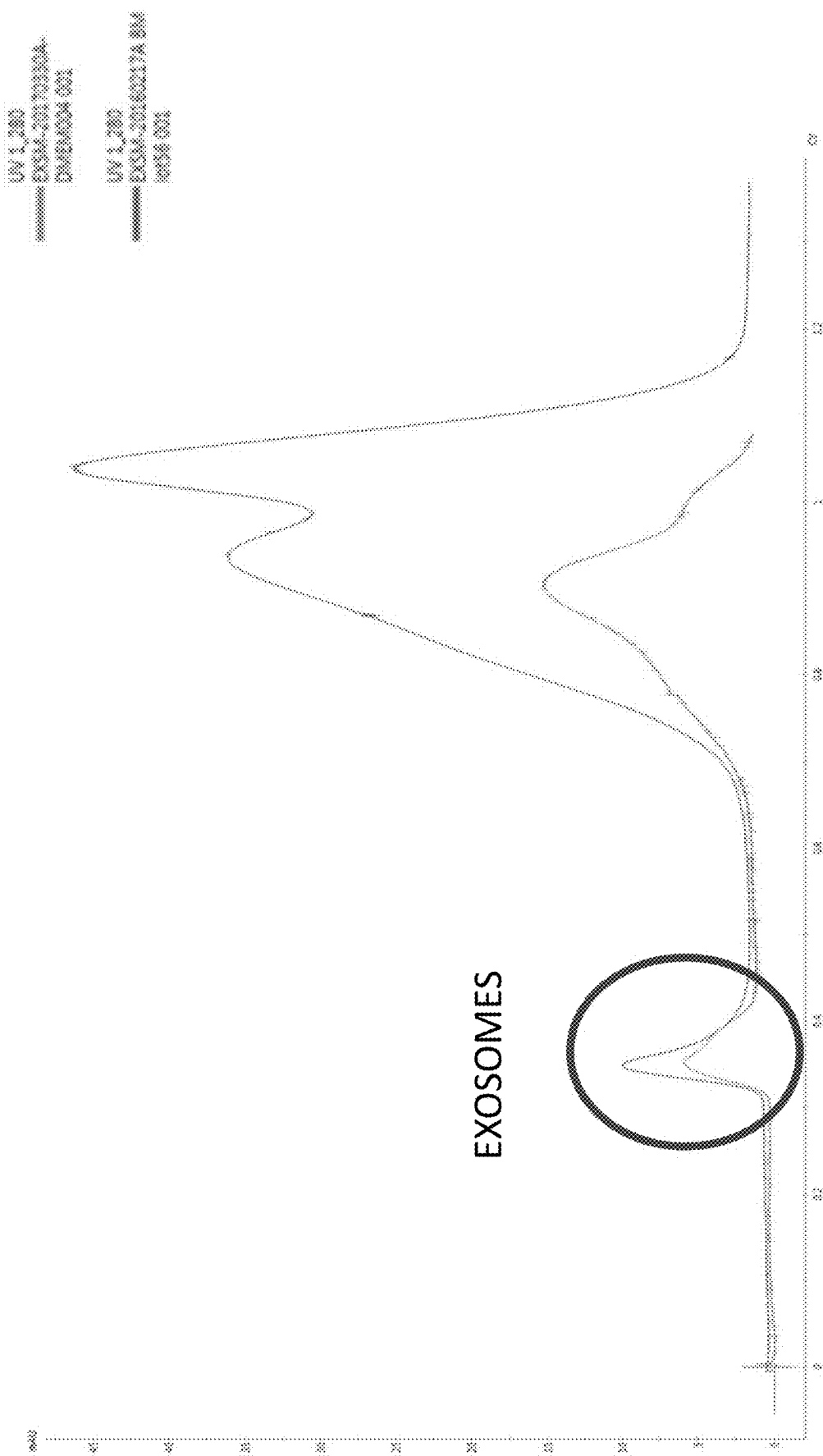

FIG. 10 shows comparison of chromatograms of exosomes produced without a diafiltration step (blue) and with a diafiltration step (orange). The blue chromatogram has a much higher A280 reading than the orange one, suggesting higher amount of protein in the sample compared to the diafiltrated sample. The diafiltration step is similar to buffer exchange, which includes adding PBS buffer into the reservoir to maintain the volume while continuing to run the pump to the TFF cassette filter, once a desired concentration of exosomes is reached. Gradually, the PBS will replace the conditioned media. In order to achieve as complete of an exchange as possible, 7 total volume diafiltrations were performed to with the retentate. This step helps to remove some of the impurities in the retentate, without affecting exosomes. The presence of exosomes was verified with FLOT-1 western blots. The figure shows that the diafiltration step helps to remove impurities as shown by decreased amount of total protein and phospholipid while retaining exosomes.

Figure 11A:
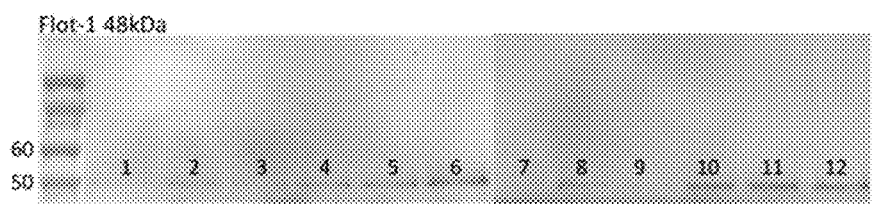
Figure 11B:
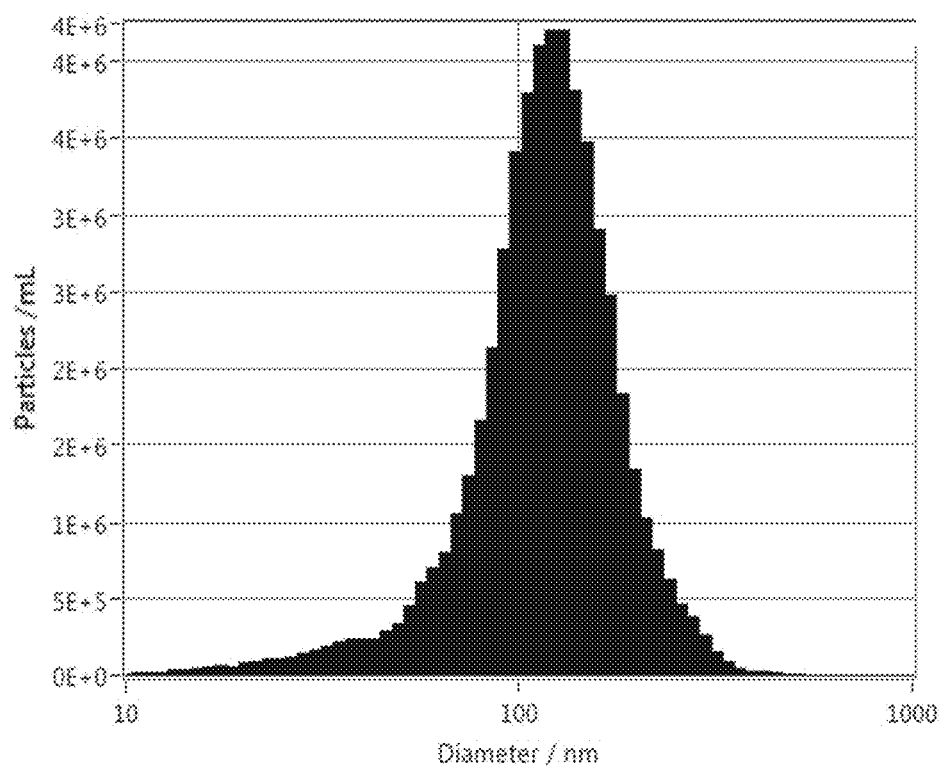

FIGS. 11A-11B shows exosome production analysis. FIG. 11A shows FLOT-1 western blot analysis of 12 samples. FIG. 11B shows the size distribution of exosomes, with has a median diameter of about 100 nm.

Figure 12:
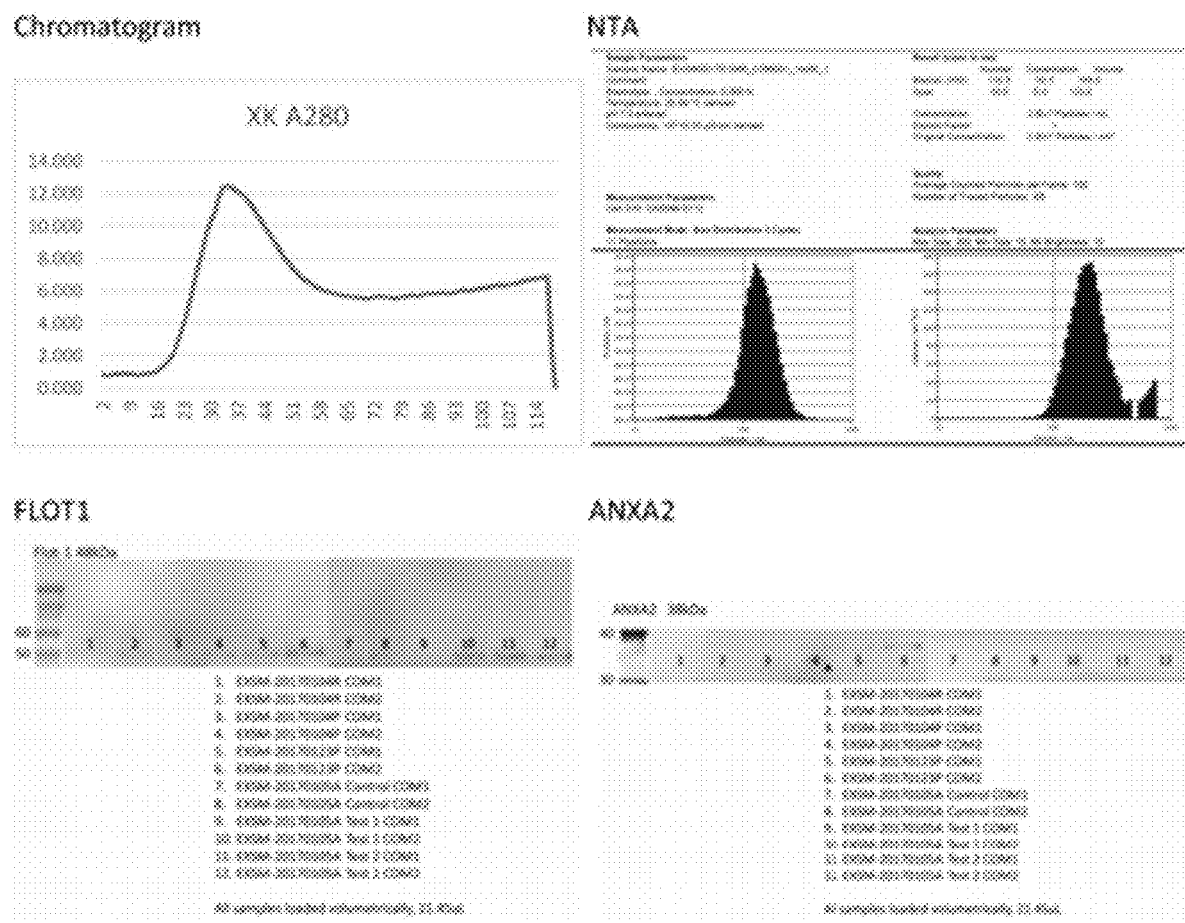

FIG. 12 shows supplemental analysis and assessment of exemplary exosome production, including chromatogram, NTA, FLOT-1 western blot and ANXA2 western blot.

Figure 13A:
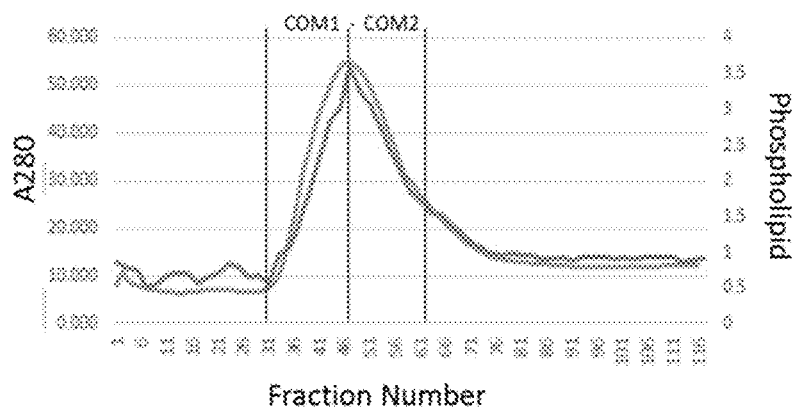
Figure 13B:
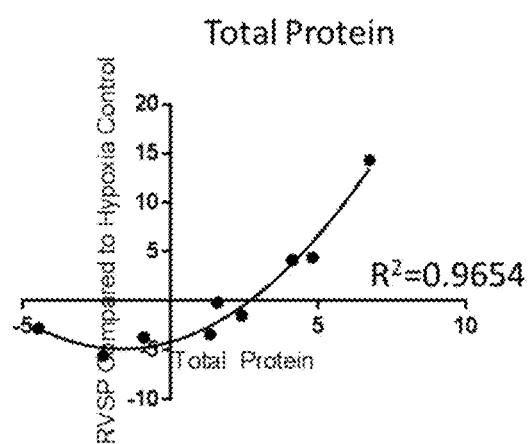
Figure 13C:
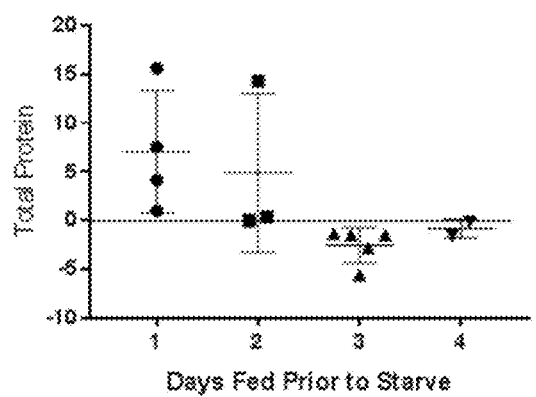

FIGS. 13A-13C shows analysis of potent exosomes. FIG. 13A shows chromatograms of COM1 (large and non-potent population of exosomes) and COM2 (small and potent population of exosomes). FIG. 13B shows plotting total protein against RVSP (in an animal model of hypoxia-induced pulmonary hypertension) from each preparation compared to hypoxia control. The results show that when more protein resides in the large non-potent fraction, the resulting preparations are potent. FIG. 13C shows plotting total protein against days fed prior to starve. The results show that positive delta protein (designating potent preparations) were all consistently fed 1 day prior to starve.

Figure 14:
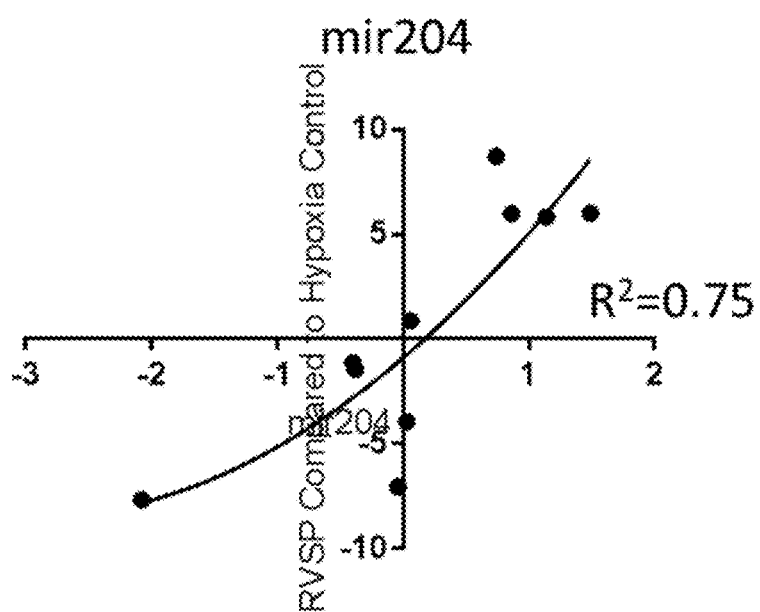
Figure 15A:
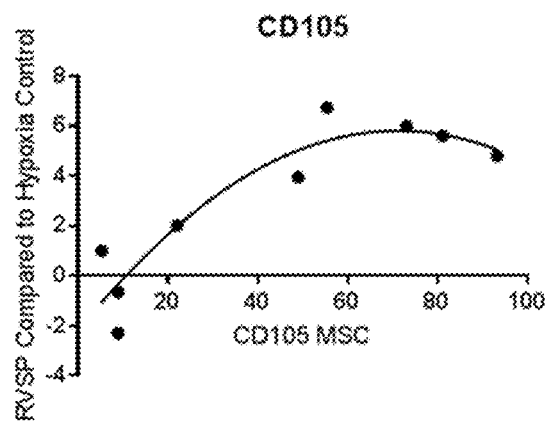
Figure 15B:
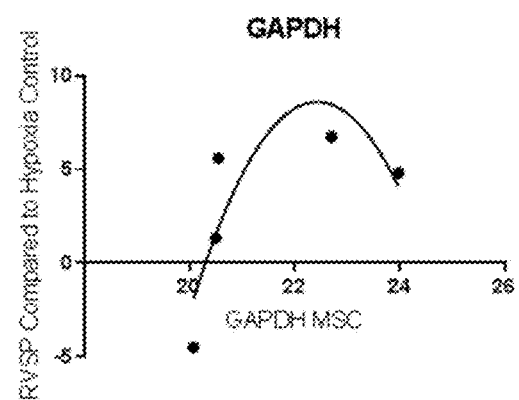
Figure 15C:
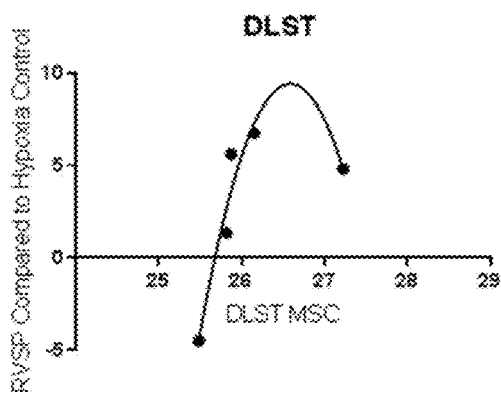
Figure 15D:
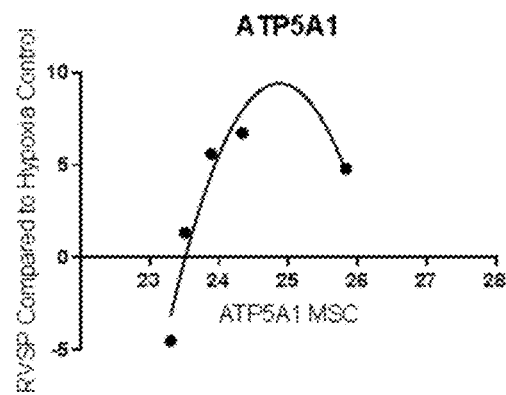

FIG. 14 shows plotting mir204 (a small non-coding RNA molecule containing about 22 nucleotides functions in RNA silencing and post-transcriptional regulation of gene expression). COM1 has higher cycle threshold (CT) value, corresponding to lower miRNA and lower potency. In contrast, COM2 has increased mir204 expression.

FIGS. 15A-15D shows that the potency of exosomes is positively correlated to CD105 protein expression (FIG. 15A), GAPDH gene expression (FIG. 15B), DLST gene expression (FIG. 15C), and ATP5A1 gene expression (FIG. 15D) in the parent MSC cell. The results show that cell metabolic health directly correlates with exosome potency.

Figure 16A:
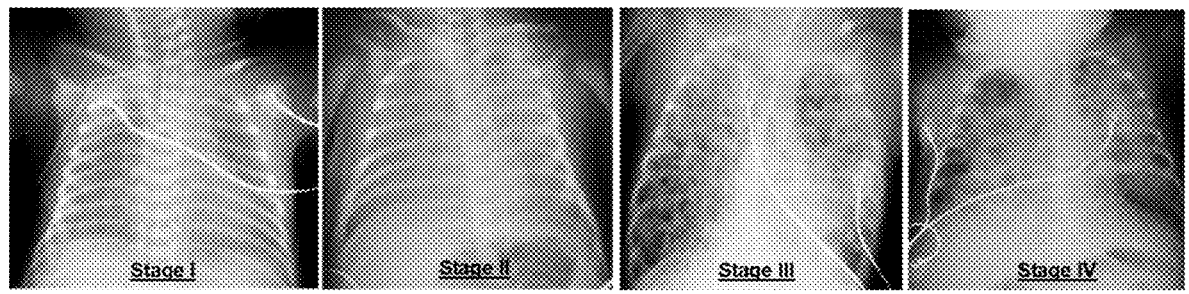
Figure 16B:
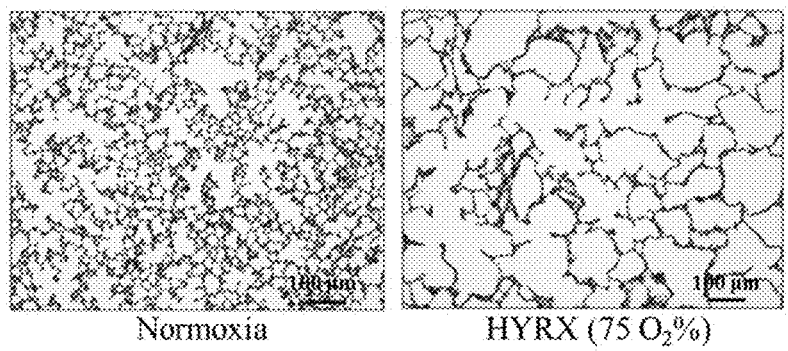

FIGS. 16A-16B shows disrupted lung development of Bronchopulmonary Dysplasia (BPD) patients. FIG. 16A shows radiographic images of different stages of BPD. FIG. 16B shows alveolar injury in mouse models.

Figure 17:
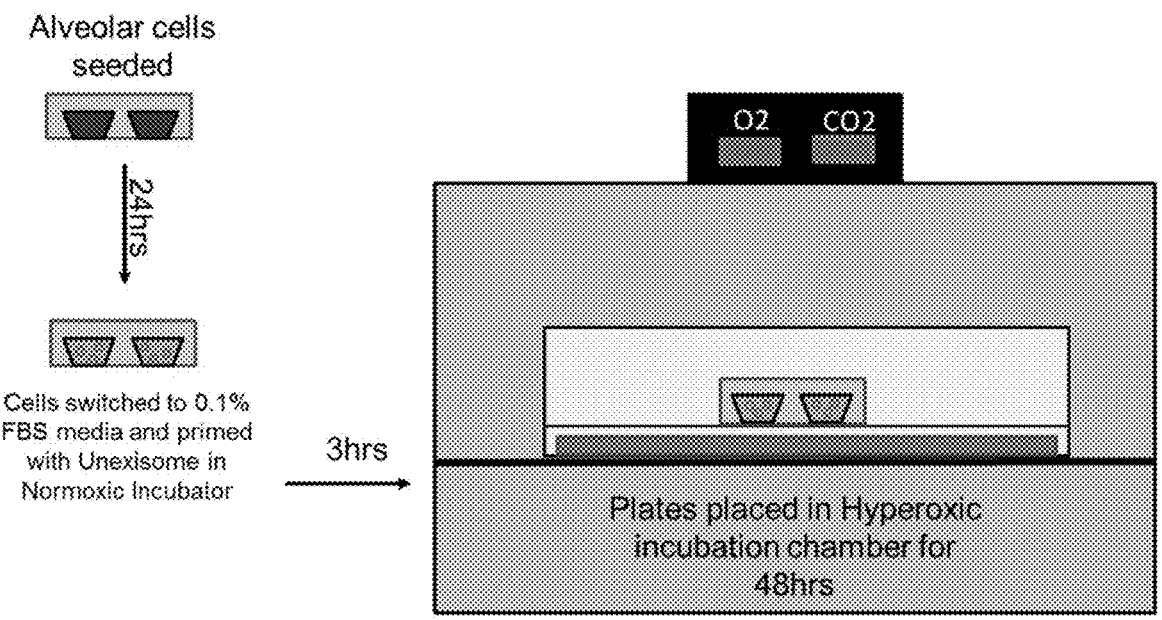

FIG. 17 shows hyperoxic in vitro model as well as unexisome-mediated inflammatory suppression. Alveolar cells were seeded for 24 hours, and switched to 0.1% FBS media and primed with a potent population of exosomes (unexisome) in normoxic incubator for 3 hours, and plated in hyperoxic incubation chamber for 48 hours.

FIG. 18 shows that a potent population of exosomes (unexisome) increases immunomodulatory capacity based on decreased IL-6 expression in cells exposed to hyperoxic stress (hyperoxia causes IL-6 release). "#" Denotes significance of exosome treatment compared to normoxia control. "*" Denotes significance of exosome treatment compared to hyperoxia control.

FIG. 19 shows that a potent population of exosomes (unexisome) increases immunomodulatory capacity based on reduced TNFα expression in cells exposed to hyperoxic stress (hyperoxia causes TNFα release). "*" Denotes significance of exosome treatment compared to hyperoxia control.

FIG. 20 shows that a potent population of exosomes (unexisome) have anti-apoptosis effect under hyperoxia, as indicated by increased absorbance, corresponding to increased number of cells. "*" Denotes significance of exosome treatment compared to hyperoxia control.

FIG. 21 shows that a potent population of exosomes (unexisome) reduces cytochrome C release from cells exposed to hyperoxic stress, corresponding to decreased cellular apoptosis. * Denotes significance of exosome treatment compared to hyperoxia control.

Figure 22A:
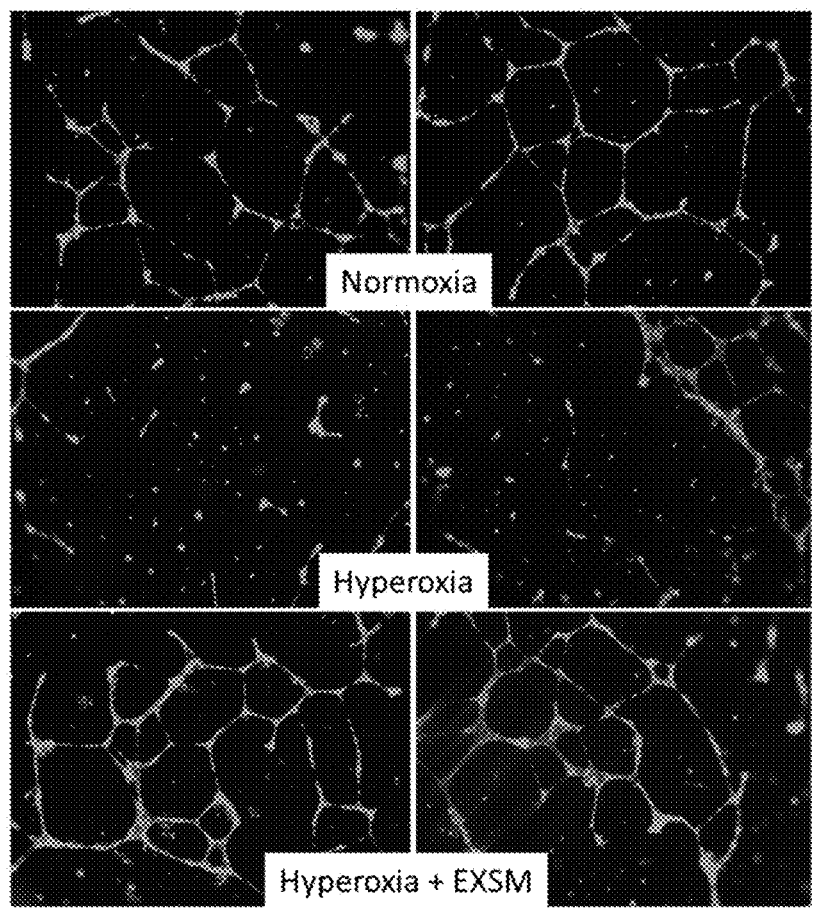
Figure 22B:
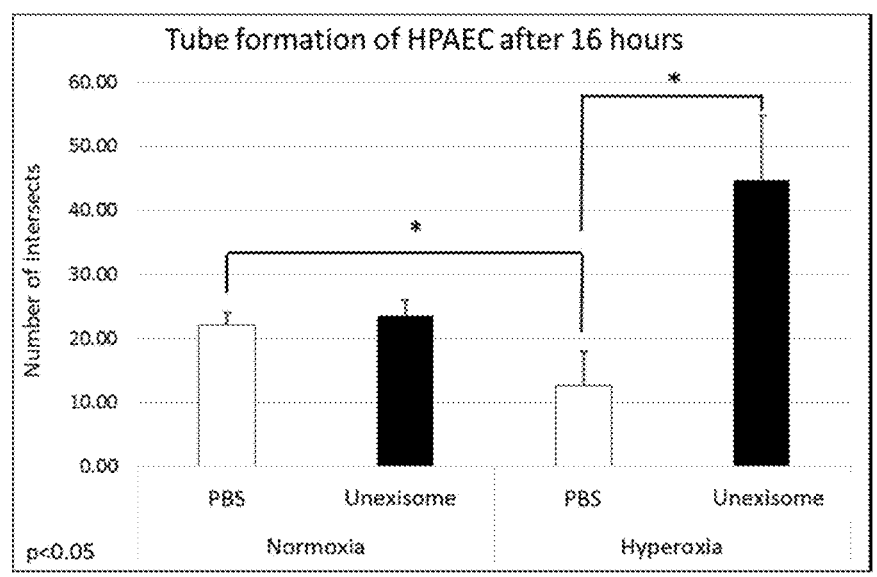

FIG. 22A shows fluorescent image of normoxia cells, cells exposed to hyperoxic stress, and cells treated with potent exosomes. FIG. 22B shows that exosomes (COM2) treatment restore tube formation in hyperoxia.

Figure 23:
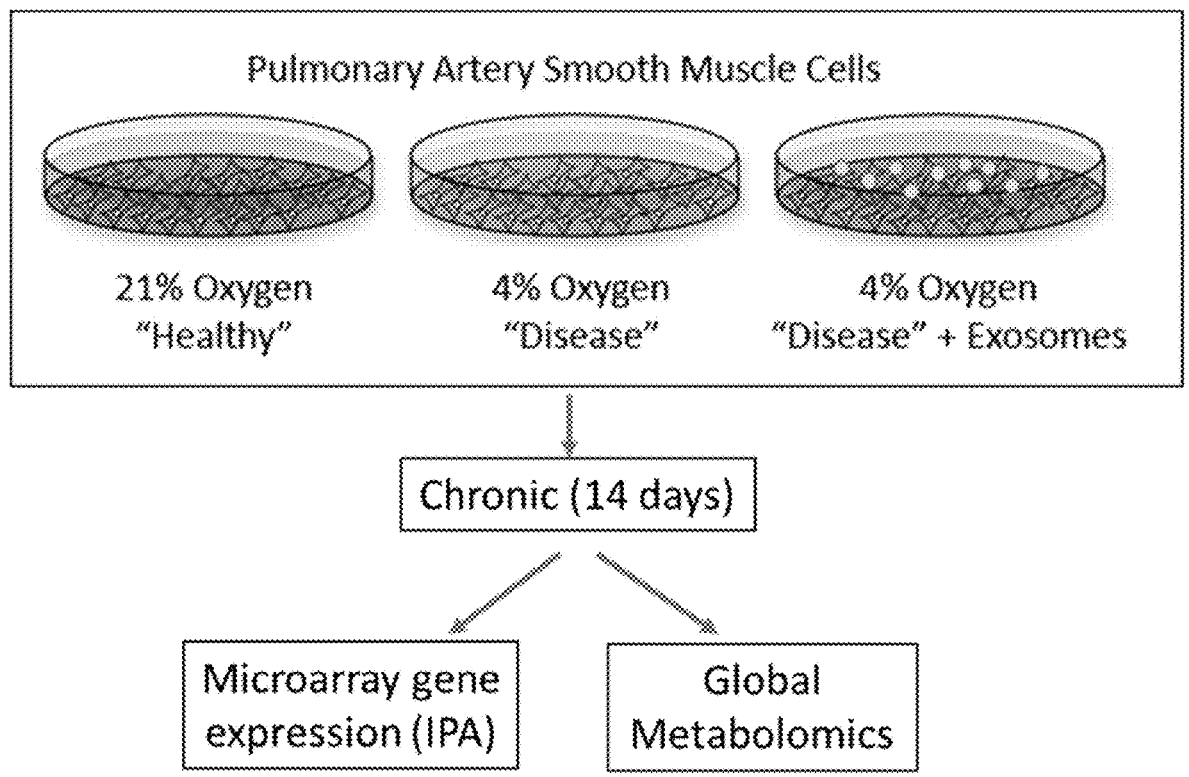

FIG. 23 shows schematics of smooth muscle cells (SMC) chronic hypoxia model. SMC switch to a proliferative, non-apoptotic phenotype in PAH and hypoxia, leads to thickening of the vessels and arteries in the lungs, causing higher pressures and ultimately damages to the heart/negative symptoms in PAH. SMCs were cultured at normoxia, 4% oxygen, and 4% oxygen with exosomes. During the culturing period, the cells were treated twice a week for two weeks with potent exosomes. The resulting SMCs were analyzed by microarray gene expression (IPA) and/or global metabolomics.

Figure 24:
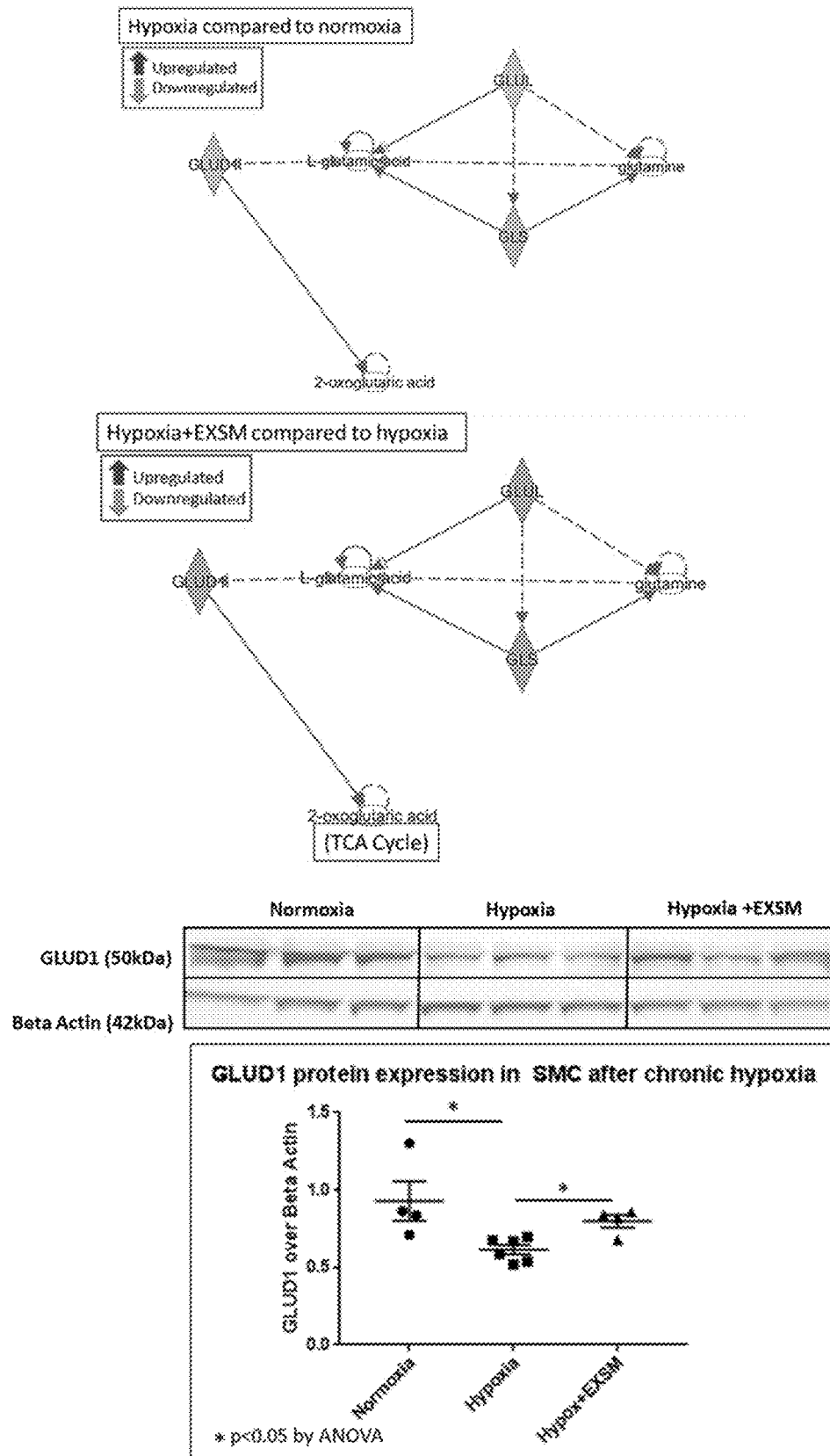

FIG. 24 shows that exosomes upregulate GLUD1 gene expression in chronic hypoxia.

Figure 25:
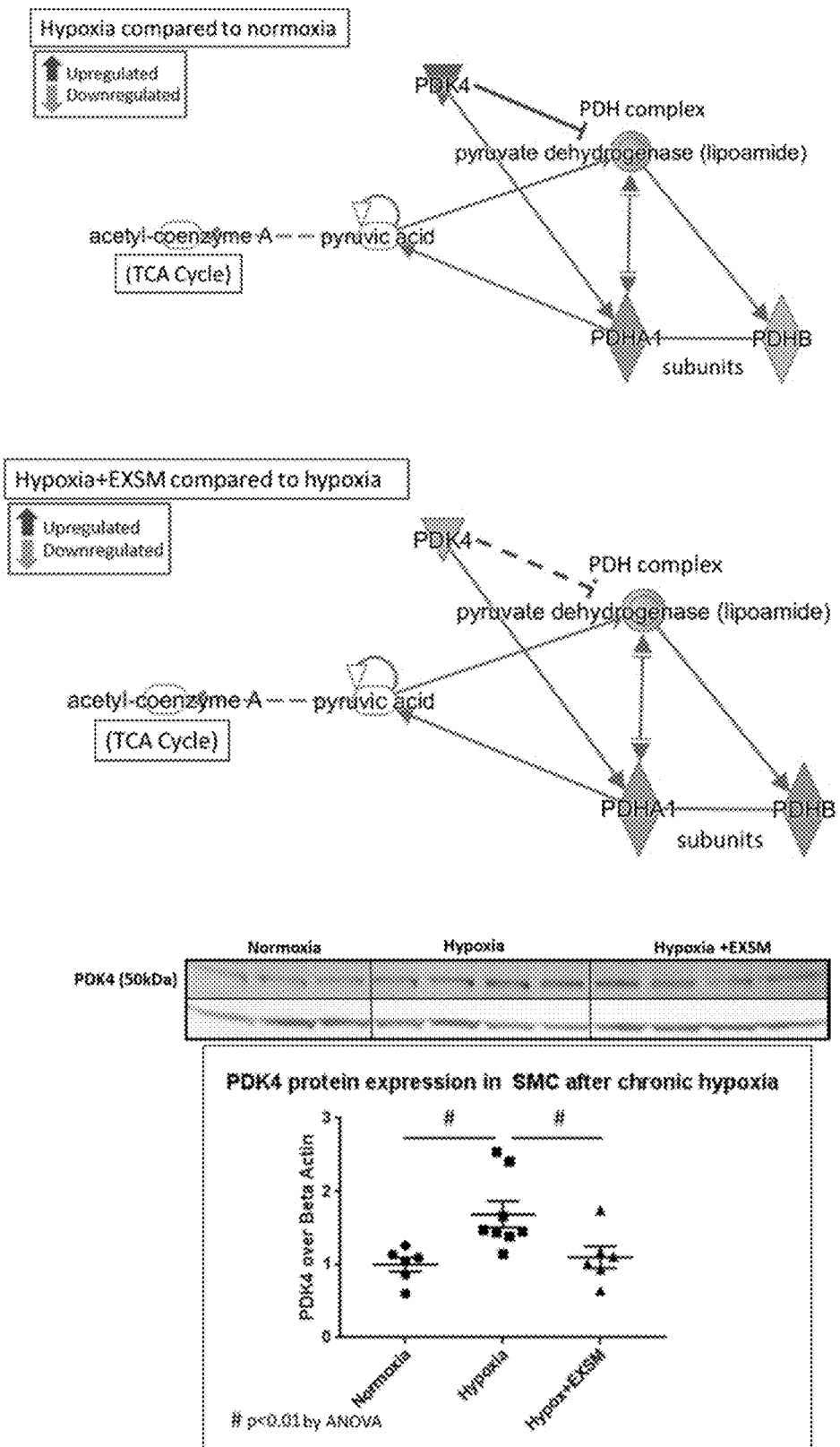

FIG. 25 shows that exosomes downregulate PDK4 in chronic hypoxia.

Figure 26:
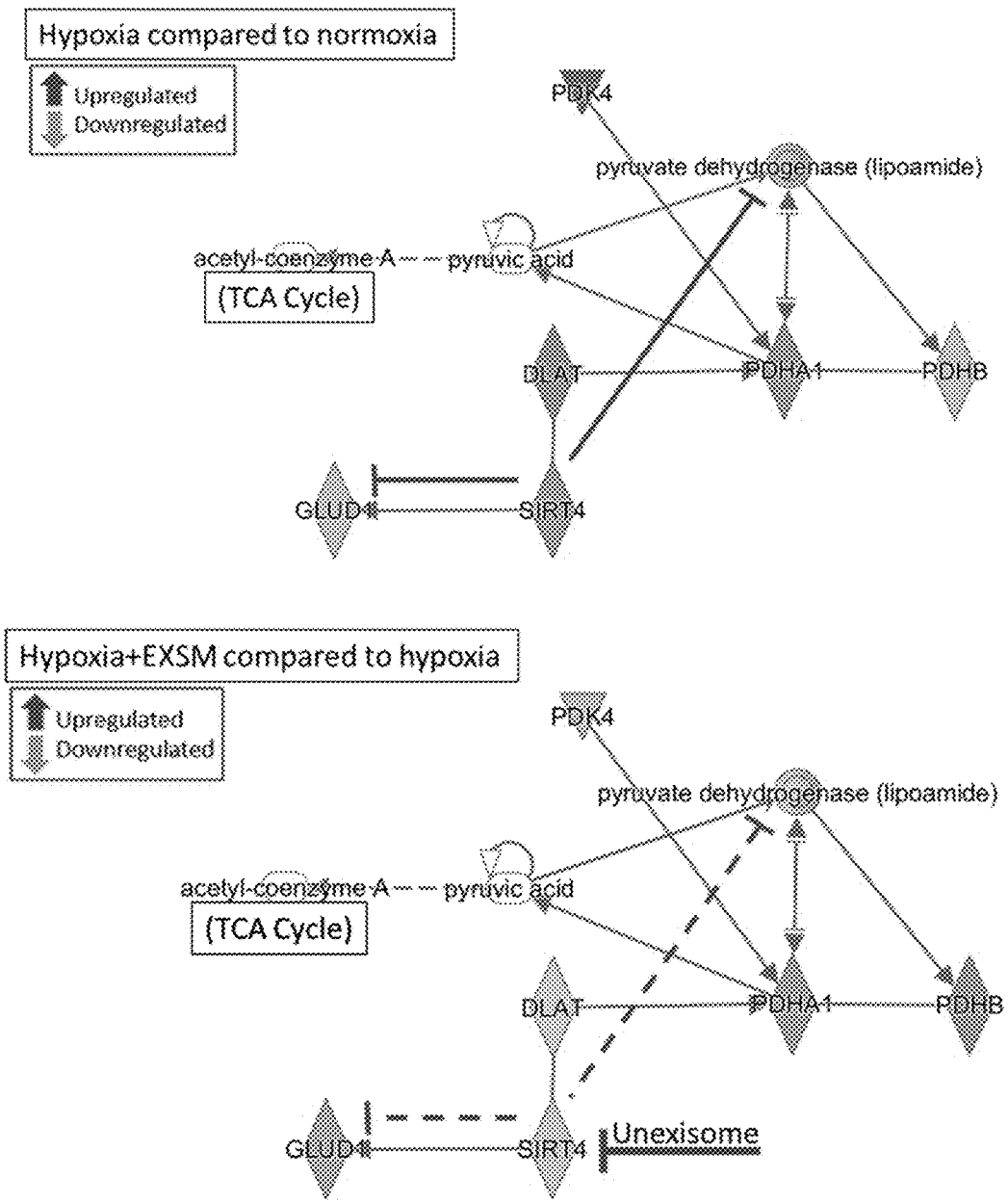

FIG. 26 shows that exosomes downregulate SIRT4 in chronic hypoxia. SIRT4 gene inhibits 2 metabolic enzymes, GLUD1 and PDH, in an in vitro PAH model. SIRT4 gene is downregulated by exosome treatment in vitro PAH model, while GLUD1 and PDH are upregulated by exosome treatment. SIRT4 is believed to be a target for exosome treatment.

Figure 27:
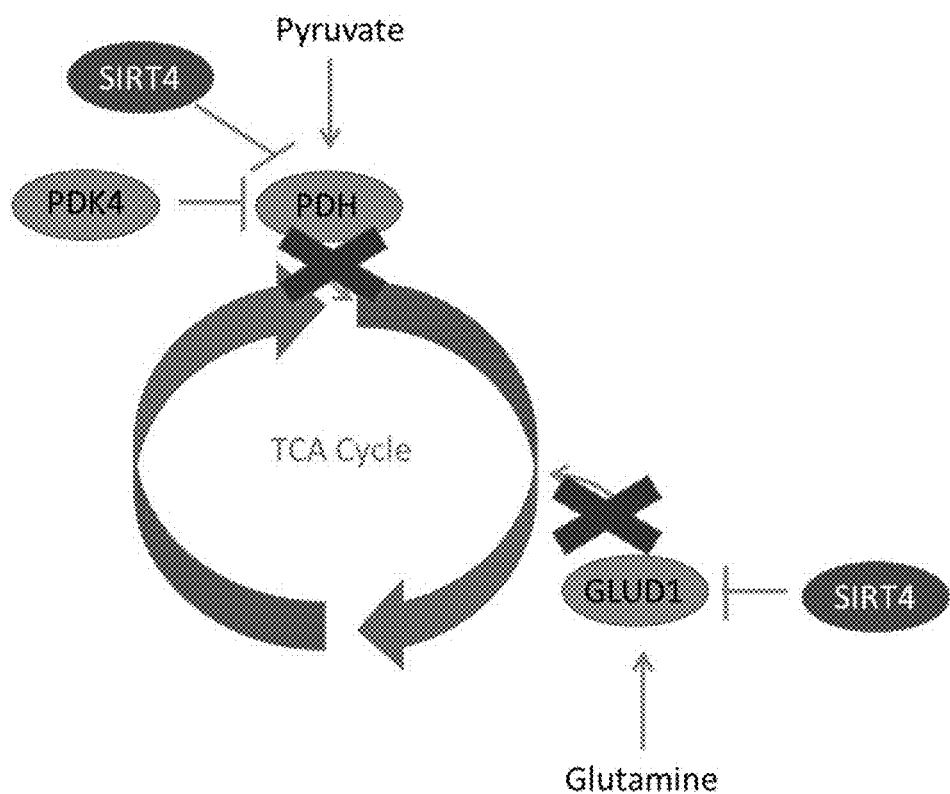

FIG. 27 shows proposed mechanism of potent exosomes in restoring TCA cycle. In particular, hypoxia inhibits TCA cycle function by (1) upregulating SIRT4 and PDK4, which both inhibit PDH and therefore pyruvate entry into the TCA cycle (2) upregulating SIRT4, which inhibits GLUD1 and therefore glutamine entry into the TCA cycle. Potent exosomes (unexisomes) decrease both SIRT4 and PDK4, thereby increasing glutamine and pyruvate flux into the TCA cycle.

Figure 28:
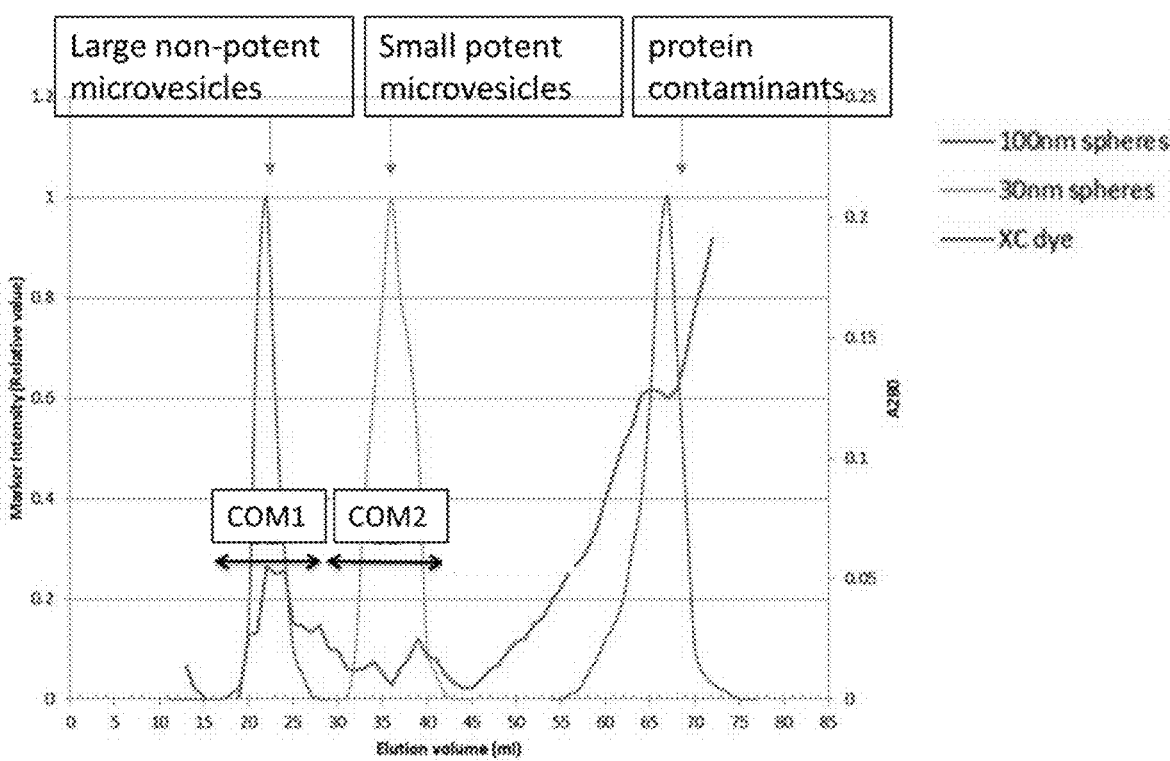

FIG. 28 shows isolation of the potent population of exosomes (COM2) using size exclusion chromatography, compared to ultra-centrifugation or gradient separation which isolate not only exosomes of non-ideal size but also protein and non-potent microvesicles contaminants.

FIG. 29 shows TEM imaging of exosomes. The results show that the isolated potent exosomes have more homogenous size and clearer image compared to ultracentrifuged samples.

Figure 30:
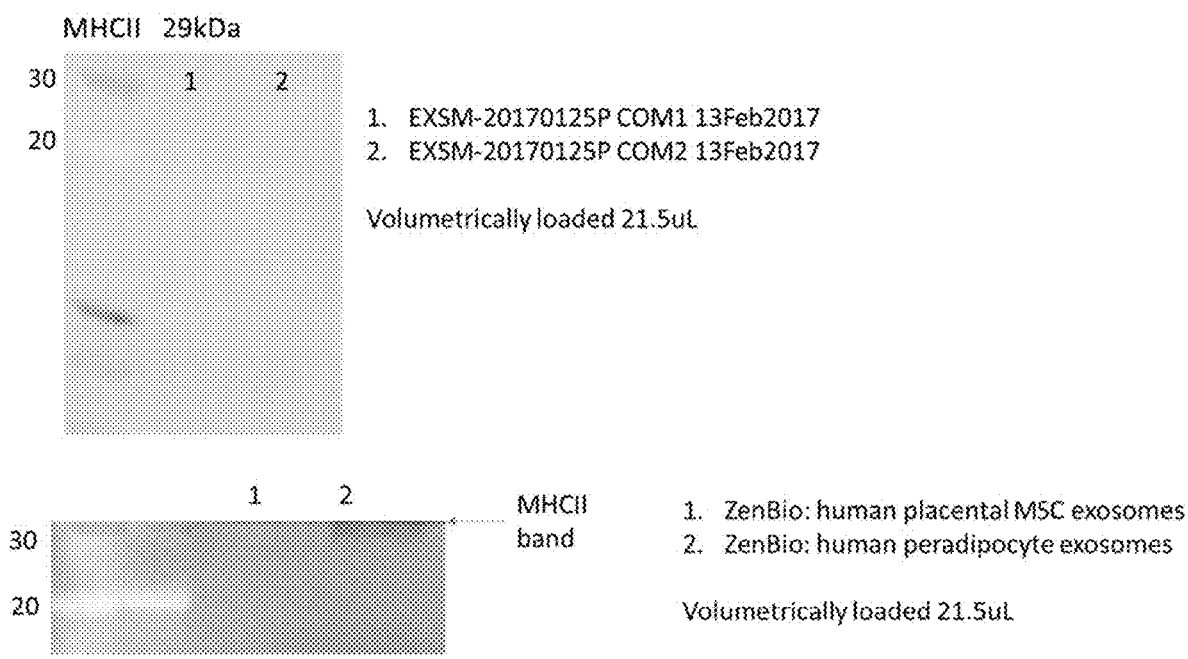

FIG. 30 shows that the isolated potent exosomes are free of MHCII contamination. In contrast, commercially available exosomes from ZenBio contain MHCII contamination.

FIGS. 31A-31B show that the isolated potent exosomes are free of fibronectin and other protein contaminations based on ponceau staining. FIG. 31A shows that the isolated exosomes are free of contaminating protein fibronectin, while ZenBio commercially available ultracentrifuged preparation have fibronectin contamination. FIG. 31B shows that the exosome isolated by ultracentrifugation contained fibronectin contamination as did concentrated cell culture media. The exosomes isolated by size exclusion chromatograph are free of fibronectin contaminant as well as other protein contaminant capable of being stained by ponceau.

Figure 32:
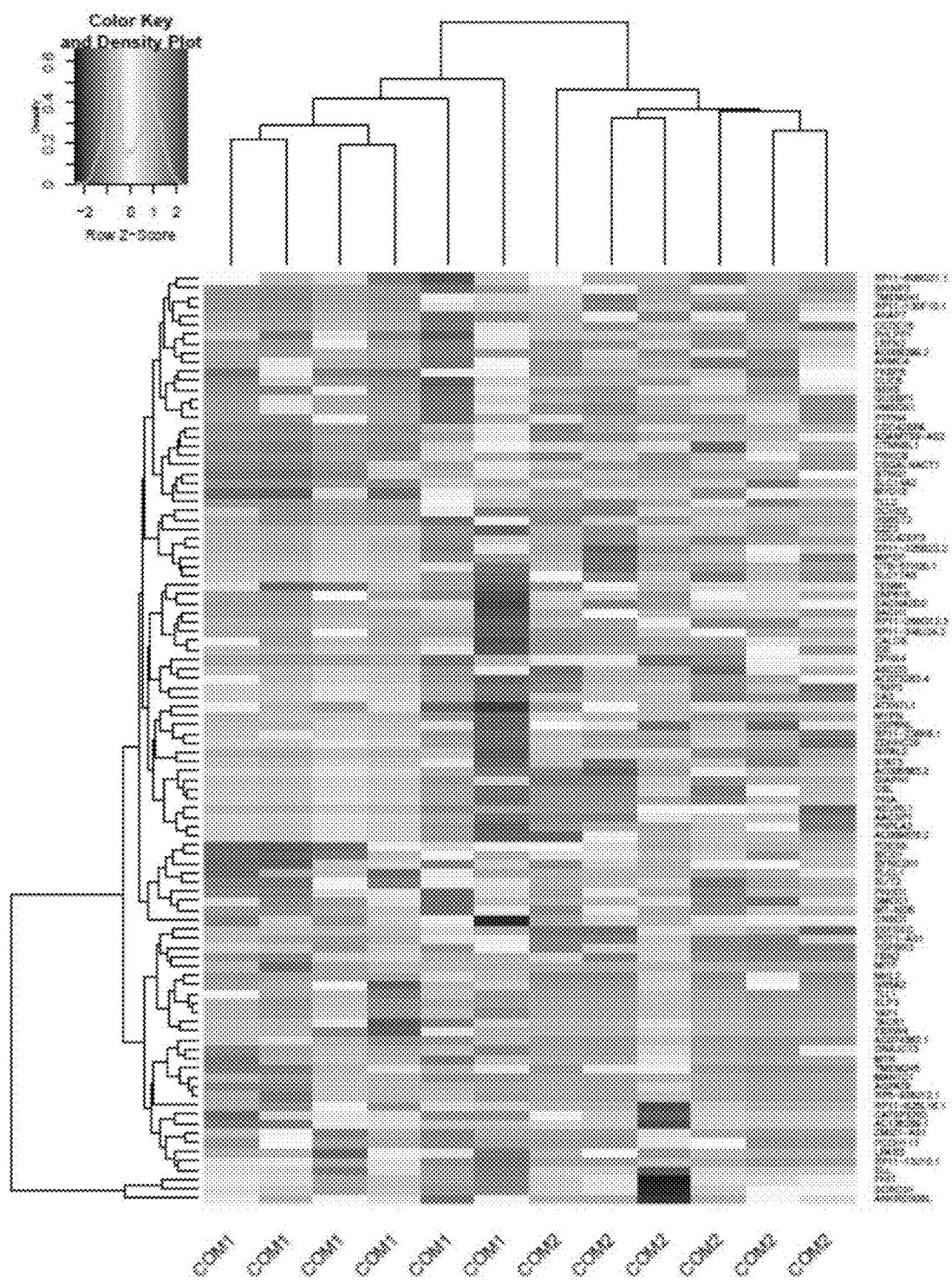

FIG. 32 shows RNAseq clustering analysis of the potent population and contaminant microvesicles. The results show that that the potent exosomes (COM2) are differentially clustering from contaminating microvesicles. They are enriched in SORCS1, FHIT and ANKRD30BL.

Figure 33:
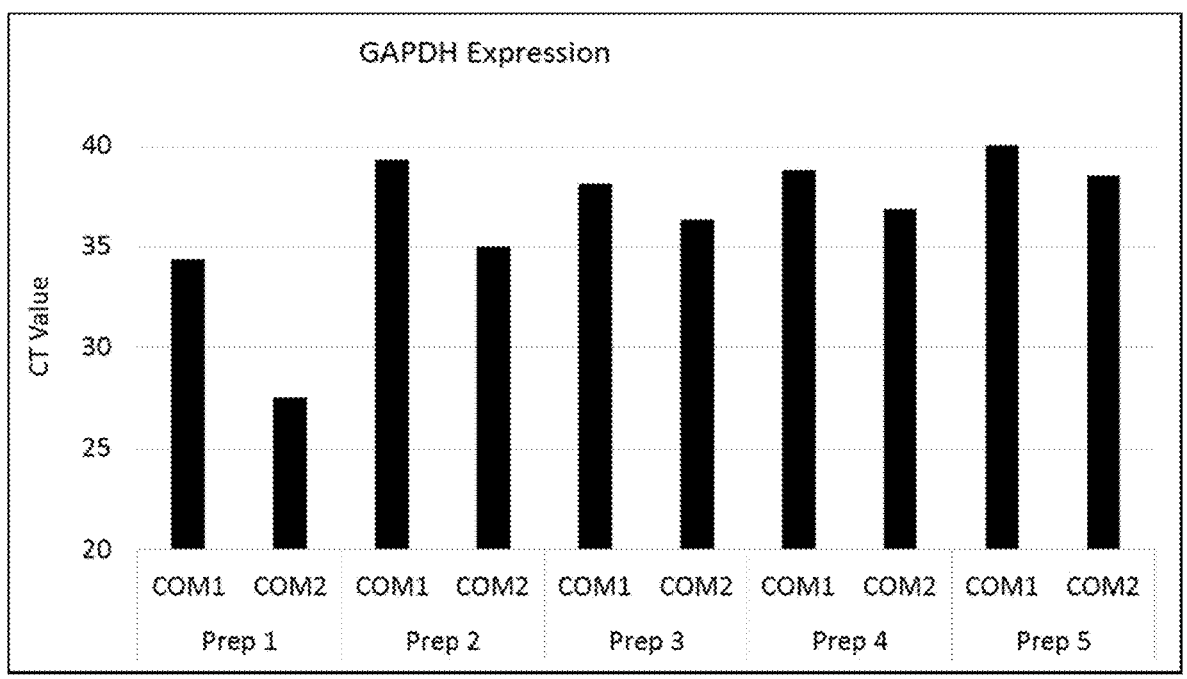

FIG. 33 shows GAPDH expression in potent exosomes (COM2) versus non-potent exosomes (COM1). The results show that potent exosomes have a lower CT value, corresponding to higher expression level of GAPDH.

Figure 34:
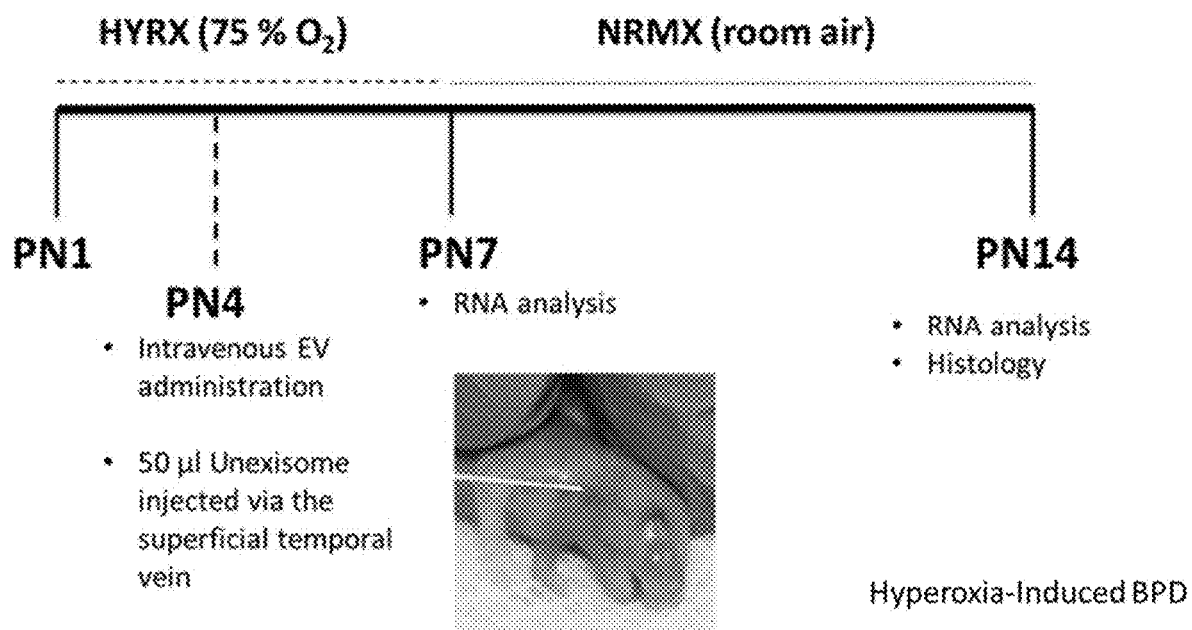

FIG. 34 shows the procedure of in vivo study of treating BPD mouse model with potent exosomes (Unexisome).

Figure 35A:
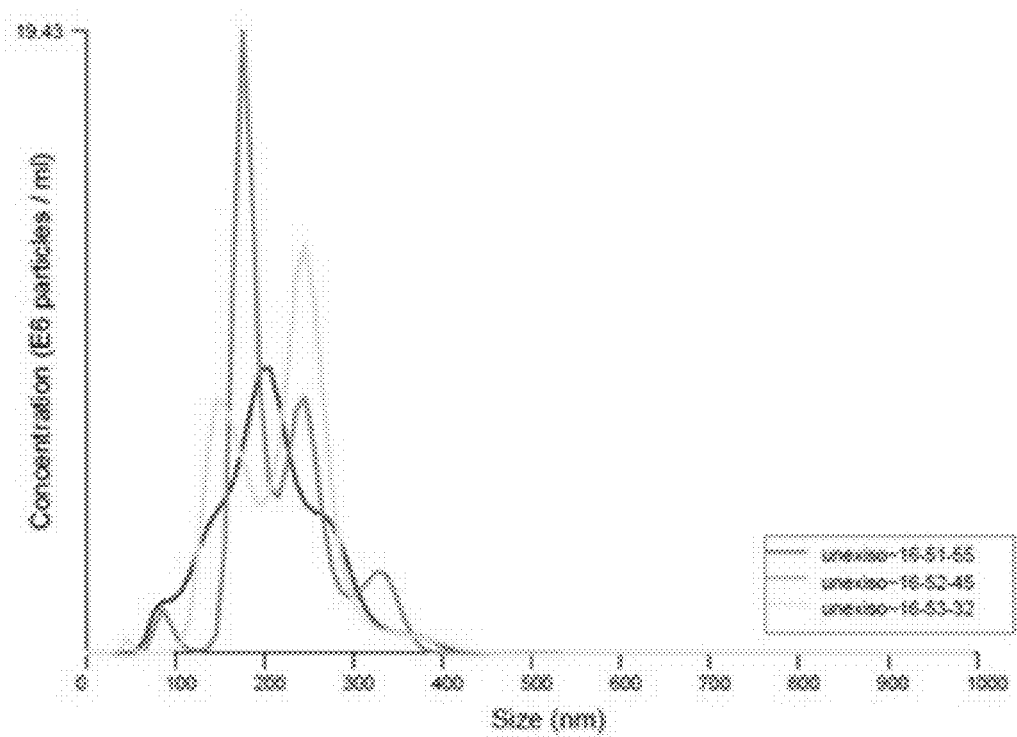
Figure 35B:
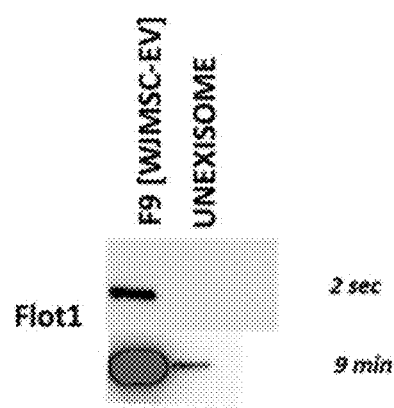
Figure 35C:
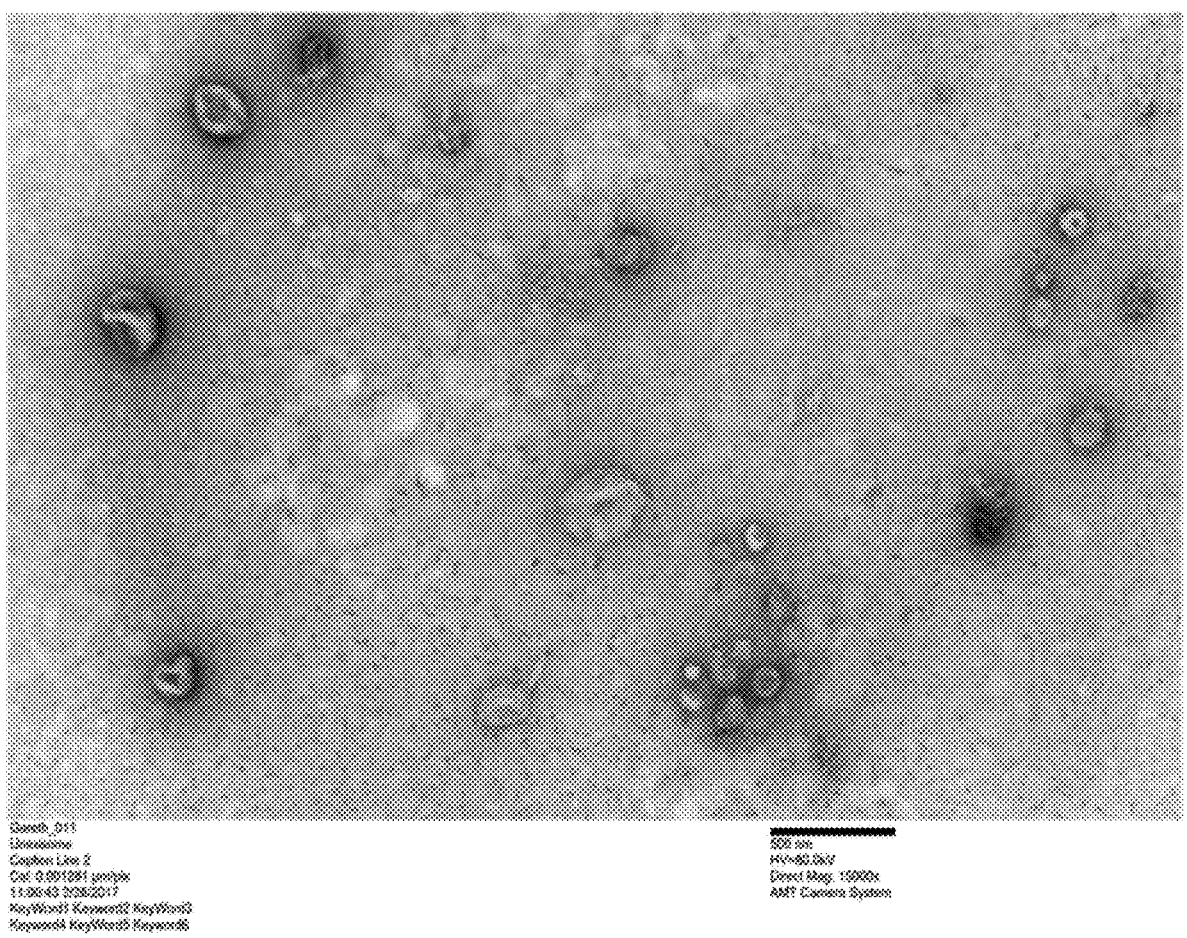

FIGS. 35A-35C show characterization of exosomes used in the in vivo study. FIG. 35A shows the concentration of exosomes is $1.2 \times 10^8$ particles/mL. FIG. 35B shows that FLOT1 is present in exosomes based on Western blot analysis. FIG. 35C shows representative TEM imaging of exosomes.

Figures 36A, 36B:
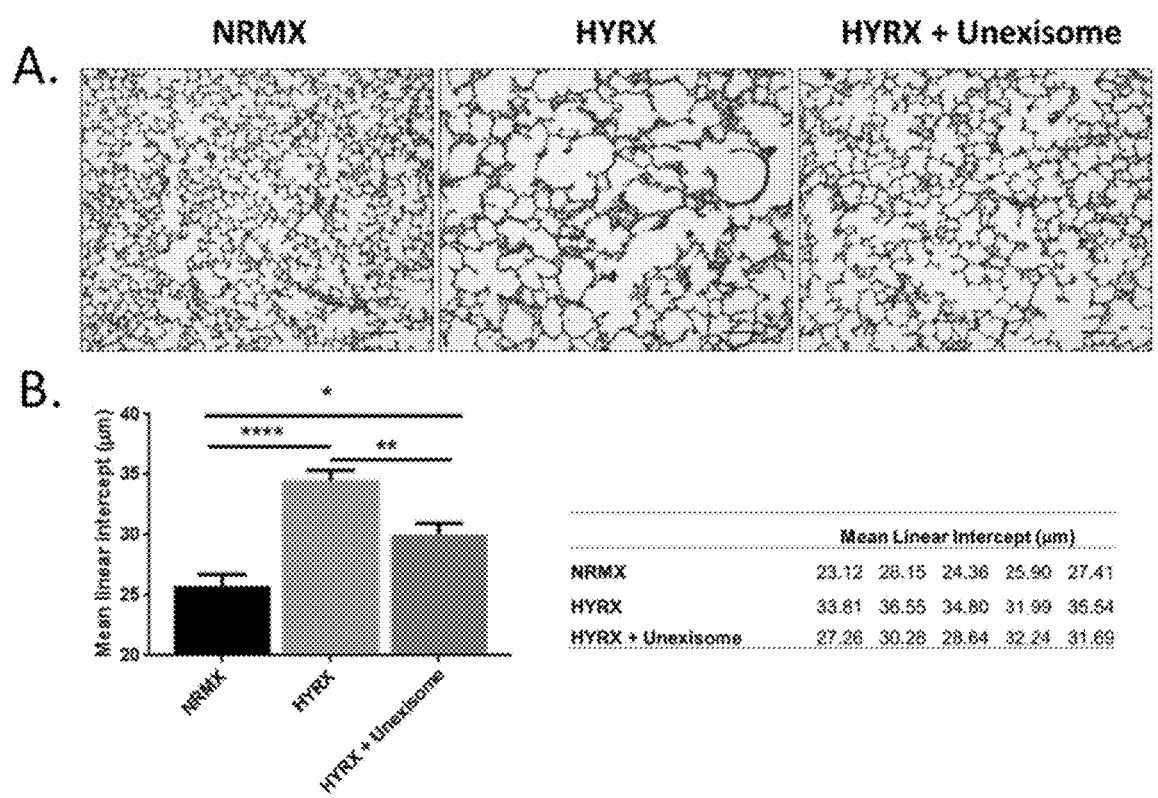

FIGS. 36A-36B show that exosomes rescued BPD-associated alveolar simplification. FIG. 36A shows that treatment with potent exosomes rescues the hyperoxia (HYRX)-mediated increase in alveolar simplification compared to normoxia (NRMX). FIG. 36B shows quantification of mean liner intercept, which represents a surrogate of average air space diameter.

Figure 37:
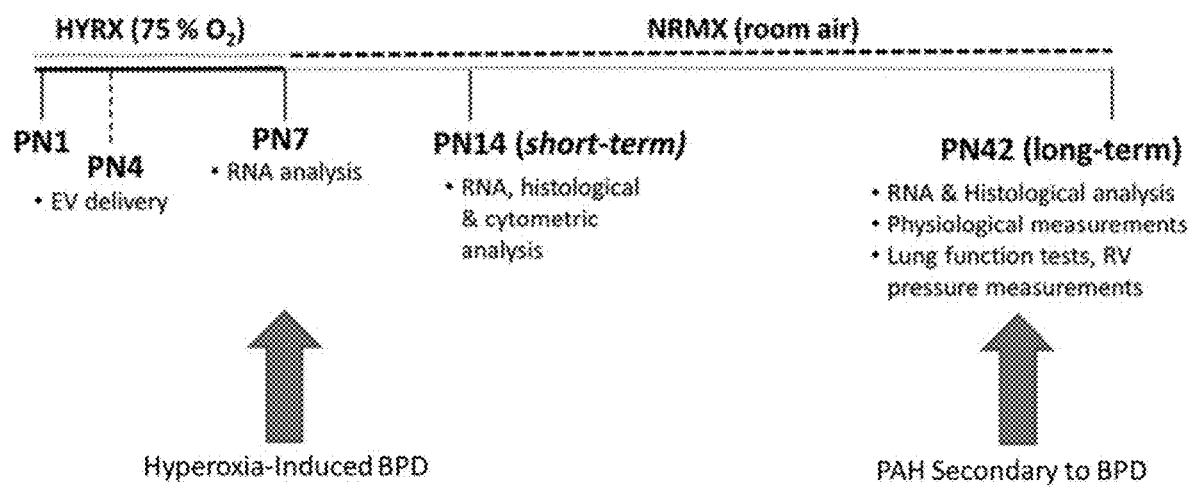

FIG. 37 shows the procedure for in vivo study of treating BPD-induced PAH mouse model of PAH secondary to BPD with potent exosomes (Unexisome).

Figure 38A:
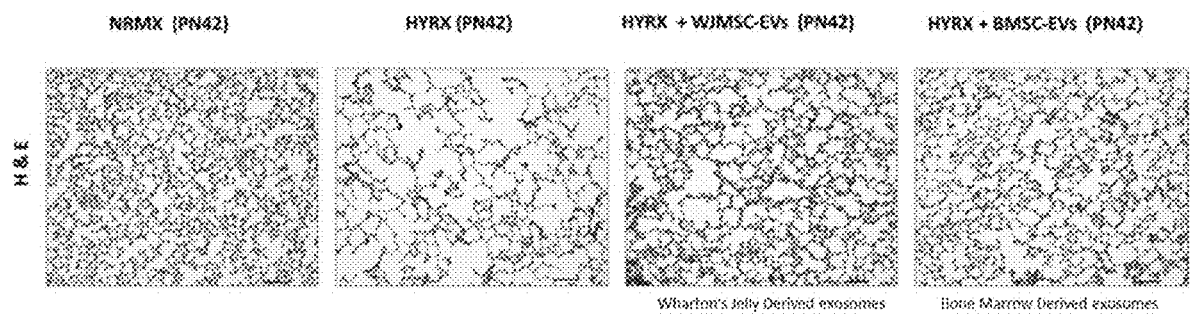
Figure 38B:
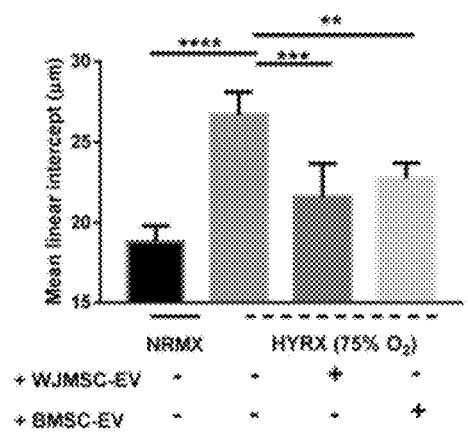
Figure 38C:
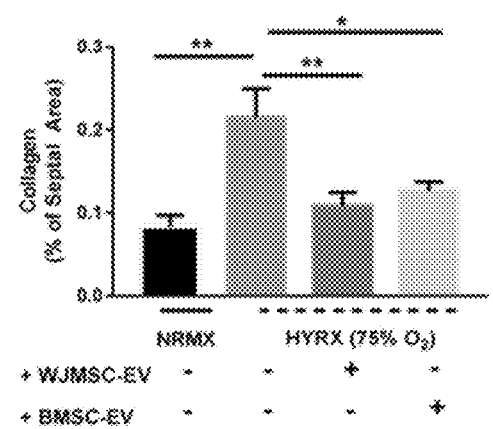

FIGS. 38A-38C show that exosomes rescued chronic alveolar simplification. FIG. 38A shows the images of cells under normoxia, hypoxia, and cells treated with Wharton's jelly derived exosomes, and bone marrow derived exosomes. FIG. 38B shows that exosomes rescued alveolar simplification in BPD-associated PAH mouse model. FIG. 38C shows that exosomes reduced modest lung fibrosis as shown by collagen deposition in the septal area in BPD-associated PAH mouse model.

Figure 39A:
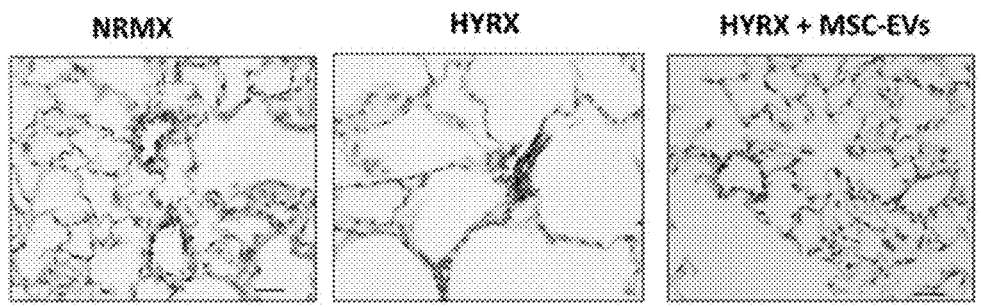
Figure 39B:
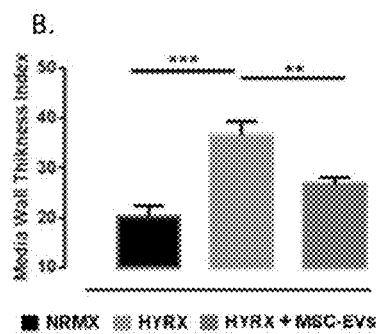
Figure 39C:
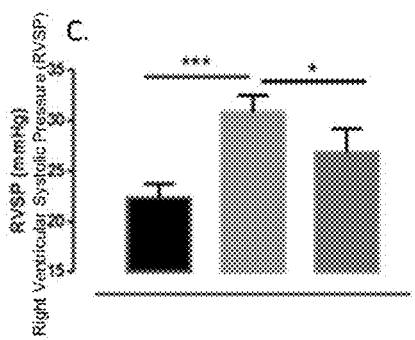
Figure 39D:
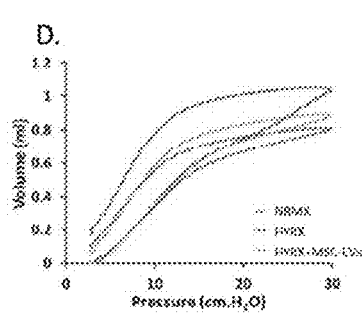

FIGS. 39A-39D show that exosomes rescued PAH pulmonary vascular remodeling demonstrated by α-smooth muscle actin stain (FIG. 39A and FIG. 39B) and pressure changes associated with PAH (FIG. 39C). PV-loops demonstrate a significant shift in hyperoxia (HYRX) mice, indicative of emphysema-like features of lung disease and air trapping when compared to normoxia (NRMX) controls. Exosomes showed a significant rescue in this shift, indicative of improved lung function.

Figure 40A:
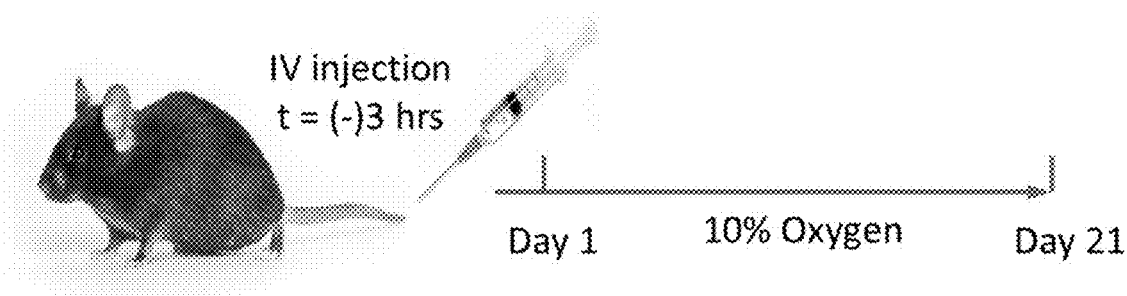

FIG. 40A shows the procedure for in vivo study of treating hypoxia-induced PAH mouse model.

Figure 40B:
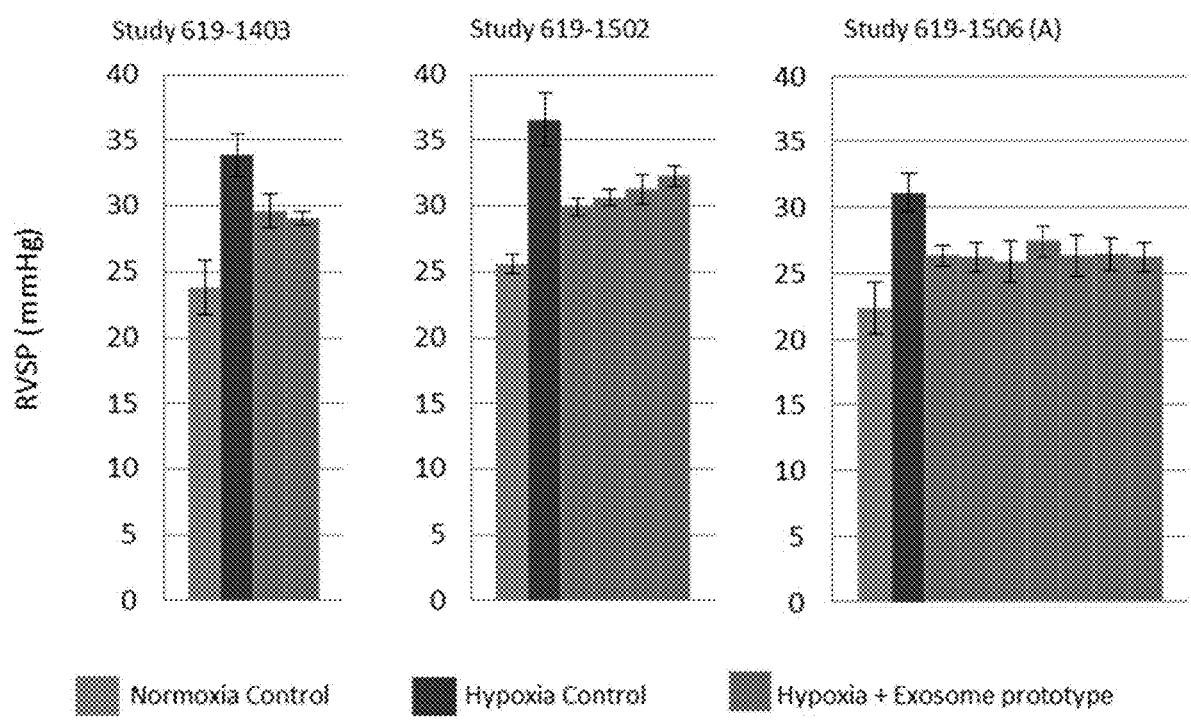

FIG. 40B shows that MSC exosomes prevent PAH in mice.

FIG. 41A shows the procedure of in vivo study of treating Sugen (VEGF receptor agonist) and hypoxia-induced PAH mouse model with a combination of exosomes and sildenafil. FIG. 41B shows that the combination therapy of exosome and sildenafil reversed PAH in mouse model.

FIG. 42 shows the procedure for identification of exosome-mediated mechanism of action in PAH.

Figure 43:
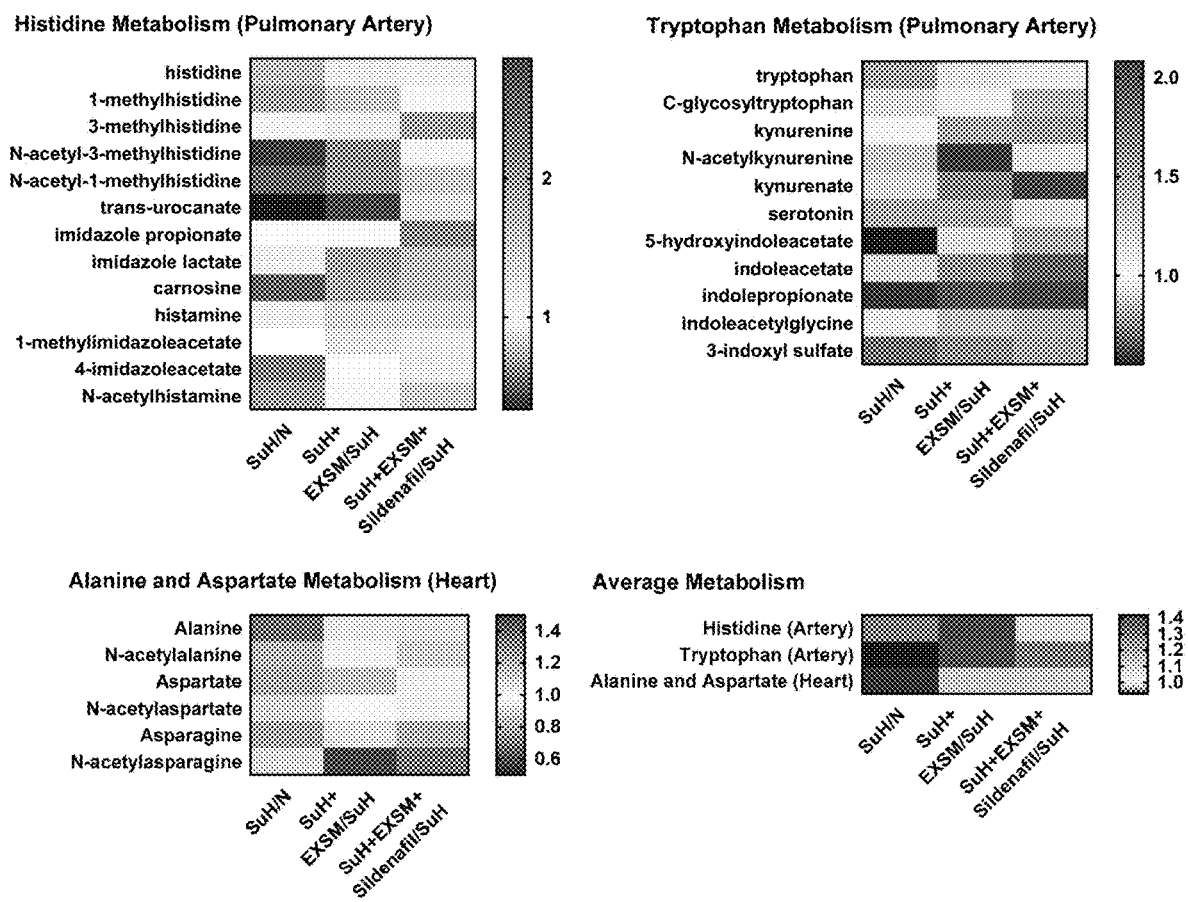

FIG. 43 shows that exosomes upregulate amino acid metabolism in Sugen/hypoxia model of PAH.

FIGS. 44A-44D. Isolated exosomes demonstrate expression of known exosome markers, 50-150 nm vesicle size, and metabolic gene and protein enrichment. FIG. 44A shows Western blot array of exosome proteins. FIG. 44B shows TEM imaging and FIG. 44C shows nanoparticle tracking for exosome size and concentration. FIG. 44D shows proteomic and RNAseq analysis demonstrated several proteins and genes involved in glycolysis, TCA cycle, and Electron transport chain enriched in exosomes.

Figure 45A:
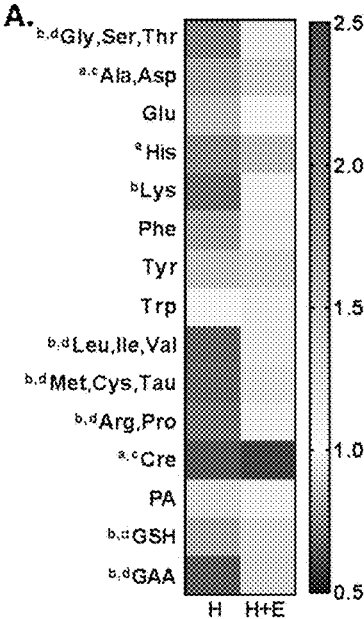
Figure 45B:
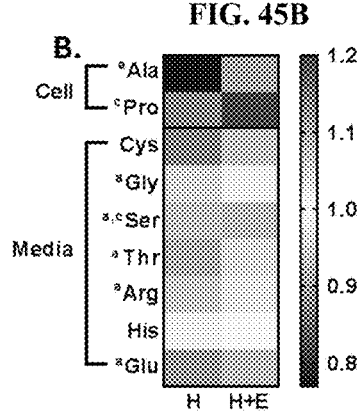
Figure 45C:
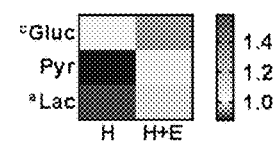
Figure 45D:
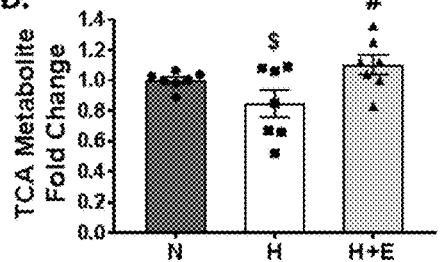
Figure 45E:
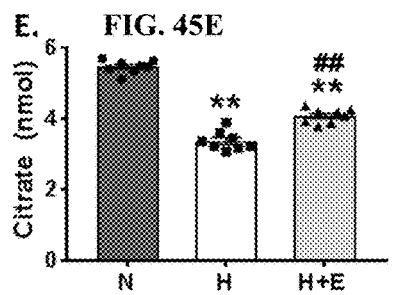
Figure 45F:
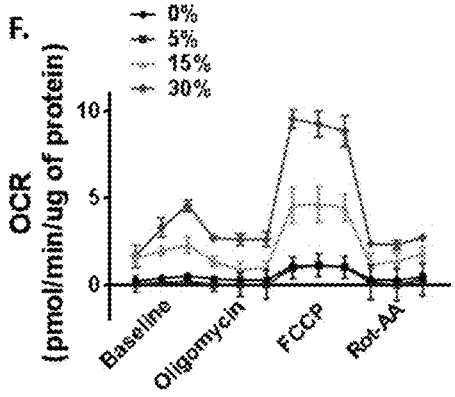
Figure 45G:
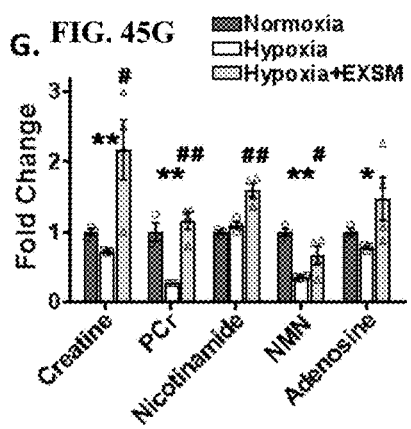
Figure 45H:
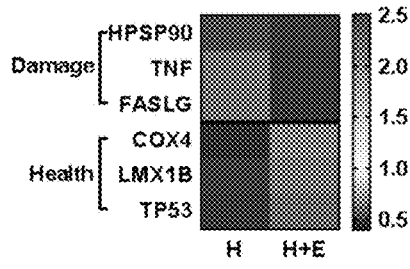
Figure 45I:
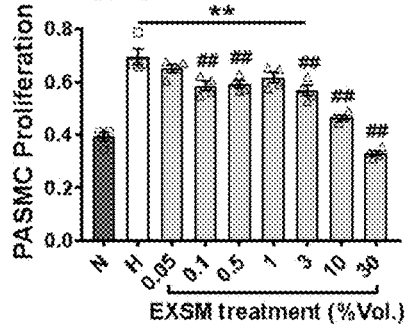

FIGS. 45A-45I. Exosomes increase global amino acid metabolism, boost mitochondrial efficiency, oxygen consumption rate, and energetics; while decreasing mitochondrial damage and proliferation in PASMC in chronic hypoxia. PASMC were cultured in normoxia or chronic hypoxia (4% oxygen for 2 weeks) and metabolite analysis of cell lysates was performed. FIG. 45A shows heat map analysis of amino acid (AA) metabolites. Data represented as mean±SEM of AA in each group. FIG. 45B shows heat map of amino acids present in cell culture supernatant after chronic hypoxia exposure. Amino acids were present in the cell growth media (media) or not (cell). FIG. 45C shows heat map of glucose (Glue), pyruvate (Pyr), and lactate (Lac) levels in PASMC cell culture supernatant after chronic hypoxia exposure. H denotes the fold change of hypoxia/normoxia and H+E denotes the fold change of hypoxia+exosome treatment/hypoxia. a, p<0.05 and b, p<0.01 represent hypoxia compared to normoxia treatments. c, p<0.05 and d, p<0.01 represent hypoxia+exosome treatment compared to hypoxia. FIG. 45D shows the average of TCA metabolites and FIG. 45E citrate alone in PASMC culture supernatant. FIG. 45F shows oxygen consumption rate (OCR) in PASMC after acute hypoxia exposure with increasing exosome treatment. Compounds oligomycin (1 µM), FCCP (4 µM), and a mix of rotenone and antimycin A (0.5 µM) were serially injected into all samples and background wells to measure ATP production, maximal respiration, and non-mitochondrial respiration, respectively. FIG. 45G shows creatine, phosphocreatine, nicotinamide, nicotinamide ribonucleotide, and adenosine in PASMC cell lysates. FIG. 45H shows heatmap of genes associated with mitochondrial damage (HPS90, TNF, and FASLG) and mitochondrial health/homeostasis (COX4, LMX1B, and TP53) in PASMC cell lysates. FIG. 45I shows PASMC proliferation after 4 days of normoxia or hypoxia exposure with increasing exosome treatment. $, p≤0.1 compared to normoxia. *, p≤0.05 and **, p≤0.01 represent hypoxia compared to normoxia treatments. #, p≤0.05 and ##, p≤0.01 represent hypoxia+exosome treatment compared to hypoxia.

Figure 46A:
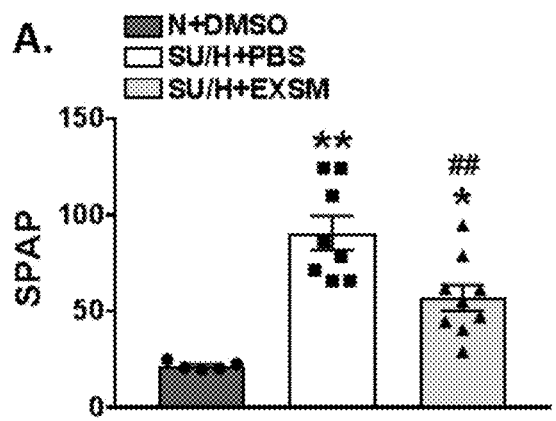
Figure 46B:
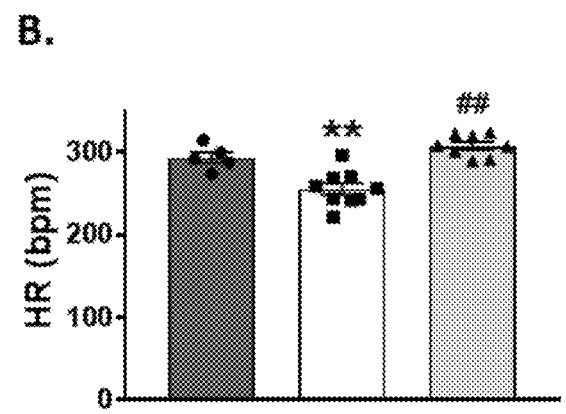
Figure 46C:
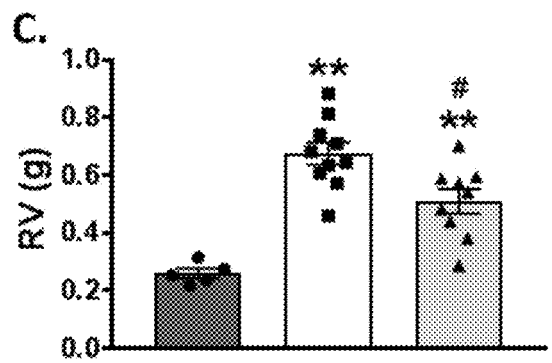
Figure 46D:
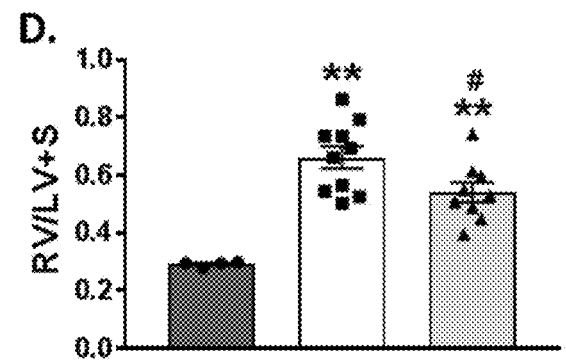

FIGS. 46A-46D. Exosome therapy improves PAH pathogenesis. FIG. 46A shows systolic pulmonary artery pressure (SPAP), FIG. 46B shows heart rate (HR), FIG. 46C shows right ventricle (RV) weight, and FIG. 46D shows right ventricle/left ventricle and septum (RV/LV+S) ratio was measured in a semaxinib/Hypoxia rat model of PAH. * p≤0.05 and **, p≤0.01 compared to N+DMSO. #, p≤0.05 and ##, p≤0.01 compared to SU/H+PBS. N+DMSO: normoxia+dimethyl sulfoxide, SU/H+PBS: semaxinib/Hypoxia+PBS, SU/H+EXSM: semaxinib/Hypoxia+exosome treatment under Sildenafil background.

Figure 47A:
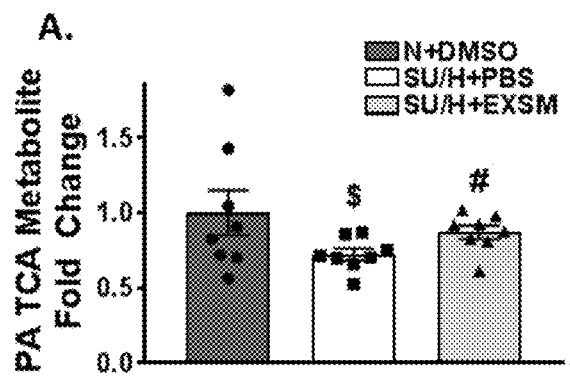
Figure 47B:
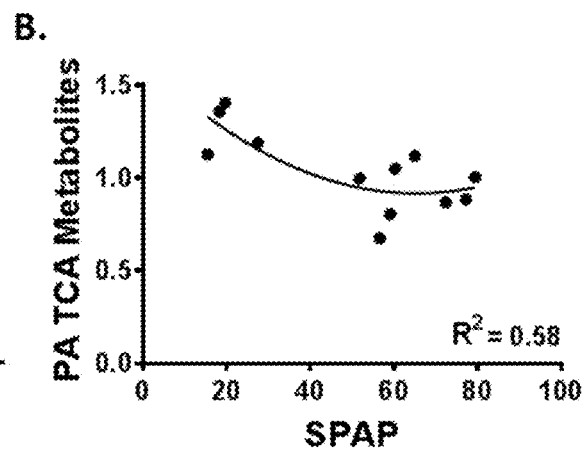
Figure 47C:
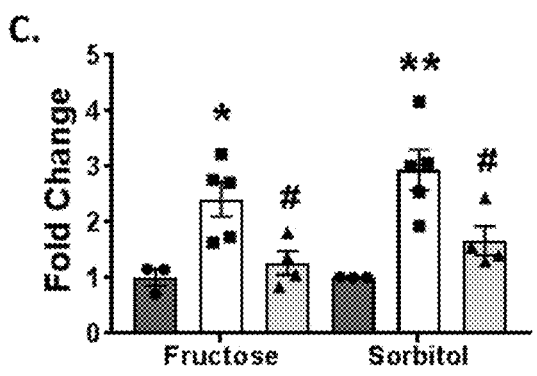
Figure 47D:
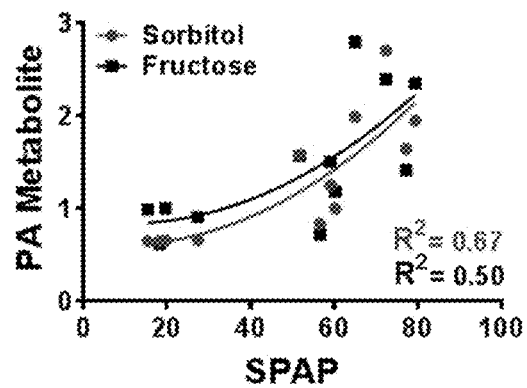
Figure 47E:
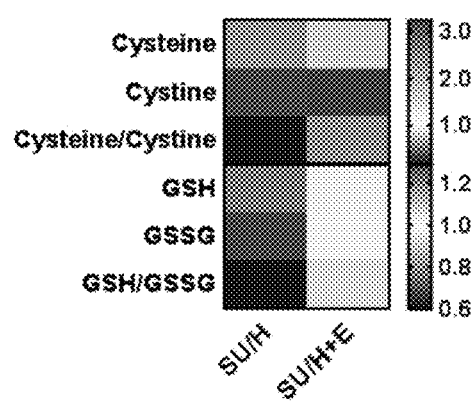
Figure 47F:
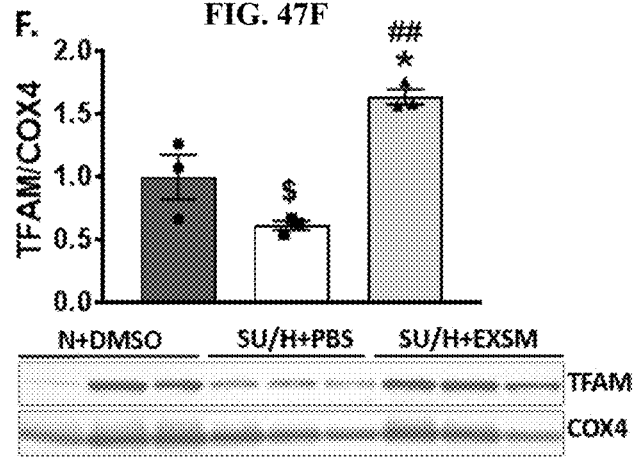

FIGS. 47A-47F: Exosome therapy ameliorates glucose oxidation, reactive oxygen species, and mitochondrial damage in a semaxinib/hypoxia rat model of PAH. FIG. 47A shows average of TCA cycle metabolites; FIG. 47C fructose and sorbitol; and FIG. 47E cysteine/cysteine ratio and glutathione (GSH)/glutathione disulfide (GSSG) ratio in the pulmonary artery (PA) of rats was measured. SPAP correlated to PA TCA cycle metabolites (FIG. 47B) and fructose and sorbitol (FIG. 47D). FIG. 47F shows mitochondrial TFAM protein expression in rat gastrocnemius. SU/H denotes the fold change of control/PAH and SU/H+E denotes the fold change of exosome treated PAH/PAH. Control (N+DMSO), PAH (SU/H+PBS), and PAH after exosome treatment (SU/H+EXSM). $, $p \leq 0.1$ compared to N+DMSO. *, $p \leq 0.05$ and **, $p \leq 0.01$ compared to N+DMSO. #, $p \leq 0.05$ and ##, $p \leq 0.01$ compared to SU/H+PBS. N+DMSO: normoxia+dimethyl sulfoxide, SU/H+PBS: semaxanib/hypoxia+PBS, SU/H+EXSM: semaxanib/hypoxia+exosome treatment.

Figure 48:
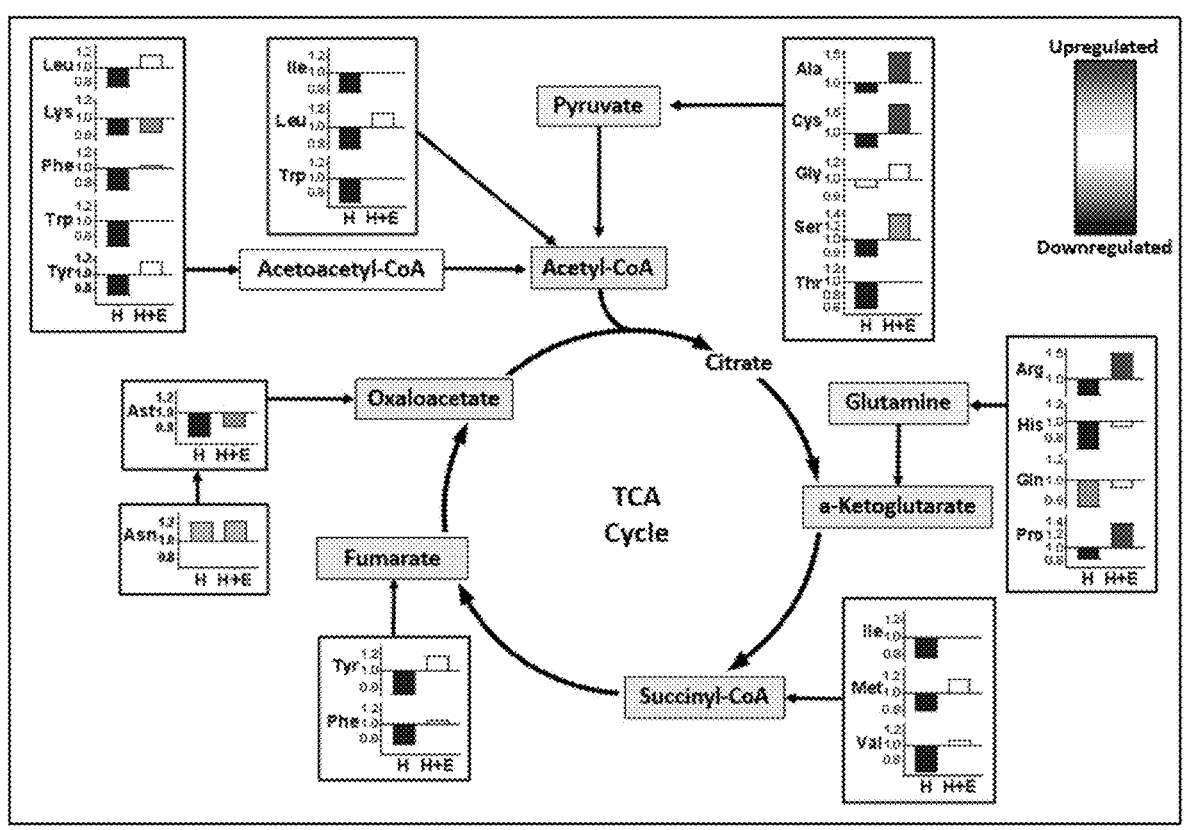

FIG. 48. Exosomes pre-treatment increases amino acid metabolites in PASMC after chronic hypoxia exposure through PDH and GLUD1 entry points of the TCA cycle. PASMC were cultured in normoxia or chronic hypoxia (4% oxygen for 2 weeks) and metabolite analysis of cell lysates was performed. TCA cycle metabolite levels. H denotes the fold change of hypoxia/normoxia and H+E denotes the fold change of hypoxia+exosome treatment/hypoxia. Dark blue: $p \leq 0.05$ downregulation of hypoxia compared to normoxia. Red: $p \leq 0.05$ upregulation of hypoxia+exosome treatment compared to hypoxia.

Figure 49A:
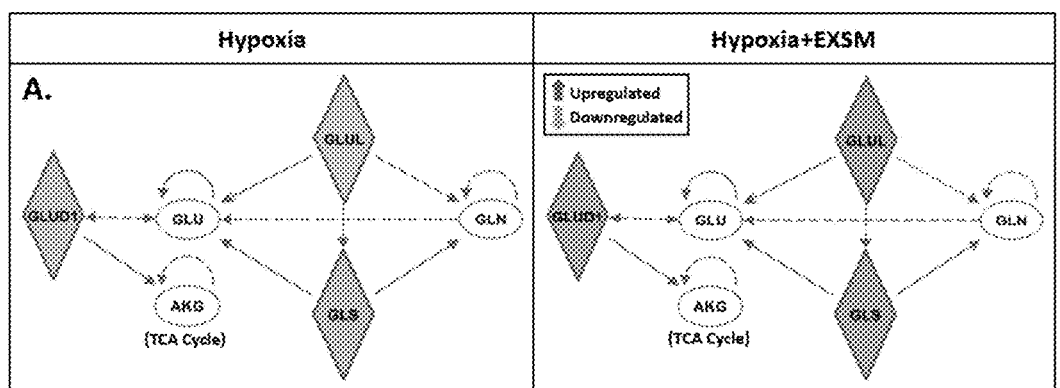
Figure 49B:
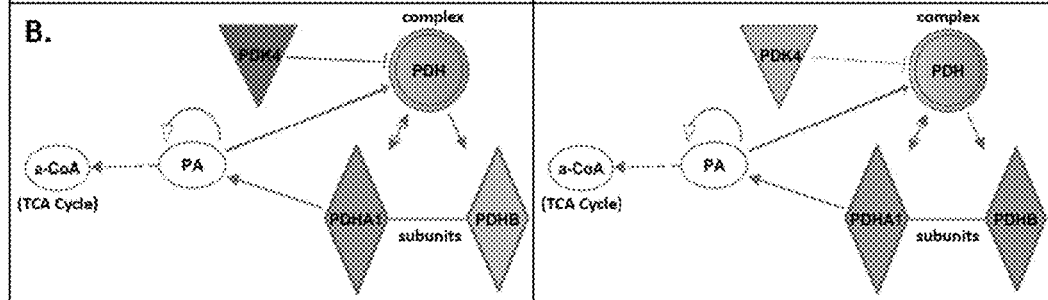

FIGS. 49A-49B. Exosome pre-treatment upregulates PDH and GLUD1 gene expression in PASMC after chronic hypoxia. PASMCs cultured in normoxia or chronic hypoxia (4% oxygen for 2 weeks) were analyzed via microarray analysis. FIG. 49A shows GLUD1 and FIG. 49B shows PDH pathway gene expression was assessed. Left panels represent the hypoxia/normoxia fold change while right panels represent the hypoxia+exosome treatment/hypoxia fold change. Red denotes upregulation and green denotes downregulation of gene expression. GLUD1: glutamate dehydrogenase, GLU: L-glutamic acid, AKG: 2-oxoglutaric acid, GLUL: glutamine synthetase, GLS: glutaminase, GLN: glutamine. a-CoA: acetyl-coenzyme A, PA: pyruvic acid, PDK4: pyruvate dehydrogenase kinase 4, PDHA1: pyruvate dehydrogenase subunit alpha 1, PDHB: pyruvate dehydrogenase subunit beta, PDH: pyruvate dehydrogenase complex.

FIGS. 50A-50F. Exosome pre-treatment increases GLUD1 and PDH but decreases PDK4 protein expression in chronic hypoxia. PASMC were cultured in normoxia or chronic hypoxia (4% oxygen for 2 weeks) with and without exosome treatment (10% volume). FIG. 50A shows GLUD1, FIG. 50B shows PDH and FIG. 50C shows PDK4 protein expression. PASMC cultured in normoxia or chronic hypoxia with increasing exosome doses of 1.25%, 5%, and 10% volume. FIG. 50D shows GLUD1, FIG. 50E shows PDH and FIG. 50F shows PDK4 protein expression. *, $p \leq 0.05$ and **, $p \leq 0.01$ represent hypoxia compared to normoxia treatments. #, $p \leq 0.05$ and ##, $p \leq 0.01$ represent hypoxia+exosome treatment compared to hypoxia. N: normoxia, H: hypoxia, H+E: hypoxia with exosome treatment.

FIGS. 51A-51C. Exosome treatment downregulates SIRT4 gene expression of PASMCs in chronic hypoxia. PASMC were cultured in normoxia or chronic hypoxia (4% oxygen for 2 weeks). FIG. 51A shows global microarray analysis on the SIRT4 pathway was performed (n=4 per group). Left panels represent the hypoxia/normoxia fold change while right panels represent the hypoxia+exosome treatment/hypoxia fold change. Red denotes upregulation and green denotes downregulation. FIG. 51B shows SIRT4 gene expression in PASMCs over time in hypoxia after exosome treatment (10% volume). D: days in hypoxia. FIG. 51C shows SIRT4 gene expression after increasing doses of exosome treatments. GLUD1: glutamate dehydrogenase, SIRT4: sirtuin 4, DLAT: dihydrolipoamide acetyltransferase component of pyruvate dehydrogenase, a-CoA: acetyl-coenzyme A, PA: pyruvic acid, PDK4: pyruvate dehydrogenase kinase 4, PDHA1: pyruvate dehydrogenase subunit alpha 1, PDHB: pyruvate dehydrogenase subunit beta, PDH: pyruvate dehydrogenase complex. * $p \leq 0.05$ and **, $p \leq 0.01$ represent hypoxia compared to normoxia treatments. #, $p \leq 0.05$ and ##, $p \leq 0.01$ represent hypoxia+exosome treatment compared to hypoxia. N: normoxia, H: hypoxia.

Figure 52:
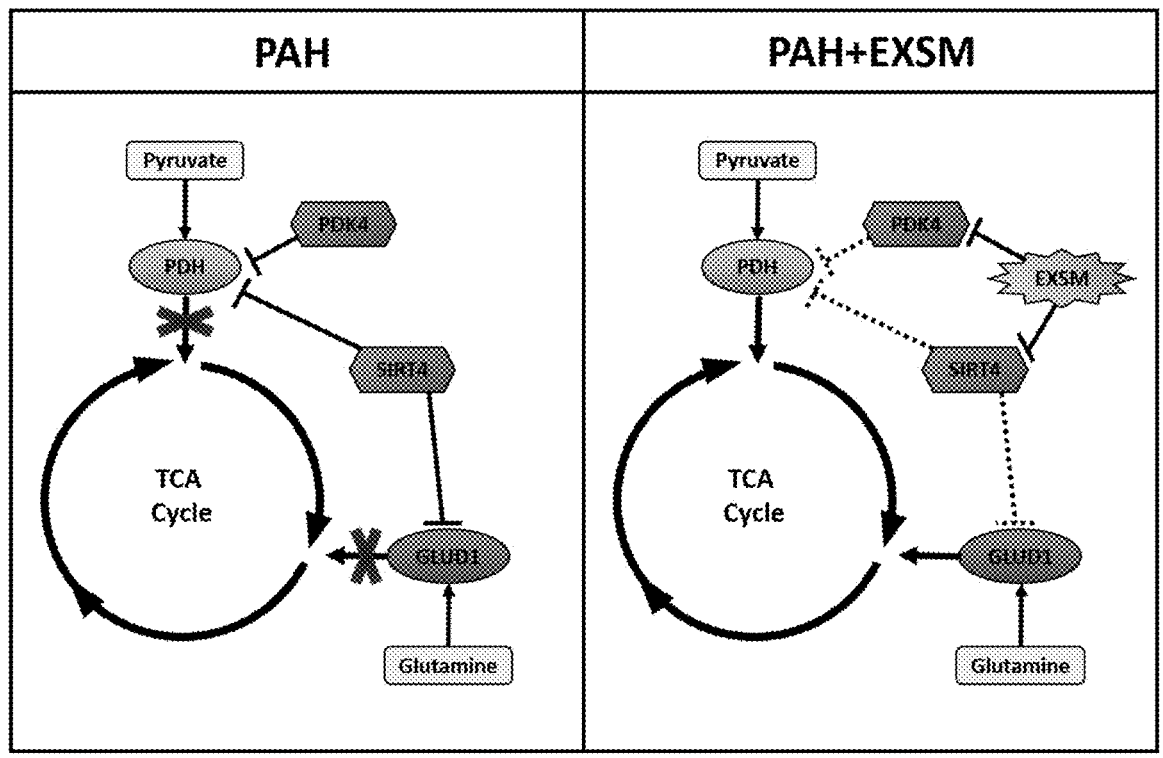

FIG. 52. Proposed exosome mechanism of action targets SIRT4 in PAH: Chronic hypoxia in PASCM inhibits TCA cycle function by upregulating SIRT4, which inhibits PDH and GLUD1 and limits pyruvate and glutamine entry into the TCA cycle (left panel). Exosome treatment downregulates SIRT4, thereby increasing glutamine and pyruvate flux into the TCA cycle (right panel).

Figure 53A:
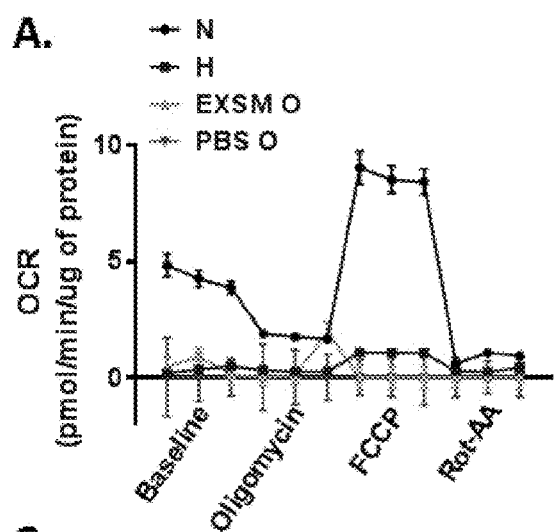
Figure 53B:
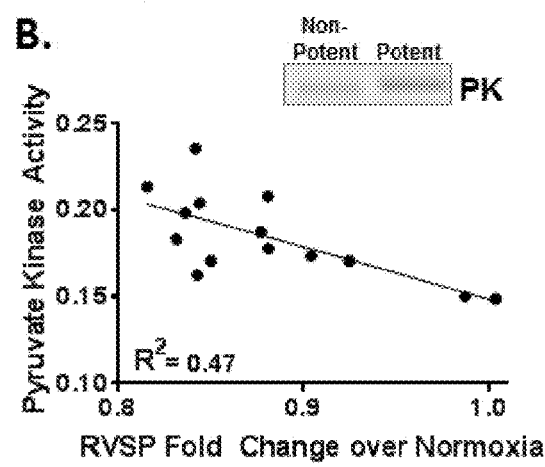
Figure 53C:
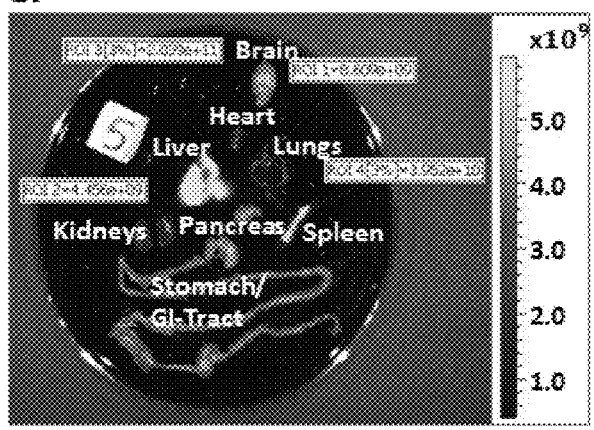
Figure 53D:
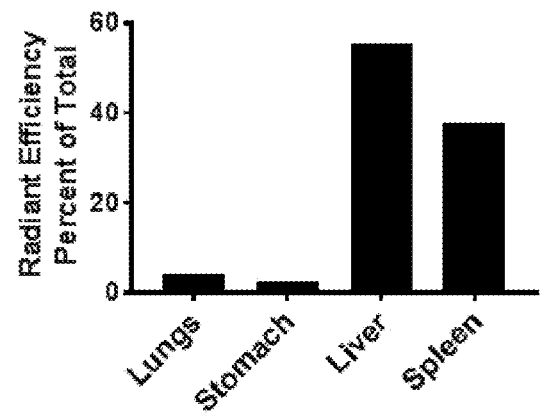

FIG. 53A-53D. Exosome oxygen consumption rate and pyruvate kinase content. FIG. 53A shows oxygen consumption rate (OCR) in PASMC after 24 hr in normoxia (N), hypoxia (H), or in exosomes without cells (EXSM 0) and PBS without cells (PBS 0). FIG. 53B shows pyruvate kinase protein expression in different exosome batches. FIG. 53C shows bio-distribution data. FIG. 53D shows radiant efficiency (percent of total) bio-distribution for lung, stomach, liver and spleen.

FIGS. 54A-54D. Exosome therapy ameliorates PAH in a mouse and rat model. FIG. 54A shows right ventricular systolic pressure (RVSP) and FIG. 54B shows right ventricle/left ventricle and septum (RV/LV+S) ratio was measured in a hypoxia-induced mouse model of PAH. FIG. 54C shows systolic pulmonary artery pressure (SPAP) and FIG. 54D shows right ventricle/left ventricle and septum (RV/LV+S) ratio was measured in a semaxinib/Hypoxia rat model of PAH with Sildenafil as a background therapy. **, $p \leq 0.01$ compared to normoxia and N+DMSO. +, $p \leq 0.1$; #, $p \leq 0.05$; and ##, $p \leq 0.01$ compared to hypoxia and SU/H+PBS. ^, $p \leq 0.05$ and ^^, $p \leq 0.01$ compared to SU/H+Sildenafil. N+DMSO: normoxia+dimethyl sulfoxide, SU/H+PBS: semaxinib/Hypoxia+PBS, SU/H+Sildenafil: semaxinib/Hypoxia+Sildenafil, SU/H+EXSM: semaxinib/Hypoxia+exosome treatment, SU/H+EXSM+Sildenafil: semaxinib/Hypoxia+exosome treatment+Sildenafil FIGS. 55A-55D. Exosome and Sildenafil combination therapy ameliorates systolic pulmonary artery pressure (SPAP), glucose oxidation, and reactive oxygen species effects in a Sugen/Hypoxia rat model of PAH. FIG. 55A shows SPAP, FIG. 55B shows average of TCA metabolites, FIG. 55C shows fructose and sorbitol, and FIG. 55D shows glutathione (GSH), glutathione disulfide (GSSG) and the GSH/GSSG ratio in the pulmonary artery of rats was measured. Control (N+DMSO), PAH (SU/H+PSB), PAH after exosome treatment (SU/H+EXSM), and PAH after combination Sildenafil+exosome therapy (SU/H+EXSM+Sildenafil). * $p \leq 0.05$ and **, $p \leq 0.01$ compared to N+DMSO. #, $p \leq 0.05$ and ##, $p \leq 0.01$ compared to SU/H+PBS. N+DMSO: normoxia+dimethyl sulfoxide, SU/H+PBS: Semaxanib/Hypoxia+PBS, SU/H+EXSM: Semaxanib/Hypoxia+exosome treatment, SU/H+EXSM+Sildenafil: Semaxanib/Hypoxia+combined exosome and Sildenafil treatment.

DETAILED DESCRIPTIONS

Some MSC extracellular vesicles or exosomes (e.g. bone marrow MSC extracellular vesicles or exosomes) can enhance glucose oxidation and normalize mitochondrial function. Thus, these extracellular vesicles or exosomes can confer therapeutic benefit in PAH and diseases or conditions associated with mitochondrial dysfunction. The present inventors isolated potent extracellular vesicle or exosome populations, which effectively prevented hypoxia-induced PAH in mice. Proteomics and RNAseq analysis of the potent extracellular vesicle or exosome populations show that they contain higher expression levels of genes in the glycolysis pathway, the TCA cycle and the electron transport chain. In particular, the potent extracellular vesicles or exosomes have increased expression levels of pyruvate kinase (PKM2) and ATPase, as well as their corresponding enzymatic activities. The present inventors also discovered that exposure of pulmonary artery smooth muscle cells (SMC) to acute hypoxia leads to the up-regulation of multiple genes involved in glycolysis, the TCA cycle, and the electron transport chain. Treatment of SMCs with the potent population of extracellular vesicles or exosomes prior to the hypoxia challenge normalized these genetic signatures. Furthermore, based on global metabolomics analysis, the potent population of extracellular vesicles or exosomes enhances glycolysis and ATP production in hypoxia-exposed SMCs. Without wishing to be bound by the theory, the potent population of extracellular vesicles or exosomes may improve mitochondrial function in target cells through both genetic reprograming and protein integration within key pathways, such as the glycolysis pathway, the TCA cycle, and/or the electron transport chain (see FIG. 9).

In some embodiments, the extracellular vesicles or exosomes of the present invention increase the expression of PDH and GLUD1, and therefore increase flux into the TCA cycle. Without wishing to be bound by the theory, the potent population of extracellular vesicles or exosomes may increase the expression of PDH and GLUD1 by inhibition of SIRT4, which is a known inhibitor of both PDH and GLUD1. Thus, in some embodiments, the extracellular vesicles or exosomes increase TCA cycle function.

It is contemplated that the present invention can be applied in treating pulmonary hypertension, including PAH, as well as treatment of diseases and conditions associated with mitochondrial dysfunction.

A. Definition

Unless otherwise specified, "a" or "an" means "one or more."

Unless specifically defined otherwise, all technical and scientific terms used herein shall be taken to have the same meaning as commonly understood by one of ordinary skill in the art.

Unless otherwise indicated, the recombinant protein, cell culture, and immunological techniques utilized in the present disclosure are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present), and are incorporated herein by reference.

As used herein, the term "subject" (also referred to herein as a "patient") includes warm-blooded animals, preferably mammals, including humans. In a preferred embodiment, the subject is a primate. In an even more preferred embodiment, the subject is a human.

As used herein the terms "treating", "treat," or "treatment" include reducing, mitigating, or eliminating at least one symptom of vasculopathy.

As used herein the terms "preventing", "prevent" or "prevention" include stopping or hinder the appearance or existence of at least one symptom of vasculopathy.

As used here, the term "expression" means RNA expression and/or protein expression level of one or more genes. In other words, the term "expression" can refer to either RNA expression or protein expression.

As used here, the term "hypoxia" refers to a condition with an oxygen ($O_2$) concentration below atmospheric $O_2$ concentration, 20%. In some embodiments, hypoxia refers to a condition with $O_2$ concentration that is between 0% and 10%, between 0% and 5% $O_2$, between 5% and 10%, or between 5% and 15%. In one embodiment, hypoxia refers to a concentration of oxygen of about 10% $O_2$.

As used here, the term "normoxia" refers a condition with a normal atmospheric concentration of oxygen, around 20% to 21% $O_2$.

As used here, the terms "isolating" or "isolated," when used in the context of an extracellular vesicle or exosome isolated from a cell culture or media, refers to an extracellular vesicle or exosome that, by the hand of man, exists apart from its native environment.

As used here, the term "extracellular vesicles" encompasses exosomes.

As used here, the term "population of extracellular vesicles or exosomes" refers to a population of extracellular vesicles or exosomes having a distinct characteristic. The terms "population of extracellular vesicles or exosomes" and "extracellular vesicles or exosomes" can be used interchangeably to refer to a population of extracellular vesicles or exosomes having a distinct characteristic.

As used here, the term "mesenchymal stromal cell" includes mesenchymal stem cells. Mesenchymal stem cells are cells found in bone marrow, blood, dental pulp cells, adipose tissue, skin, spleen, pancreas, brain, kidney, liver, heart, retina, brain, hair follicles, intestine, lung, lymph node, thymus, bone, ligament, tendon, skeletal muscle, dermis, and periosteum. Mesenchymal stem cells are capable of differentiating into different germ lines such as mesoderm, endoderm, and ectoderm. Thus, mesenchymal stem cells are capable of differentiating into a large number of cell types including, but not limited to, adipose, osseous, cartilaginous, elastic, muscular, and fibrous connective tissues. The specific lineage-commitment and differentiation pathway entered into by mesenchymal stem cells depends upon various influences, including mechanical influences and/or endogenous bioactive factors, such as growth factors, cytokines, and/or local microenvironmental conditions established by host tissues. Mesenchymal stem cells are thus non-hematopoietic progenitor cells that divide to yield daughter cells that are either stem cells or are precursor cells which in time will irreversibly differentiate to yield a phenotypic cell.

Some embodiments of the invention relate broadly to mesenchymal stromal cell extracellular vesicles or exosomes, which are interchangeably referred to as mesenchymal stromal cell extracellular vesicles or exosomes, or MSC extracellular vesicles or exosomes, or extracellular vesicles or exosomes.

B. Vasculopathy

Vasculopathy includes, but is not limited to, pulmonary hypertension such as pulmonary arterial hypertension (PAH), peripheral vascular disease (PVD), critical limb ischemia (CLI), coronary artery disease, and diabetic vasculopathy.

Pulmonary hypertension, e.g. pulmonary arterial hypertension (PAH), refers to a condition in which the pressure in the lung circulation increases, eventually causing heart failure and death. Although many causes and conditions are found to be associated with PAH, many of them share in common several fundamental pathophysiological features. One feature among these processes is dysfunction of the endothelium, the internal cellular layer of all vessel walls, which is normally responsible for the production and metabolism of a large array of substances that regulate vessel tone and repair and inhibit clot formation. In the setting of PAH, endothelial dysfunction can lead to excessive production of deleterious substances and impaired production of protective substances. Whether this is the primary event in the development of PAH or part of a downstream cascade remains unknown, but in either case, it is a factor in the progressive vasoconstriction and vascular proliferation that characterize the disease. The present invention provides a method for treating pulmonary hypertension, including PAH, using isolated extracellular vesicles or exosomes.

The term peripheral vascular disease (PVD) refers to damage, dysfunction or obstruction within peripheral arteries and veins. Peripheral artery disease is the most common form of PVD. Peripheral vascular disease is the most common disease of the arteries and is a very common condition in the United States. It occurs mostly in people older than 50 years. Peripheral vascular disease is a leading cause of disability among people older than 50 years, as well as in those people with diabetes. About 10 million people in the United States have peripheral vascular disease, which translates to about 5% of people older than 50 years. The number of people with the condition is expected to grow as the population ages. Men are slightly more likely than women to have peripheral vascular disease.

Critical limb ischemia (CLI), due to advanced peripheral arterial occlusion, is characterized by reduced blood flow and oxygen delivery at rest, resulting in muscle pain at rest and non-healing skin ulcers or gangrene (Rissanen et al., *Eur. J. Clin. Invest.* 31:651-666 (2001); Dormandy and Rutherford, *J. Vasc. Surg.* 31:S1-S296 (2000)). Critical limb ischemia is estimated to develop in 500 to 1000 per million individuals in one year ("Second European Consensus Document on Chronic Critical Leg Ischemia", *Circulation* 84(4 Suppl.) IV 1-26 (1991)). In patients with critical limb ischemia, amputation, despite its associated morbidity, mortality and functional implications, is often recommended as a solution against disabling symptoms (M. R. Tyrrell et al., *Br. J. Surg.* 80: 177-180 (1993); M. Eneroth et al., Int. Orthop. 16: 383-387 (1992)). There exists no optimal medical therapy for critical limb ischemia (*Circulation* 84(4 Suppl.): IV 1-26 (1991)).

Coronary artery disease (atherosclerosis) is a progressive disease in humans wherein one or more coronary arteries gradually become occluded through the buildup of plaque. The coronary arteries of patients having this disease are often treated by balloon angioplasty or the insertion of stents to prop open the partially occluded arteries. Ultimately, these patients are required to undergo coronary artery bypass surgery at great expense and risk.

Bronchopulmonary Dysplasia (BPD) is a chronic lung disease of premature infants. It is characterized by prolonged lung inflammation, decrease in number of alveoli and thickened alveolar septae, abnormal vascular growth with "pruning" of distal blood vessels, and limited metabolic and anti-oxidant capacity. There are 14,000 new cases of BPD per year in the US. Importantly, a diagnosis of BPD often leads to other further conditions, including PAH, emphysema, asthma, increase cardiovascular morbidity and post-neonatal mortality, increased neurodevelopmental impairment and cerebral palsy, emphysema as young adults. Currently, there is no standard therapy for BPD. Some BPD patients are treated with gentle ventilation and corticosteroids, but these treatments show no effects on neuro outcomes or death. The primary risk for BPD exists in infants between 24-28 weeks after birth, which correspond to the period of the beginning of saccular development. The infants at high risk are of 1.3 to 2.2 pounds.

In one aspect, the exosomes of the present invention may be used to treat BPD. In some embodiments, the exosomes increase immunomodulatory capacity of the lung. In some embodiments, the exosomes promote angiogenesis in the lung. In some embodiments, the exosomes increase mitochondrial metabolism of the lung.

C. Mitochondrial Dysfunction

Mitochondria are intracellular organelles responsible for a number of metabolic transformations and regulatory functions. They produce much of the ATP employed by eukaryotic cells. They are also the major source of free radicals and reactive oxygen species that cause oxidative stress. Consequently, mitochondrial defects are damaging, particularly to neural and muscle tissues, which have high energy level demands. Thus, energetic defects have been implicated in forms of movement disorders, cardiomyopathy, myopathy, blindness, and deafness (DiMauro et al. (2001) *Am. J. Med. Genet.* 106, 18-26; Leonard et al. (2000) Lancet. 355, 299-304). Mitochondrial dysfunction can involve increased lactate production, diminished respiration and ATP production. Mitochondrial dysfunction can manifest in consequences of oxidative stress.

The present invention provides methods for treating diseases or conditions associated with mitochondrial dysfunction. Mitochondrial dysfunction can be associated with decreased mitochondrial glucose oxidation in the subject.

In some embodiments, the disease or condition associated with mitochondrial dysfunction is selected from the group consisting of Friedreich's ataxia, Leber's Hereditary Optic Neuropathy, Kearns-Sayre Syndrome, Mitochondrial Encephalomyopathy with Lactic Acidosis and Stroke-Like Episodes, Leigh syndrome, obesity, atherosclerosis, amyotrophic lateral sclerosis, Parkinson's Disease, cancer, heart failure, myocardial infarction (MI), Alzheimer's Disease, Huntington's Disease, schizophrenia, bipolar disorder, fragile X syndrome, and chronic fatigue syndrome.

D. Mitochondrial Energy Production

Cells in eukaryotic organisms require energy to carry out cellular processes. Such energy is mainly stored in the phosphate bonds of adenosine 5'-triphosphate ("ATP"). There are certain pathways that generate energy in eukaryotic organisms, including: (1) glycolysis; (2) the TCA cycle (also referred to as Krebs Cycle or citric acid cycle); and (3) oxidative phosphorylation. For ATP to be synthesized, carbohydrates are first hydrolyzed into monosaccharides (e.g., glucose), and lipids are hydrolyzed into fatty acids and glycerol. Likewise, proteins are hydrolyzed into amino acids. The energy in the chemical bonds of these hydrolyzed molecules are then released and harnessed by the cell to form ATP molecules through numerous catabolic pathways.

The main source of energy for living organisms is glucose. In breaking down glucose, the energy in the glucose molecule's chemical bonds is released and can be harnessed by the cell to form ATP molecules. The process by which this occurs consists of several stages. The first is called glycolysis, in which the glucose molecule is broken down into two smaller molecules called pyruvic acid.

In glycolysis, glucose and glycerol are metabolized to pyruvate via the glycolytic pathway. During this process, two ATP molecules are generated. Two molecules of NADH are also produced, which can be further oxidized via the electron transport chain and result in the generation of additional ATP molecules.

Glycolysis involves many enzyme-catalyzed steps that break down glucose (and other monosacharrides) into 2 pyruvate molecules. In return, the pathway leads to the generation of a sum of 2 ATP molecules. The pyruvate molecules generated from the glycolytic pathway enter the mitochondria from the cytosol. The molecules are then converted to acetyl co-enzyme A (Acetyl-CoA) for entry into the TCA cycle. The TCA cycle consists of the bonding of acetyl coenzyme-A with oxaloacetate to form citrate. The formed citrate is then broken down through a series of enzyme-catalyzed steps to generate additional ATP molecules.

Energy released from the TCA cycle in the mitochondrial matrix enters the mitochondrial electron transport chain as NADH (complex I) and $FADH_2$ (complex II). These are the first two of five protein complexes involved in ATP production, all of which are located in the inner mitochondrial membrane. Electrons derived from NADH (by oxidation with a NADH-specific dehydrogenase) and FAD¾ (by oxidation with succinate dehydrogenase) travel down the respiratory chain, releasing their energy in discrete steps by driving the active transport of protons from the mitochondrial matrix to the intermembrane space (i.e., through the inner mitochondrial membrane). The electron carriers in the respiratory chain include flavins, protein-bound iron-sulfur centers, quinones, cytochromes and copper. There are two molecules that transfer electrons between complexes: coenzyme Q (complex I→III, and complex II→III) and cytochrome c (complex III→IV). The final electron acceptor in the respiratory chain is (¾, which is converted to ¾ in complex IV.

Some embodiments of the present invention relate to extracellular vesicles or exosomes that have increased expression of at least one genes or proteins in glycolysis, the TCA cycle, and/or the electron transport chain. In some embodiments, the genes are selected from the group of genes represented by Table 1 below.

TABLE 1

| Pathway | Proteins | Genes |
| --- | --- | --- |
| Glycolysis | AGI, ALDO, TPI, GAPDH, ENO, PGAM, PK | ALDOA, ENO3, GPI, HK2,3, PFK, PGM, PK |
| TCA Cycle | OGDH | MDH2, OGDH, PC, PDHA1, PDHB, SDHA, SDHC, SUCLG2 |
| Electron Transport Chain | ETFA, ATPase | Complex I (NDUFC2, NDUFB1, NDUFS5, NDUFA8, NDUFA9, NDUFS2); Complex II (SDHA, SDHC); Complex III (UQCRH1); Complex IV (Cox 6c1, Cox10); Complex V (ATPase genes) |

In some embodiments, the gene in the glycolysis pathway is selected from the group consisting of PK, AGI, ALDO, ALDOA, ENO3, GPI, HK2, HK3, PFK, PGM, TPI, GAPDH, ENO, and PGAM.

In some embodiments, the gene in the TCA cycle is selected from the group consisting of MDH2, OGDH, PC, PDHA1, PDHB, SDHA, SDHC, and SUCLG2.

In some embodiments, the gene in the electron transport chain is selected from the group consisting of ETFA, ATPase, NDUFC2, NDUFB1, NDUFS5, NDUFA8, NDUFA9, NDUFS2, SDHA, SDHC, UQCRH1, Cox 6c1, and Cox10.

In some embodiments, the extracellular vesicles or exosomes have increased expression of PK.

In some embodiments, the extracellular vesicles or exosomes have increased expression of ATPase.

In some embodiments, the extracellular vesicles or exosomes have increased expression of PK and ATPase.

E. Extracellular Vesicles Isolated from Mesenchymal Stromal Cells

The extracellular vesicles or exosomes of the invention can be, for example, membrane (e.g., lipid bilayer) vesicles that are released from mesenchymal stromal cells. They can have, for example, a diameter ranging from about 30 nm to 100 nm. By electron microscopy, extracellular vesicles or exosomes can appear to have a cup-shaped morphology. They can, for example, sediment at about 100,000×g and have a buoyant density in sucrose of about 1.10 to about 1.21 g/ml.

Mesenchymal stromal cells may be harvested from a number of sources including but not limited to bone marrow, blood, periosteum, dermis, umbilical cord blood and/or matrix (e.g., Wharton's Jelly), and placenta. Methods for harvest of mesenchymal stromal cells are described in greater detail in the Examples. Reference can also be made to U.S. Pat. No. 5,486,359, which is incorporated herein by reference, for other harvest methods that can be used in the present invention.

The mesenchymal stromal cells, and thus the extracellular vesicles or exosomes, contemplated for use in the methods of the invention may be obtained from the same subject to be treated (and therefore would be referred to as autologous to the subject), or they may be obtained from a different subject, preferably a subject of the same species (and therefore would be referred to as allogeneic to the subject).

As used herein, it is to be understood that aspects and embodiments of the invention relate to cells as well as cell populations, unless otherwise indicated. Thus, where a cell is recited, it is to be understood that a cell population is also contemplated unless otherwise indicated.

Some aspects of the invention refer to isolated extracellular vesicles or exosomes. As used herein, an isolated extracellular vesicle or exosome is one which is physically separated from its natural environment. An isolated extracellular vesicle or exosome may be physically separated, in whole or in part, from a tissue or cellular environment in which it naturally exists, including mesenchymal stromal cells. In some embodiments of the invention, a composition of isolated extracellular vesicles or exosomes may be free of cells such as mesenchymal stromal cells, or it may be free or substantially free of conditioned media. In some embodiments, the isolated extracellular vesicles or exosomes may be provided at a higher concentration than extracellular vesicles or exosomes present in un-manipulated conditioned media. Extracellular vesicles or exosomes may be isolated from conditioned media from mesenchymal stromal cell culture.

Generally any suitable method for purifying and/or enriching extracellular vesicles or exosomes can be used, such as methods comprising magnetic particles, filtration, dialysis, ultracentrifugation, ExoQuick™ (Systems Biosciences, CA, USA), and/or chromatography. In some embodiments, extracellular vesicles or exosomes are isolated by centrifugation and/or ultracentrifugation. Extracellular vesicles or exosomes can also be purified by ultracentrifugation of clarified conditioned media. They can also be purified by ultracentrifugation into a sucrose cushion. The protocol is described in, for example, Thery et al. *Current Protocols in Cell Biol.* (2006) 3.22, which is incorporated herein by reference. In some embodiments, extracellular vesicles or exosomes are isolated by a single step size exclusion chromotography. The protocol is described in, for example, Boing et al. *Journal of Extracellular Vesicles* (2014) 3:23430, which is incorporated herein by reference. A detailed method for harvest of extracellular vesicles or exosomes from mesenchymal stromal cells or mesenchymal stem cells is provided in the Examples.

The invention also contemplates immediate use of extracellular vesicles or exosomes or alternatively short- and/or long-term storage of extracellular vesicles or exosomes, for example, in a cryopreserved state prior to use. Proteinase inhibitors are typically included in freezing media as they provide extracellular vesicle or exosome integrity during long-term storage. Freezing at −20° C. is not preferable since it is associated with increased loss of extracellular vesicle or exosome activity. Quick freezing at −80° C. is more preferred as it preserves activity. See for example Kidney International (2006) 69, 1471-1476, which is incorporated herein by reference. Additives to the freezing media may be used in order to enhance preservation of extracellular vesicle or exosome biological activity. Such additives will be similar to the ones used for cryopreservation of intact cells and may include, but are not limited to DMSO, glycerol and polyethylene glycol.

F. Assessment of the Potency of Extracellular Vesicles or Exosomes

The present invention provides using right ventricular systolic pressure (RVSP) to measure the effect of extracellular vesicle or exosome treatment on hypoxia induced PAH mice model, and to identify potent populations of extracellular vesicles or exosomes. In some embodiments, the potent populations of extracellular vesicles or exosomes are capable of reducing RVSP of mice subjected to a three-week chronic hypoxia exposure by at least about 10%, 12.5%, 15%, 17.5%, 20%, 22.5%, 25%, 27.5%, or 30%, compared to control mice subjected to a three-week chronic hypoxia exposure and treated with PBS buffer.

In some embodiments, the potent populations of extracellular vesicles or exosomes are identified by delta RVSP. As used here, delta RVSP is defined as the RVSP of hypoxia-exposed mice treated with extracellular vesicles or exosomes minus RVSP of normoxia mice. In some embodiments, a population of extracellular vesicles or exosomes is potent if delta RVSP is less than about 6, 5, 4, 3, or 2 mmHg.

In some embodiments, the potency of populations of extracellular vesicles or exosomes are characterized by their ability to increase $O_2$ consumption by smooth muscle cells (SMC) lysates. In some embodiments, the potent populations of extracellular vesicles or exosomes are capable of increasing $O_2$ consumption by SMC lysate subjected to a 24-hour hypoxia exposure by at least about 10%, 15%, 20%, 25%, 30%, 35%, or 40%, compared to control SMC cell lysates subjected to a 24-hour hypoxia exposure and treated with PBS control.

In some embodiments, the potency of populations of extracellular vesicles or exosomes is characterized by their PK activity. In some embodiments, the potent population of extracellular vesicles or exosomes have a PK activity of at least about 0.15 nmol/min/ml, 0.16 nmol/min/ml, 0.17 nmol/min/ml, 0.18 nmol/min/ml, 0.19 nmol/min/ml, 0.20 nmol/min/ml, 0.21 nmol/min/ml, 0.22 nmol/min/ml, 0.23 nmol/min/ml, 0.24 nmol/min/ml, 0.25 nmol/min/ml, 0.3 nmol/min/ml, or 0.4 nmol/min/ml.

In some embodiments, the potency of populations of extracellular vesicles or exosome are characterized by their LDH activity. In some embodiments, the potency of populations of extracellular vesicles or exosome are characterized by their ability to decrease LDH secreted by hypoxia-exposed SMC by at least about 10%, 20%, 30%, or 40%.

In some embodiments, the extracellular vesicles or exosome of the present invention are isolated based on one or more criteria in the table below:

| | |
|---|---|
| Sterility | PT-PCR mir204 |
| Appearance | MSC-CD105 |
| Total Protein | PT-PCR mitochondrial genes |
| Particle Count | 2D gel electrophoresis |
| Total RNA | RNAseq fingerprint analysis |
| Total Phospholipid | In vitro potency assay |

In some embodiments, the isolated extracellular vesicles or exosomes comprise an amount of mir204 that is at least 10%, 20%, 30%, 50%, or 100% more than the average level of mir204 in all extracellular vesicles or exosomes of the mesenchymal stromal cells.

In some embodiments, the isolated extracellular vesicles or exosomes comprise an amount of CD105, GAPDH, DLST, and/or ATP5A1 that is at least 10%, 20%, 30%, 50%, or 100% more than the average level of CD105, GAPDH, DLST, and/or ATP5A1 in all extracellular vesicles or exosomes of the mesenchymal stromal cells.

In some embodiments, the isolated extracellular vesicles or exosomes comprise an amount of RNA expression of SORCS1, FHIT and/or ANKRD30BL that is at least 10%, 20%, 30%, 50%, or 100% more than the average level of RNA expression of SORCS1, FHIT and/or ANKRD30BL in all extracellular vesicles or exosomes of the mesenchymal stromal cells.

In some embodiments, the isolated extracellular vesicles or exosomes have reduced MHCII contaminants or are substantially or totally free of MHCII contaminants, such as comprising an amount of MHCII contaminants that is at least 50%, 70%, 80%, 90%, 95%, 98%, or 99% less than the average level of MHCII contaminants in all extracellular vesicles or exosomes of the mesenchymal stromal cells.

In some embodiments, the isolated extracellular vesicles or exosomes have reduced fibronectin content or are substantially or totally free of fibronectin, such as comprising an amount of fibronectin that is at least 50%, 70%, 80%, 90%, 95%, 98%, or 99% less than the average level of fibronectin in all extracellular vesicles or exosomes of the mesenchymal stromal cells.

G. Treatment Using Extracellular Vesicles or Exosomes

Compositions useful for the methods of the present disclosure can be administered via, inter alia, localized injection, including catheter administration, systemic injection, localized injection, intravenous injection, intrauterine injection or parenteral administration. When administering a therapeutic composition described herein (e.g., a pharmaceutical composition), it will generally be formulated in a unit dosage injectable form (e.g. solution, suspension, or emulsion).

The invention contemplates single or repeated administration of extracellular vesicles or exosomes, including two, three, four, five or more administrations of extracellular vesicles or exosomes. In some embodiments, the extracellular vesicles or exosomes may be administered continuously. Repeated or continuous administration may occur over a period of several hours (e.g., 1-2, 1-3, 1-6, 1-12, 1-18, or 1-24 hours), several days (e.g., 1-2, 1-3, 1-4, 1-5, 1-6 days, or 1-7 days) or several weeks (e.g., 1-2 weeks, 1-3 weeks, or 1-4 weeks) depending on the severity of the condition being treated. If administration is repeated but not continuous, the time in between administrations may be hours (e.g., 4 hours, 6 hours, or 12 hours), days (e.g., 1 day, 2 days, 3 days, 4 days, 5 days, or 6 days), or weeks (e.g., 1 week, 2 weeks, 3 weeks, or 4 weeks). The time between administrations may be the same or they may differ. As an example, if the symptoms of the disease appear to be worsening the extracellular vesicles or exosomes may be administered more frequently, and then once the symptoms are stabilized or diminishing the extracellular vesicles or exosomes may be administered less frequently.

The invention also contemplates repeated administration of low dosage forms of extracellular vesicles or exosomes as well as single administrations of high dosage forms of extracellular vesicles or exosomes. Low dosage forms may range from, without limitation, 1-50 micrograms per kilogram, while high dosage forms may range from, without limitation, 51-1000 micrograms per kilogram. It will be understood that, depending on the severity of the disease, the health of the subject, and the route of administration, inter alia, the single or repeated administration of low or high dose extracellular vesicles or exosomes are contemplated by the invention.

The extracellular vesicles or exosomes may be used (e.g., administered) in pharmaceutically acceptable preparations (or pharmaceutically acceptable compositions), typically when combined with a pharmaceutically acceptable carrier. The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically-acceptable carrier" as used herein means a pharmaceutically-acceptable material, composition or vehicle, such as a liquid or solid filler, diluent, excipient, or solvent encapsulating material.

Such preparations may routinely contain pharmaceutically acceptable concentrations of salt, buffering agents, preservatives, compatible carriers, and may optionally comprise other (i.e., secondary) therapeutic agents. A pharmaceutically acceptable carrier is a pharmaceutically acceptable material, composition or vehicle, such as a liquid or solid filler, diluent, excipient, solvent or encapsulating material, involved in carrying or transporting a prophylactically or therapeutically active agent. Each carrier must be "acceptable" in the sense of being compatible with the other ingredients of the formulation and not injurious to the subject. Some examples of materials which can serve as pharmaceutically acceptable carriers include sugars, such as lactose, glucose and sucrose; glycols, such as propylene glycol; polyols, such as glycerin, sorbitol, mannitol and polyethylene glycol; esters, such as ethyl oleate and ethyl laurate; buffering agents, such as magnesium hydroxide and aluminum hydroxide; pyrogen-free water; isotonic saline; Ringer's solution; ethyl alcohol; phosphate buffer solutions; and other nontoxic compatible substances employed in pharmaceutical formulations.

The preparations of the invention are administered in effective amounts. An effective amount is that amount of an agent that alone stimulates the desired outcome. The absolute amount will depend upon a variety of factors, including the material selected for administration, whether the administration is in single or multiple doses, and individual patient parameters including age, physical condition, size, weight, and the stage of the disease. These factors are well known to those of ordinary skill in the art and can be addressed with no more than routine experimentation.

The invention also encompasses a packaged and labelled pharmaceutical product. This article of manufacture or kit includes the appropriate unit dosage form in an appropriate vessel or container such as a glass vial or plastic ampoule or other container that is hermetically sealed. The unit dosage form should be suitable for pulmonary delivery for example by aerosol. Preferably, the article of manufacture or kit further comprises instructions on how to use including how to administer the pharmaceutical product. The instructions may further contain informational material that advises a medical practitioner, technician or subject on how to appropriately prevent or treat the disease or disorder in question. In other words, the article of manufacture includes instructions indicating or suggesting a dosing regimen for use including but not limited to actual doses, monitoring procedures, and other monitoring information.

As with any pharmaceutical product, the packaging material and container are designed to protect the stability of the product during storage and shipment. The kits may include MSC extracellular vesicles or exosomes in sterile aqueous suspensions that may be used directly or may be diluted with normal saline for intravenous injection or use in a nebulizer, or dilution or combination with surfactant for intratracheal administration. The kits may therefore also contain the diluent solution or agent, such as saline or surfactant.

EXAMPLES

The following examples are intended to provide those of ordinary skill in the art with a complete disclosure and description of how to make and use the methods and compositions described herein, and are not intended to be limiting.

Example 1.1—Isolating Exosomes Populations

This example demonstrates isolation of exosomes from a cell culture media.

Filtration:

Conditioned media obtained from mesenchymal stem cells (MSCs) was collected in a 5 L Sartorius-stedium Flexboy® bag with 0.2 um filters. The collected conditioned media was pumped through a filter line to quickly eliminate any cells, dead cells, and cellular debris. The, the condition media was supplemented with 25 mM HEPES and 10 mM EDTA buffers using a 140 ml luer-lok syringe.

Tangential Flow Filtration:

The 5 L Flexboy® bag containing the conditioned media was connected to a tangential flow filtration (TFF) system, by a sample line attached to the Flexboy bag and connected to the top of the TFF reservoir. A Sartorius Sartocon Slice TFF with a single 100 kDa MWCO 0.1 $m^2$ Hydrosart® cassette was used. A water integrity test was conducted at the beginning and at the end of each TFF run to measure the integrity of the cassette. The system was then primed with 1 L of PBS. The media sample was then gravity fed into the reservoir. The TFF was run at 600 LMH. An initial media of 5 L volume was concentrated down to 100 mL (a 50× concentration). The retentate was collected and filtered using a 0.22 um filter. The filtrate was divided into 10 mL aliquot sample and frozen at −80° C.

Fractionation:

Samples were thawed at 37° C. for approximately 10 minutes. All samples were pooled together in a 150 ml corning bottle. A XK 50/100 column was packed using Sepharose CL-2B resin (GE). The XK 50/100 column was connected to an AKTA Aant 150 (GE). The sample was introduced into the column via the sample line. Once all the sample was introduced to the column, the elution step began (settings: flow rate of 4.6 ml/min). 0.2 CV of void column eluted out and then the fraction collector started collecting fractions at a rate of 1 minute per fraction (4.6 ml in each fraction). Fractions were collected until 0.6 CV was eluted out (exosomes eluted out between 0.3 CV-0.4 CV). PBS was used for the entire experiment. The fraction samples are capped under the hood and stored at 4° C.

Diafiltration:

Samples may be optionally subjected to a diafiltration step, preferably after the TFF step and before the Fractionation step which is similar to buffer exchange. Once a desired concentration of exosomes is reached, PBS buffer was added to the sample through a reservoir to maintain the volume while continuing to run the pump to the TFF cassette filter. Gradually, the PBS replaced the conditioned media. In order to achieve as complete of an exchange as possible, 7 total volume diafiltrations were performed to with the retentate. This step helps to remove some of the impurities in the retentate, without affecting exosome. The presence of exosomes was verified by FLOT-1 western blots, which shows decreased amount of total protein and phospholipid.

Measuring Phospholipid Concentration:

Phospholipid signaling was used for exosome detection. Briefly, after fractionation, 20 uL of each exosome prep and 80 uL of a reaction mix (Sigma) were transferred into black, clear-bottom 96-well plates (Corning, Corning, N.Y.) and incubated for 30 minutes at room temperature protected from light. Fluorescence intensity was measured at 530/585 nm using a FLUOstar Omega microplate reader (BMG Labtech, Ortenberg, Germany). In the exosome production runs shown, both A280 chromatograms and phospholipid were utilized for exosome detection.

Figure 1A:
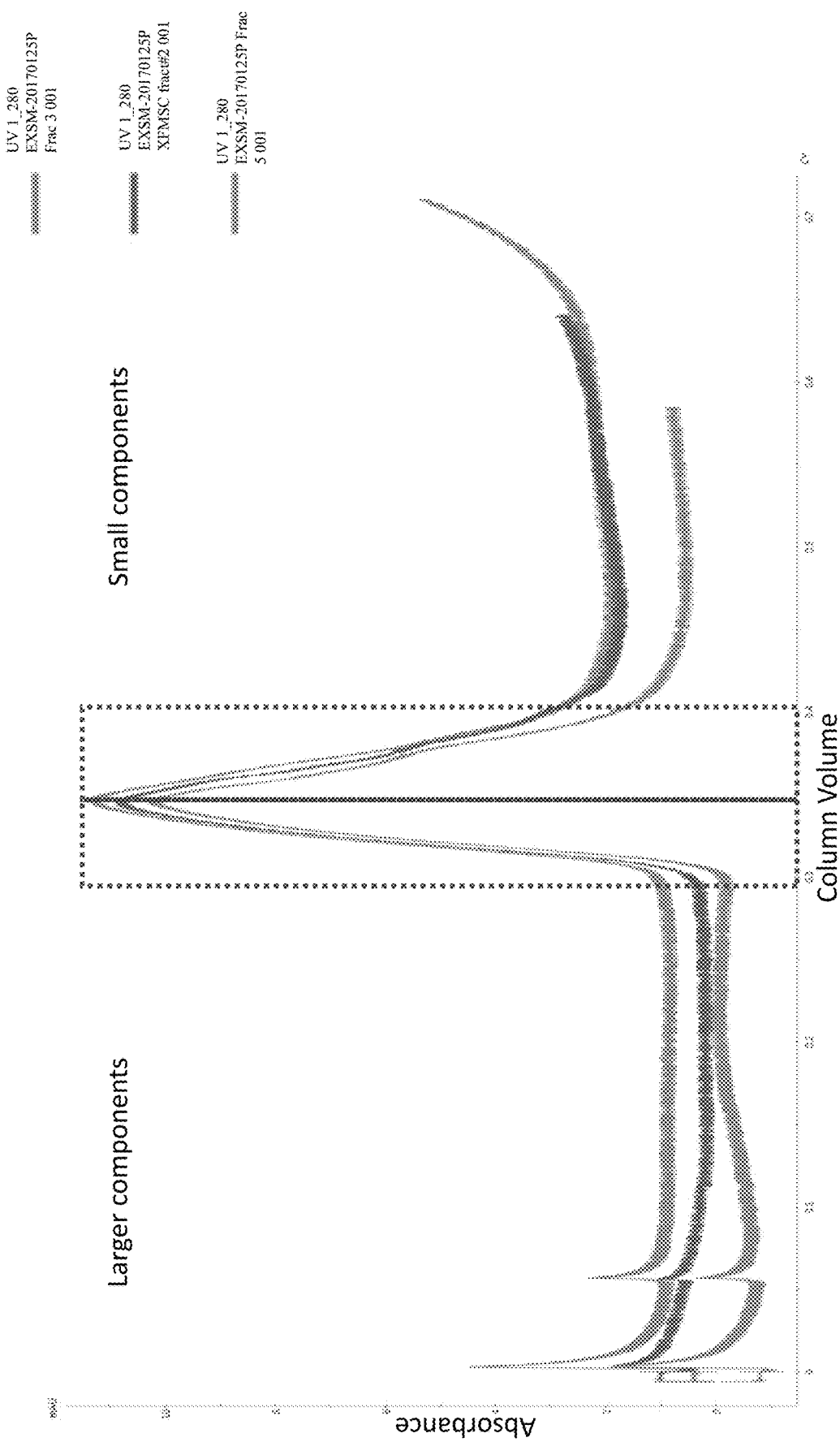
Figure 1B:
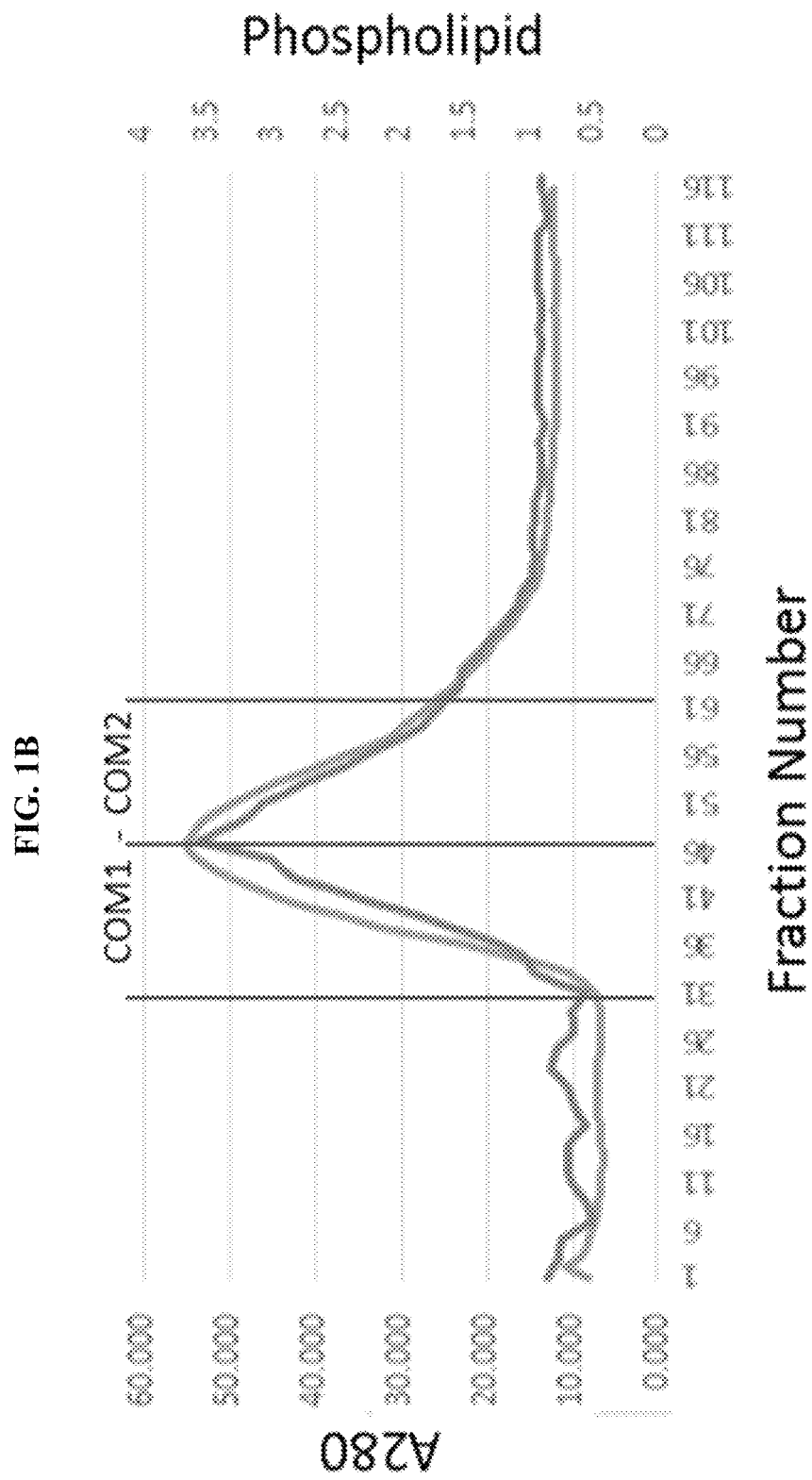

As shown in FIG. 1C, phospholipid signaling overlays well with A280 chromatograms for exosome detection.

Example 1.2—Treating Pulmonary Arterial Hypertension (PAH) in Mouse Model

Mice were subjected to a three week chronic hypoxia exposure to induce PAH (shown as an increase in Right Ventricular Systolic Pressure). Exosomes treatment consisted of a 1 time tail vein injection prior to hypoxia exposure.

Example 1.3—Identification of Potent Exosome Populations

To identify potent exosome populations, each exosome preparation was analyzed for pyruvate kinase protein expression using a PKM2 antibody (Cell Signaling, Danvers, Mass.). A capillary electrophoresis immunoassay was performed using the WES™ machine (ProteinSimple, San Jose, Calif.) according to the manufacturer's protocol. In brief, 4.2 uL of samples were mixed 1:5 with a master fluorescent mix (ProteinSimple). Samples were then heated at 95° C. for 5 min and placed on ice. The primary PKM2 antibody was diluted 1:15 in antibody diluent (ProteinSimple) and a proprietary anti-Rabbit Secondary antibody (ProteinSimple) was used. Proprietary peroxide and luminol-S (ProteinSimple) were mixed 1:1 to make the chemiluminescent substrate. The samples, blocking reagent, primary antibody, secondary antibody, chemiluminescent substrate, and wash buffer were loaded into designated wells in the provided microplate. The plate was spun at 1,000 g for 5 minutes to avoid bubbles in wells. The plate and capillary cartridges were loaded into the WES machine. After plate loading, fully automated electrophoresis and immunodetection took place in the capillary system. Proteins were separated using WES standard run settings. The data was analyzed with built-in Compass software (Proteinsimple), providing peak molecular weight signal and area under the curve values per sample.

Pyruvate Kinase Activity:

Pyruvate kinase is an enzyme in glycolysis which catalyzes the transfer of phosphate from phosphoenolpyruvate (PEP) to ADP, yielding one molecule of pyruvate and one molecule of ATP. Pyruvate kinase is measured by the abcam kit (ab83432) wherein PEP and ADP are catalyzed by PK to generate pyruvate and ATP. The generated pyruvate is oxidized by pyruvate oxidase to produce color (at λ=570 nm). Because color intensity is proportional to pyruvate amount, PK activity can be measured. PK activity generates is a kinetic assay. Data analysis can be done using the following equation:

$$PK\ activity=(pyruvate \times dilution\ factor)/(T2-T1) \times well\ volume$$

Where T2−T1 is time (mins) at timepoint 2−timepoint 1. Pyruvate (nmol) is calculated using a pyruvate standard curve (where pyruvate is calculated as final pyruvate concentration at T2 minus initial pyruvate concentration at T1). This number needs to be blank corrected. It is important that the activity measures occur within the linear range. The dataset can be analyzed at multiple time points. The best way to selected is to look at the curves and choose data points at least 2 minutes apart that fall within the linear range. Every sample within the plate is analyzed the same way. In this experiment, T1=2 min, T2=4 minutes were chosen, as these two time points were well within the linear range.

Figure 2A:
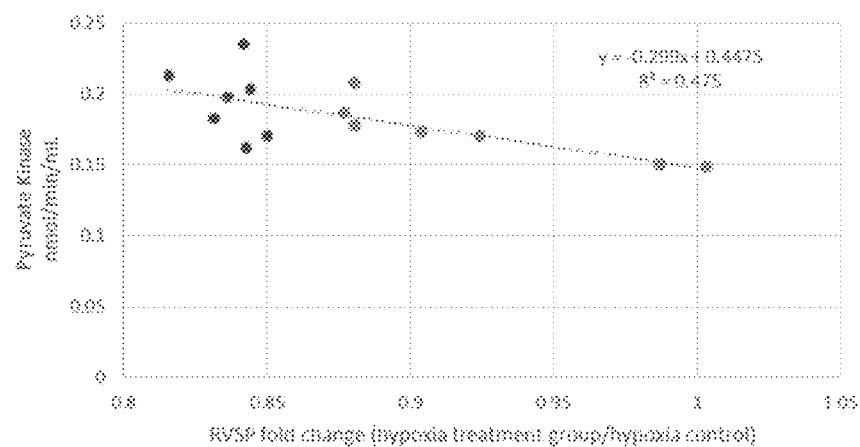
FIGS. 2A-2C depict identification of potent exosome populations.
Figure 2B:
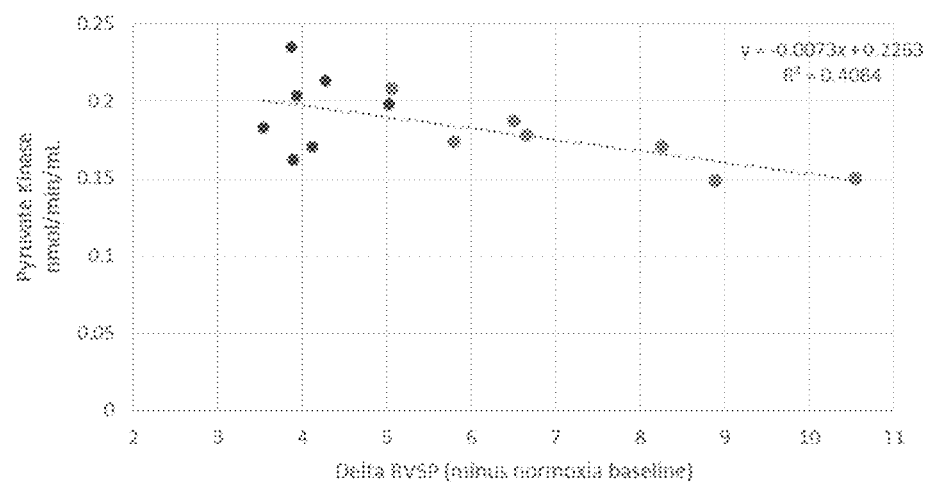
Figure 2C:
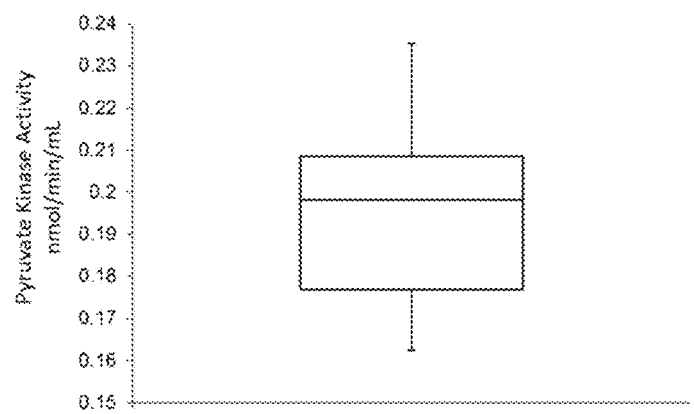

Next, pyruvate kinase activity was plotting against the in vivo RVSP fold change of each exosome preparation treatment condition over the hypoxia control. This allows for the comparison of pyruvate kinase activity to the fold improvement in RVSP with exosome treatment. See FIG. 2A. Pyruvate kinase activity was also plotted against the delta RVSP. Delta RVSP is the hypoxia treated with exosome condition minus normoxia control. See FIG. 2B. The red dots represent potent exosome populations that induced a significant improvement in RVSP. The blue dots represent exosome populations that are not potent in treating hypoxia induced PAH mice. The pyruvate kinase activity of these most potent exosome populations was then graphed in a box and whisker plot. See FIG. 2C. Therefore, the graph in (C) represents the pyruvate kinase activity range of our most potent exosome preps.

Figures 3A, 3B:
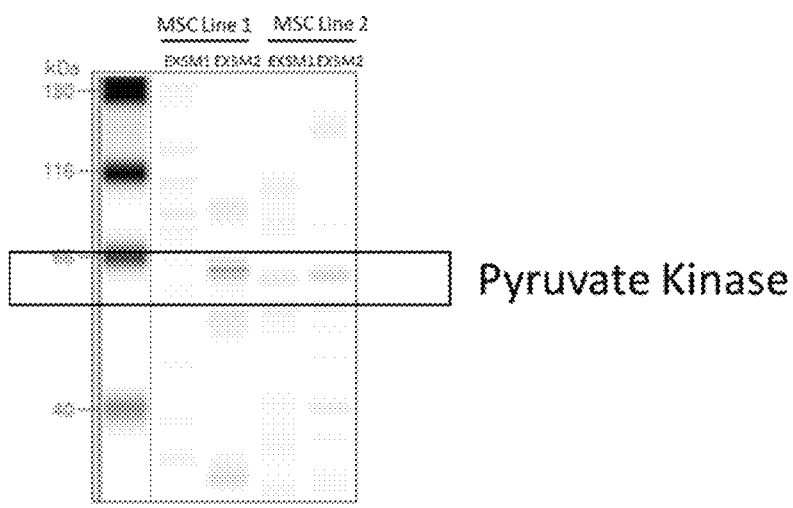
FIGS. 3A-3B illustrate proteomic analysis of different exosome populations.

Example 1.4—Proteomic Analysis and RNAseq Analysis of Potent Exosome Populations Samples exosomes were sent to Bioproximity (Chantilly, Va.) for proteomics analysis. The proteins with increased expression levels in the potent exosome population compared to the non-potent population are shown in FIG. 3(a).

Samples exosomes were sent to SBI for RNAseq analysis. The genes with increased expression levels in the potent exosome population compared to the non-potent population are shown in FIG. 4.

Example 1.5—Measuring Extracellular $O_2$ Consumption

Figure 5A:
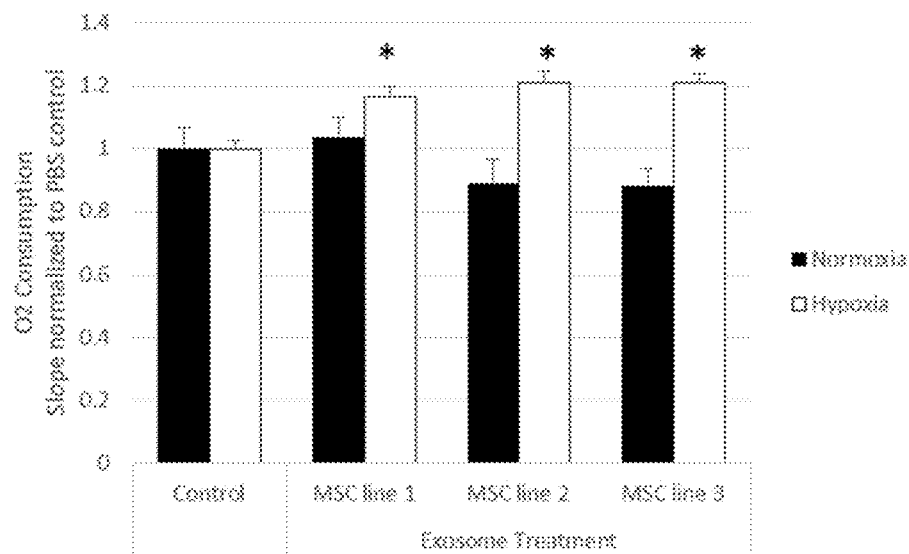
FIGS. 5A-5B depict $O_2$ consumption assay in exosome treated SMC cell lysate after 24 hour exposure to either normoxia or 4% $O_2$ hypoxia.
Figure 5B:
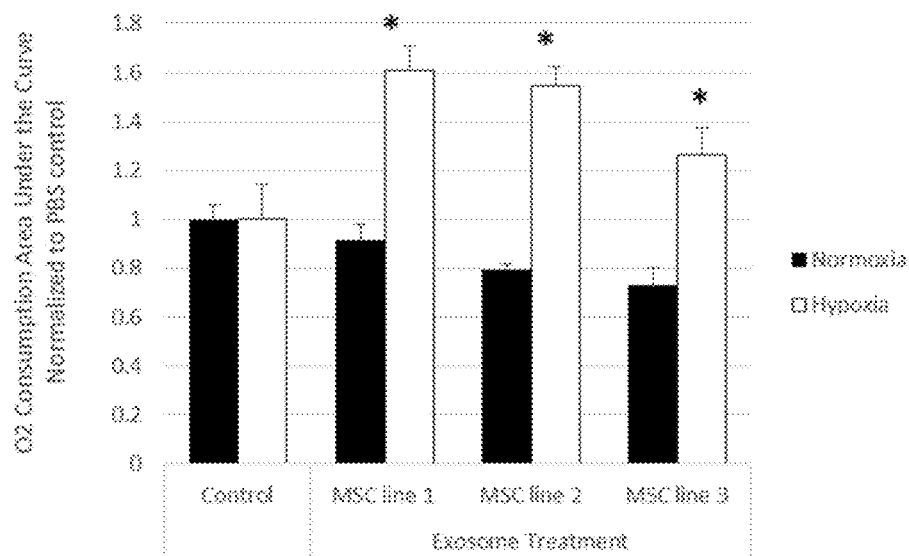

The abcam Extracellular $O_2$ Consumption Assay Kit (ab197243) was used to measure oxygen consumption of Smooth muscle cells (SMC) lysates treated with PBS (control) or exosome after 24 hour exposure to either normoxia or 4% $O_2$ hypoxia. As the cell lysates consume oxygen via the electron transport chain, oxygen was depleted in the surrounding culture media which is seen as an increase in phosphorescence signal. The micro-environment is protected from ambient air diffusion by addition of mineral oil to each well and phosphorescence signal is measured as a quenching of the $O_2$ probe supplied by the manufacturer. These data were calculated two ways: both as area under the curve and as the slope over time (data analysis using the slope is recommended by the manufacturer). FIGS. 5A-5B demonstrate that exosomes do not significantly change the cellular $O_2$ consumption in normoxia-exposed SMCs. However, exosome treatment induces an increase in $O_2$ consumption under hypoxia stress, which indicates an increase in mitochondrial function.

Example 1.6—Microarray Analysis of SMC Exposed to Acute Hypoxia

Figure 6A:
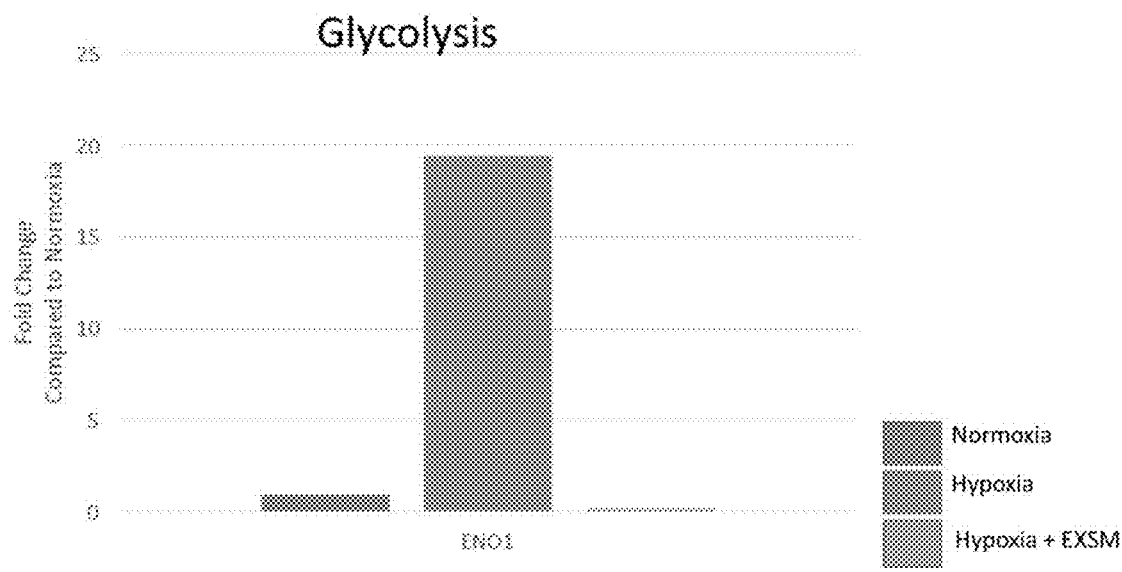
FIGS. 6A-6C illustrate results of microarray analysis of SMC lysates after acute hypoxia exposure.
Figure 6B:
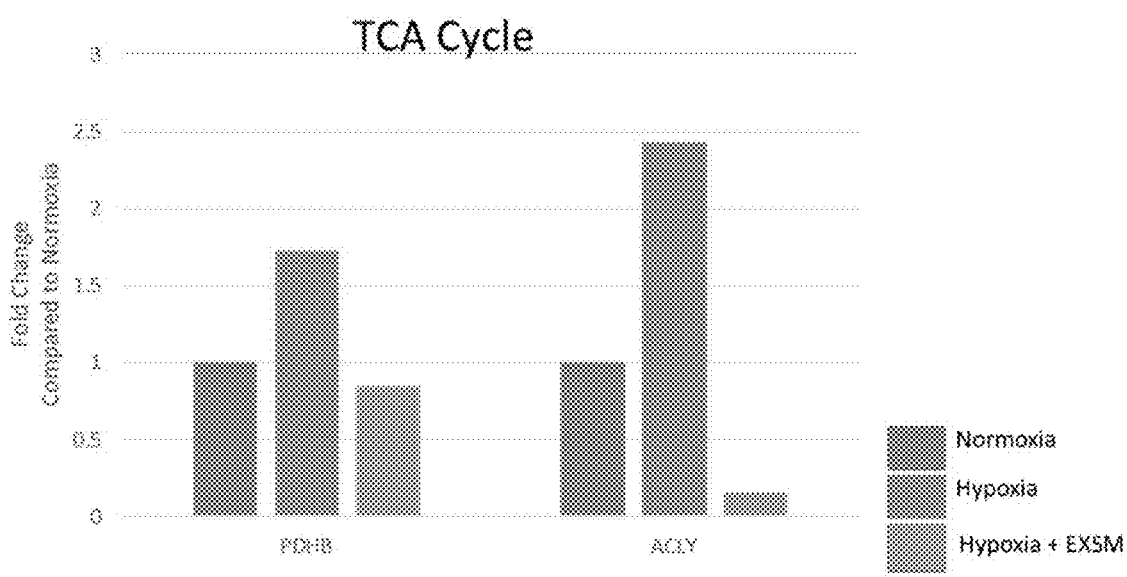
Figure 6C:
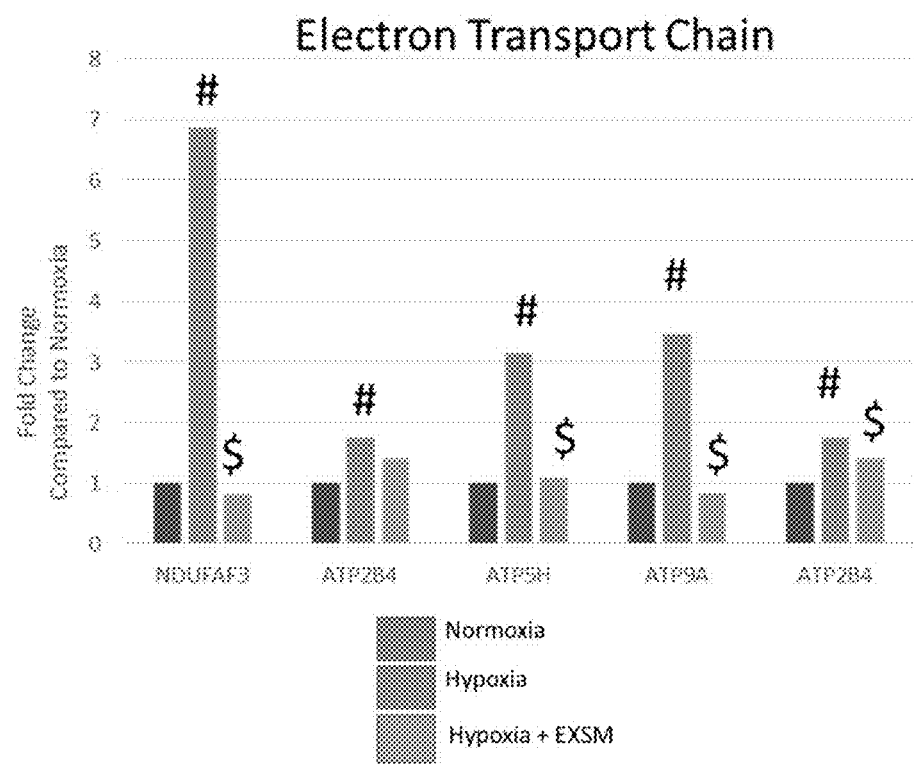
Figure 7A:
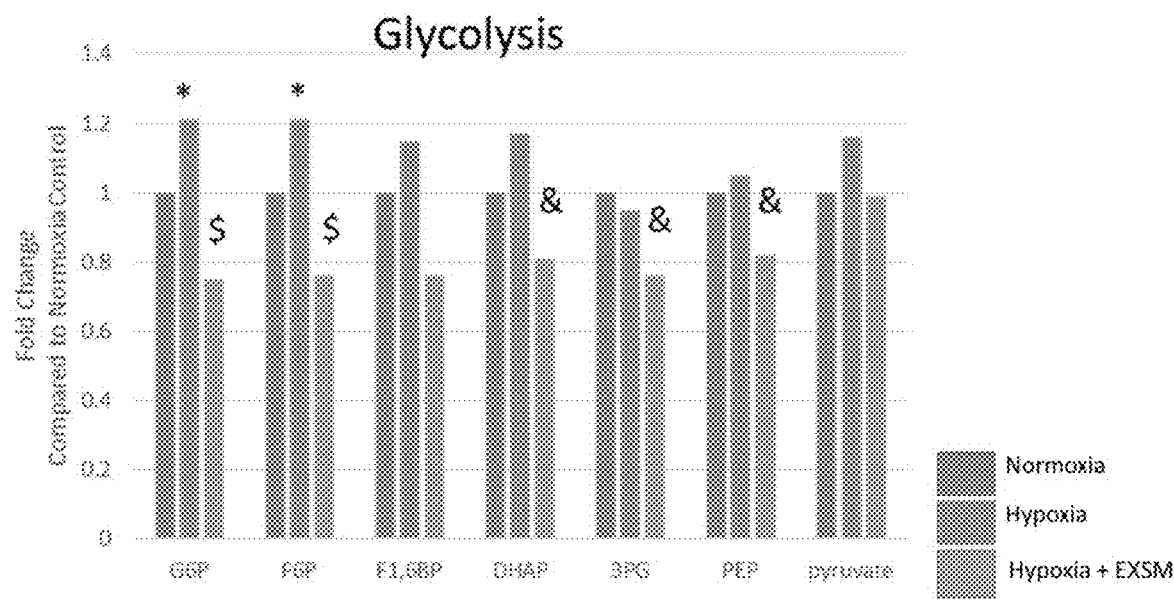
FIGS. 7A-7D show metabolomics analysis of SMC lysates after acute hypoxia exposure.
Figure 7B:
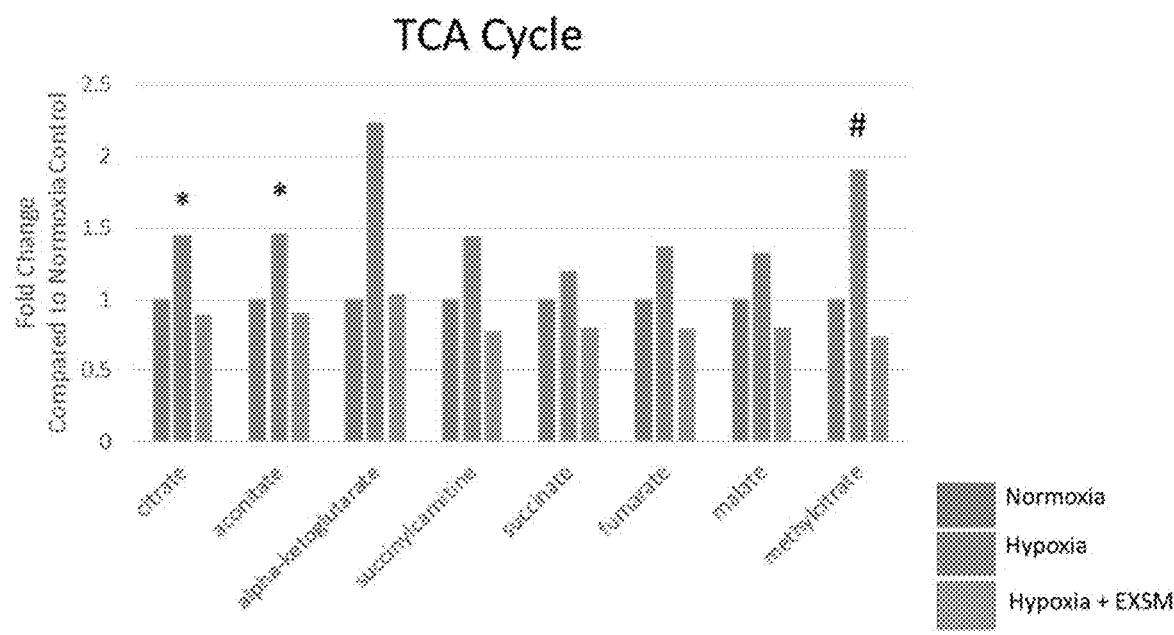
Figure 7C:
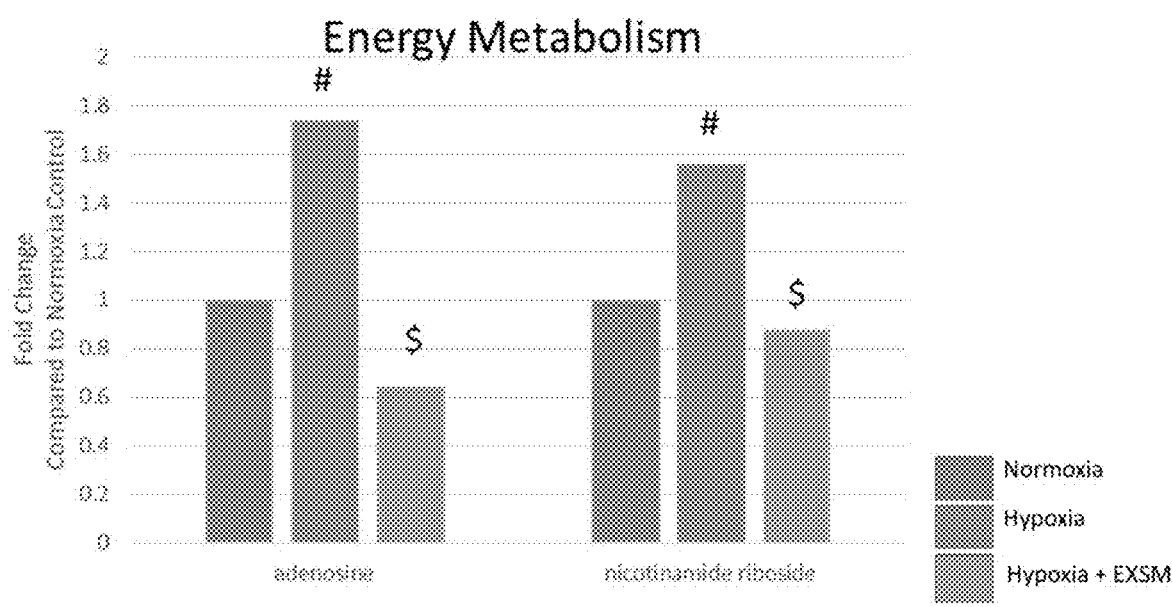
Figure 7D:
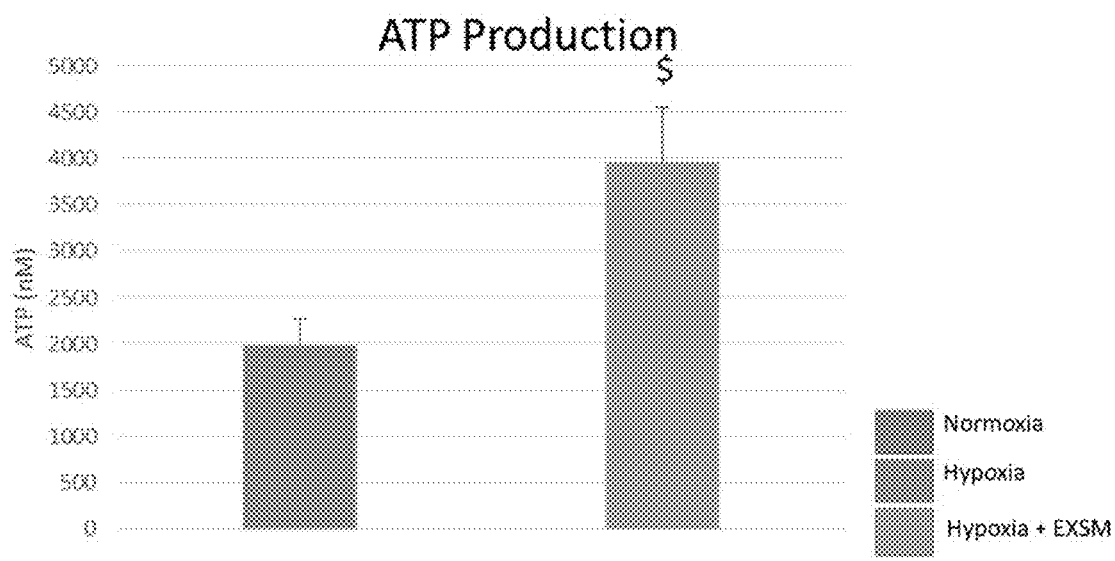
Figure 8A:
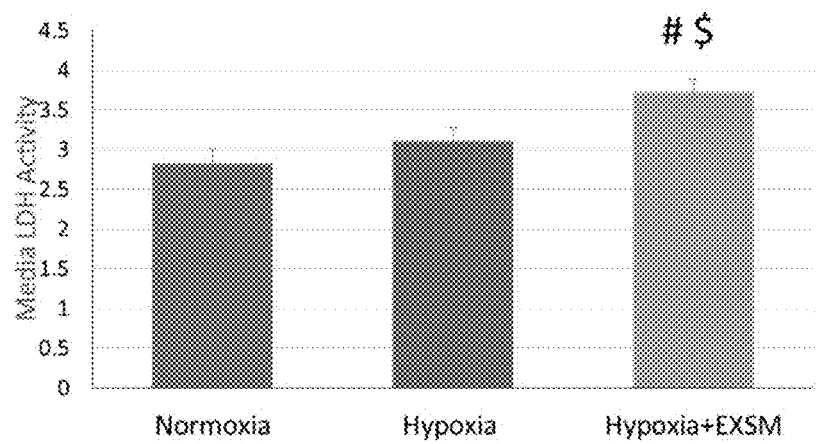
FIGS. 8A-8E show analysis of SMC lysate after exposure to hypoxia.
Figure 8B:
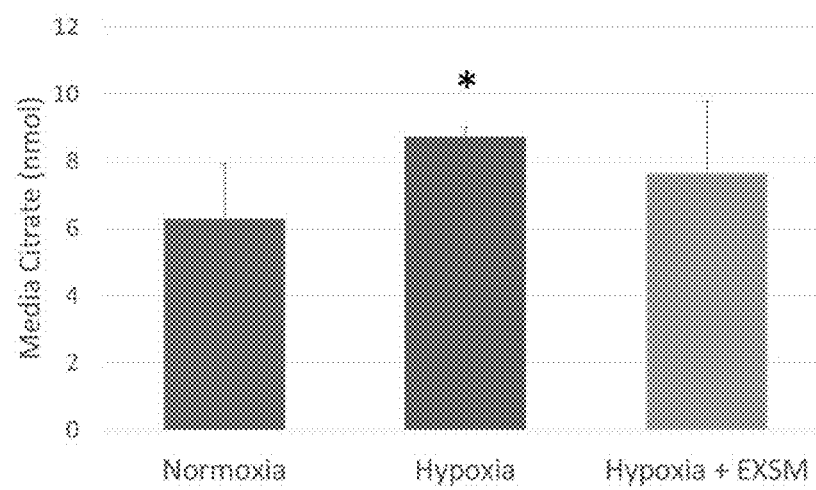
Figure 8C:
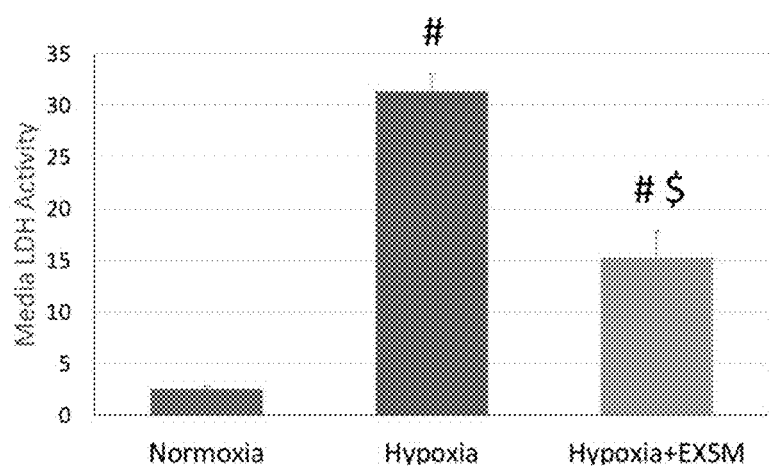
Figure 8D:
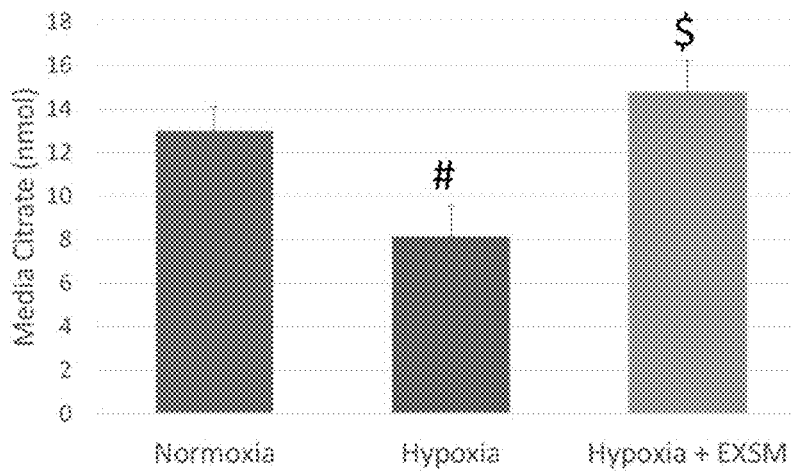
Figure 8E:
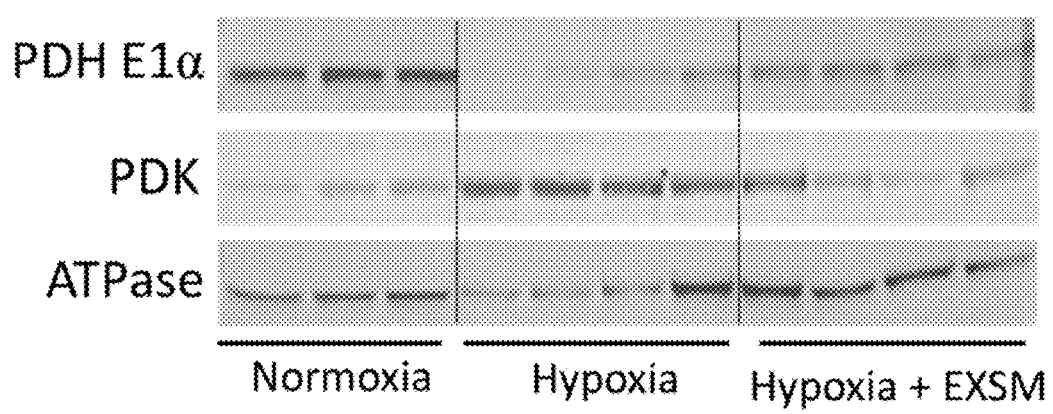

Smooth muscle cells (SMC) were treated with either PBS control or exosomes (EXSM) and incubated for 24 hours in either normoxia or hypoxia (4% $O_2$) conditions. RNA of SMC was isolated and sent to Qiagen for analysis using the global microarray platform. FIGS. 6A-6C shows that there is an increase in expression of genes in glucose metabolism after acute hypoxia exposure. EXSM treatment normalized this response in (a) glycolysis, (b) the TCA cycle and (c) the electron transport chain. These data suggest exosome treatment decreased or eliminated the need for genetic up-regulation of glucose oxidation genes during hypoxia stress, likely due to EXSM protein or gene incorporation into the pathways.

Example 1.7—Metabolomics Analysis of SMC Exposed to Acute Hypoxia

Smooth muscle cells (SMC) were treated with either PBS control or exosomes (EXSM) and incubated for 24 hours in either normoxia or hypoxia (4% $O_2$) conditions. Cell lysates were pelleted and sent to Metabolon (North Carolina) for global metabolite analysis. As shown in FIGS. 7A-7D, SMC lysates showed a build-up of metabolites in glycolysis, TCA cycle and energy metabolism pathways after acute hypoxia exposure, due to decreased flux through these pathways. Exosome treatment increased flux through (a) glycolysis and (b) the TCA cycle (represented by decreased metabolite build-up). These data indicates an increase in glucose oxidation. FIGS. 7A-7D show that acute hypoxia exposure resulted in a build-up adenosine and nicotinamide riboside, which are building blocks of ATP and NAD. Exosome treatment resulted in adenosine and nicotinamide riboside use, likely due to increased ATP production (c). ATP production was measured on live SMCs exposed to acute hypoxia (d), and confirmed an EXSM-mediated increase in ATP generation.

Example 1.8—Additional Methods

Mouse Model:
C57BL/6 mice were housed in hypoxia tents with oxygen levels controlled at 10% oxygen for three weeks to induce pulmonary hypertension. For exosomes treatment, a single-dose was injected into the tail vein 3 hours prior to hypoxia exposure.

Exosome Isolation and Analysis:
Serum-free conditioned media was collected from confluent MSC cultures over a 40 hour period. Conditioned media was concentrated 50× using tangential flow filtration. Concentrate was incubated with the fluorescent lipophilic dye, DiI, and then fractionated using an XK 50/100 column packed with Sepharose CL-2B resin (GE Heathcare). Exosome-containing fractions were identified by fluorescence detection of DiI and by phospholipid quantitation (Sigma). RNA sequencing on selected fractions was conducted by System Biosciences (CA). Proteomics on selected fractions was conducted by Bioproximity using LC-MS/MS (Chantilly, Va.). Pyruvate kinase protein and enzyme activity were assessed by ProteinSimple immunoassay and a colorimetric kinetic assay (Abcam, ab83432), respectively.

In Vitro Model:
Smooth muscle cells (SMC) were treated with PBS or exosomes for 24 hours in either normoxia or hypoxia (4% oxygen). Experimental replicates were processed for microarray analysis using the Illumina platform (Qiagen) or for metabolomics analysis using the HD4 platform (Metabolon, RTP, NC). Oxygen consumption was measured using the abcam extracellular 02 consumption assay kit (Abcam, ab197243).

Alveolar cells were seeded for 24 hours, and switched to 0.1% FBS media and primed with a potent population of exosome in normoxic incubator for 3 hours, and plated in hyperoxic incubation chamber for 48 hours (FIG. 17).

SMC chronic hypoxia model: SMC are known to switch to a proliferative, non-apoptotic phenotype in PAH and hypoxia, leads to thickening of the vessels and arteries in the lungs, causing higher pressures and ultimately damages to the heart/negative symptoms in PAH. SMCs were cultured at normoxia, hypoxia (4% oxygen), and hypoxia (4% oxygen) with exosomes. During the culturing period, the cells were being treated twice a week for two weeks with potent exosomes. The resulting SMCs were analyzed by microarray gene expression (IPA) and/or global metabolomics.

Example 1.9—In Vitro Treatment with Unexisomes

It has been demonstrated through in vitro experiments that unexisomes have immunomodulatory capacity. As shown in FIG. 18, unexisome treatment increased immunomodulatory capacity based on decreased IL-6 expression in cells exposed to hyperoxic stress (hyperoxia causes IL-6 release). As shown in FIG. 19, unexisome treatment increased immunomodulatory capacity based on reduced TNFα expression in cells exposed to hyperoxic stress (hyperoxia causes TNFα release).

It has also been demonstrated through in vitro experiments that unexisomes have anti-apoptosis capacity. As shown in FIG. 20, unexisome treatment exhibited anti-apoptosis effect under hyperoxia, as indicated by increased absorbance, corresponding to increased number of cells. As shown in FIG. 21, unexisome treatment reduced cytochrome C release from cells exposed to hyperoxic stress.

It has been further demonstrated through in vitro experiments that unexisomes can be used to promote pulmonary angiogenesis in BPD. As shown in FIG. 22A, unexisome treatment can restore tube formation in acute hyperoxia exposure conditions.

It has been additionally demonstrated through in vitro experiments that unexisomes can be used to improve mitochondrial metabolism in BPD-associated PAH. As shown in FIGS. 45A-45C, unexisomes upregulated amino acid metabolism in chronic hypoxia by global metabolite analysis of the intermediate metabolites within pathway. As shown in FIG. 48, unexisomes upregulated pyruvate and glutamate metabolism in chronic hypoxia.

As shown in FIG. 24, unexisomes upregulated GLUD1 gene expression in chronic hypoxia. As shown in FIG. 25, unexisomes downregulated PDK4 in chronic hypoxia. As shown in FIG. 26, unexisomes downregulated SIRT4 in chronic hypoxia. SIRT4 gene inhibits 2 metabolic enzymes, GLUD1 and PDH, in an in vitro PAH model. SIRT4 gene was downregulated by unexisome treatment in vitro PAH model, while GLUD1 and PDH were upregulated by exosome treatment. SIRT4 is believed to be a target for exosome treatment. As shown in FIG. 52, unexisomes restored TCA cycle function by upregulating the downregulated genes in hypoxia (6 out of 9 enzymes in the TCA cycle are downregulated).

Example 1.10—In Vivo Treatment with Unexisomes

Hyperoxia-Induced BPD Study:
C57BL/6 mice were subject to 75% oxygen from day 1 to day 7 postnatal (PN), and switched to room air with normal oxygen level from day 7 to day 14 postnatal. At PN4, a single-dose of potent exosomes was injected into the superficial temporal vain. At PN7 and PN14, RNA and histology analysis were conducted (FIG. 34).

BPD induced PAH study: C57BL/6 mice were subject to 75% oxygen from day 1 to day 7 postnatal (PN), and switched to room air with normal oxygen level from day 7 to day 42 postnatal. At PN4, a single-dose of potent exosomes was injected into the superficial temporal vain. At PN7 and PN14, RNA, histology and cytometric analysis were conducted. At PN42, histology and cytometric analysis were conducted, and additionally physiological measurements, lung function tests, and RV pressure measurements were also conducted (FIG. 34).

Combination treatment: C57BL/6 mice were subject to 10% oxygen from day 1 to day 29 and switched to normal condition from day 29 to day 56. On day 1, the mice were injected with semaxanib, and from day 29 to day 56, the mice were injected with sildenafil twice daily and with exosomes once every 3 days. RVSP level was measured (FIGS. 41A-41B).

As shown in FIGS. 36A-36B, unexisome treatment rescued BPD-associated alveolar simplification. FIG. 36A shows that treatment with potent exosomes rescues the hyperoxia (HYRX)-mediated increase in alveolar simplification compared to normoxia (NRMX). FIG. 36B shows quantification of mean liner intercept, which represents a surrogate of average air space diameter.

As shown in FIGS. 38A-38C, unexisome treatment rescued chronic alveolar simplification. FIG. 38A shows the images of cells under normoxia, hypoxia, and cells treated with Wharton's jelly derived exosomes, and bone marrow derived exosomes. FIG. 38B shows that exosomes rescued alveolar simplification in BPD-associated PAH mouse model. FIG. 38C shows that exosomes reduced modest lung fibrosis as shown by collagen deposition in the septal area in BPD-associated PAH mouse model.

As shown in FIGS. 39A-39D, unexisome treatment rescued PAH pulmonary vascular remodeling demonstrated by α-smooth muscle actin stain (FIG. 39A and FIG. 39B) and pressure changes associated with PAH (FIG. 39C). PV-loops demonstrate a significant shift in hyperoxia (HYRX) mice, indicative of emphysema-like features of lung disease and air trapping when compared to normoxia (NRMX) controls. Exosomes showed a significant rescue in this shift, indicative of improved lung function.

As shown in FIGS. 40A-40B, MSC exosomes prevented PAH in hypoxia-induced PAH mouse model. As shown in FIGS. 41A-41B, the combination therapy of exosome and sildenafil reversed PAH in Sugen/hypoxia-induced PAH mouse model. As shown in FIG. 42, exosomes upregulated amino acid metabolism in Sugen/hypoxia model of PAH.

Example 1.11—Characterization of Unexisomes

As shown in FIG. 28, isolation of the potent population of exosomes (COM2) using size exclusion chromatography result in significantly reduced contamination, compared to ultra-centrifugation or gradient separation which isolate not only exosomes of non-ideal size but also protein and non-potent microvesicles contaminants. As shown in FIG. 29, the isolated potent exosomes have more homogenous size and clearer image compared to ultracentrifuged samples.

As shown in FIG. 30, the isolated potent exosomes are free of MHCII contamination. In contrast, commercially available exosomes from ZenBio contain MHCII contamination.

As shown in FIGS. 31A-31B, the isolated potent exosomes isolated by size exclusion chromatograph are free of fibronectin and other protein contaminations based on ponceau staining, while ZenBio commercially available ultra-centrifuged preparation have fibronectin contamination.

As shown in FIG. 32, in RNAseq clustering analysis of the potent population and contaminant microvesicles, the potent exosomes (COM2) are differentially clustering from contaminating microvesicles, and are enriched in SORCS1, FHIT and ANKRD30BL. As shown in FIG. 33 the potent exosomes (COM2) have a lower CT value than COM1, corresponding to higher expression level of GAPDH expression.

Example 2.1—Introduction

Pulmonary arterial hypertension (PAH), a vascular remodeling disease of the lungs, results in increased pulmonary vascular resistance leading to right ventricular failure. Excessive proliferation and impaired apoptosis of pulmonary arterial smooth muscle cells (PASMCs) are thought to be key contributors to the remodeling associated with PAH. Despite the availability of therapies which improve the symptoms of PAH and major advances in the understanding of molecular mechanisms that underlie vascular remodeling, a cure for the disease has yet to be identified. Emerging evidence suggests that abnormalities exist in multiple organ systems (heart, skeletal muscle, spleen), all of which contribute to the pathogenesis of PAH. Therefore, current therapies focused on lung architecture may fail to treat all complexities of the disease. The finding that PAH is a metabolic disease could provide a unifying model to explain phenotypic similarities in diseased cells from multiple tissues.

Insulin resistance and glucose intolerance, secondary to mitochondrial dysfunction, have been shown to correlate with PAH pathogenesis. Similar to a cancerous phenotype, PAH-associated cells undergo a metabolic shift toward glycolysis and lactic acid fermentation which enables sustained ATP production and uncontrolled cellular growth. The resulting hyperproliferation and resistance to apoptosis complexes with aberrant mitochondrial function in the form of diminished glucose oxidation, anaplerosis into the TCA cycle and oxidative phosphorylation. Because these abnormalities are thought to precede disease progression in PAH, therapeutic targeting of mitochondrial dysregulation could provide an avenue into disease prevention or reversal. While several strategies for targeting the metabolic aspects of PAH have been proposed, a multifaceted approach may be required to combat the underlying metabolic cause(s) in addition to regeneration of lung microvasculature.

Stem cell therapy has emerged as a promising strategy for the treatment of PAH. However, stem cell transplants are often complicated by graft-versus-host concerns. Further studies determined that paracrine signaling in the form of exosomes could harness the benefits of stem cell therapy while avoiding transplantation-induced complications. Indeed, promising work has described an exosome-mediated reversal of the pulmonary arterial muscularization and right ventricular hypertrophy associated with PAH. Because emerging evidence suggests exosomes contain mitochondrial material, they could have a previously unidentified role in the promotion of mitochondrial function within the context of PAH.

Herein, whether mesenchymal stromal cell (MSC)-derived exosomes could improve the mitochondrial deficit in PAH was determined. To that end, the impact of exosomes on mitochondrial health was examined in PASMCs after a chronic hypoxia exposure and in a semaxinib/hypoxia rat model of PAH. The findings establish an important role for exosomes in increasing metabolic flux into the TCA cycle through regulation of the SIRT4 signaling pathways, thus improving mitochondrial function. These data suggest exosomes function to improve the underlying metabolic dysfunction associated with PAH.

Example 2.2—Methods

Preparation of Exosomes

Primary human bone marrow-derived mesenchymal stem cells (MSC; RoosterBio) were cultured as previously described [31]. In brief, MSCs were grown in KT-001 growth media (RoosterBio) until 100% confluent. Cells were then washed twice with PBS and incubated in serum-free, protein-free basal media for 48 hours. Conditioned media (CM) was collected, filtered (0.2 um filter), and adjusted to 10 mM EDTA and 25 mM HEPES. CM was concentrated by tangential flow filtration (Sartorius), and exosomes were purified using a size exclusion column packed with Sepharose CL-2B resin (GE Healthcare). In-line A280 wavelength data collection and choline-containing phospholipids such as lecithin, lysolecithin, and sphingomyelin (Phospholipid Assay Kit, Sigma) were measured and used to identify and pool the exosome-containing fractions.

Exosome Antibody Array

Exosomes were examined for known exosome markers flotillin-1 (FLOT1), intracellular adhesion molecule (ICAM), Alix, CD81, CD63, epithelial cell adhesion molecule (EpCAM), annexin A5 (ANXA5), and tumor susceptibility gene 101 (TSG101) using Exo-Check™ according to manufacturer's instructions (System Biosciences). Cis-golgi matrix protein 130 (GM130) was used as a control for cellular contamination. In brief, 300 μg exosome sample was lysed in RIPA and incubated overnight on the array. Arrays were then incubated in detection buffer for 2 hours at room temperature and imaged using SuperSignal West Femto Chemiluminescent Substrate (Thermofisher).

Proteomics and RNAseq on Exosome Samples

RNA sequencing was run at Geneviz using standard RNA-seq services Illumina HiSeq 2×150 bp analysis (Morrisville, N.C.). Data analysis was done using IPA software described below. Proteomics was conducted by Bioproximity using global proteomic profiling UPLC-MS/MS and up to 10,000 sequencing events (15 cm column, 20 min gradient; Chantilly, Va.). Protein FIG. 44D acronyms are defined as follows: GPI: Glucose-6-phosphate isomerase, ALDO: aldolase, TPI: triosephosphate isomerase, GAPDH: glyceraldehyde 3-phosphate dehydrogenase, ENO: enolase, PGAM: phosphoglycerate mutase, PK: pyruvate kinase, OGDH: oxoglutarate dehydrogenase, ETFA: electron-transfer-flavoprotein alpha, and ATPase: adenosine triphosphate synthase. Gene FIG. 44D acronyms are defined as follows: ALDOA: aldolase fructose-bysphosphate A, ENO3: enolase 3, GPI: glucose-6-phosphate isomerase, HK2: hexokinase 2, HK3: hexokinase 3, PFK: phosphofructokinase 1, PGM: pohsphoglucomutase 1, PK: pyruvate kinase, MDH2: malate dehydrogenase 2, OGDH: oxogluterate dehydrogenase, PC: pyruvate carboxylase, PDHA1: pyruvate dehydrogenase E1 alpha 1 subunit, PDHB: pyruvate dehydrogenase E1 beta subunit, SDHA: succinate dehydrogenase complex flavoprotein subunit A, SDHC: succinate dehydrogenase complex subunit C, SUCLG2: succinate-CoA ligase GDP-forming beta subunit, NDUFC2: NADH ubiquinone oxidoreductase subunit C2, NDUFB1: NADH ubiquinone oxidoreductase subunit B1, NDUFS5: NADH ubiquinone oxidoreductase subunit S5, NDUFA8: NADH ubiquinone oxidoreductase subunit A8, NDUFA9: NADH ubiquinone oxidoreductase subunit A9, NDUFS2: NADH ubiquinone oxidoreductase subunit S2, UQCRH1: ubiquinol-cytochrome c reductase hinge 1, COX6c1: cytochrome c oxidase subunit VIc, and COX10: heme A farnesyltransferase cytochrome c oxidase assembly factor.

In Vitro Chronic Hypoxia PASMC Culture

Primary human pulmonary arterial smooth muscle cells (PASMC; Lonza) were cultured in DMEM medium with 10% FBS (Thermofisher) under standard culture conditions. At confluence, cells were rinsed with PBS and incubated in DMEM+2% exosome-depleted FBS (SBI) with 10% well volume of PBS or EXSM treatment at 4% oxygen (i.e. 200 µl of EXSM+1.8 mL of PASMC culture media per well, in a 6-well plate format; approximately 2×10^7 exosomes per treatment). Cells were maintained in hypoxia for 2 weeks, treated biweekly on culture days 1, 4, 8, and 11. In EXSM dose response studies, PASMC were treated biweekly with 1.25%, 2.5%, 5%, and 10% well volume PBS or EXSM during hypoxic exposure (n=4-8 per group for all PASMC studies). Cells and media were collected and frozen at −80° C. for assays described below. PASMC supernatant was collected (n=8 per group) and citrate content was measured using a Citrate Assay Kit, (Abcam, ab83396) according to manufacturer's instructions. All PASMC were used between passages 1-3, and purchased commercially from Lonza. Four PASMC lots from different donors were used throughout these studies.

Metabolomics and Microarray Analysis

PASMC were cultured and treated with EXSM or PBS after normoxia or chronic hypoxia exposure as described above (n=3 for normoxia group, n=4 for hypoxia and hypoxia+EXSM groups). PASMC were pelleted, supernatant was aliquoted, and rat pulmonary arteries (PA) were ground in liquid nitrogen. PAMSC pellets, supernatant aliquots, and rat PA were processed at Qiagen using illumine microarray HumanHT-12 v4 Expression Beadchip Array for microarray gene analysis. Cell pellets and conditioned media were processed at Metabolon using the global metabolomics platform which utilizes ultra high-performance liquid chromatography/tandem accurate mass spectrometry (UHPLC/MS/MS) and an in-house mLIMS metabolite standard library for metabolomics profiling. Metabolomics data was analyzed using Metabolync software (Metabolon, Morrisville, N.C.). Metabolite figure acronyms are defined as follows—Gly: glycine, Ser: serine, Thr: threonine, Ala: alanine, Asp: aspartate, Glu: glutamic acid, His: histidine, Lys: lysine, Phe: phenylalanine, Tyr: tyrosine, Trp: tryptophan, Leu: leucine, Ile: isoleucine, Val: valine, Met: methionine, Cys: cysteine, Tau: taurine, Arg: arginine, Pro: proline, Cre: creatine, PA: polyamine, GSH: glutathione, and GAA: gamma-glutamyl amino acid.

IPA Analysis

Gene expression fold changes between treatment and control groups were analyzed through the use of IPA (QIAGEN Inc., qiagenbioinformatics.com/products/ingenuity-pathway-analysis). Briefly, an IPA core analysis using the HumanHT-12 v 4.0 reference set was performed to interpret data in the context of known (canonical) pathways and biological processes. Genes which were expressed below a log-2 fold change of 0.25 were removed from the analysis. To assess differential expression of specific targets (e.g. SIRT4, GLUD1) between treatment and control groups, custom pathways were created and connections to canonical pathways were made through use of the IPA knowledgebase.

PASMC Proliferation In Vitro Assay

PASMC proliferation was measured using WST-1 cell proliferation reagent (Abcam ab155902). PASMC were seeded at 2,000 cells/well in a 96-well plate in DMEM with 10% FBS (Thermofisher) under standard culture conditions for 24 hours. PASMC were rinsed with PBS and incubated in DMEM with 0.1% FBS to induce starvation conditions for 48 hours. Cells were then treated with 0.05%, 0.1%, 0.5%, 1%, 3%, 10%, or 30% well volume of EXSM treatment or PBS (n=4 per treatment), and FBS was added to 5% per well. Cells were incubated in normoxia or 4% oxygen for 4 days. 10 µL WST-1 was added per well and incubated for 3 hours. Plates were read at 440 nm using a FLUOstar Omega plate reader (BMG Labtech).

Western Blot Analysis

PASMC lysates were prepared using RIPA buffer (Thermofisher). Bolt LDS sample buffer and Bolt reducing reagent (both from Thermofisher) were added to each lysate and incubated at 70° C. for 10 minutes (n=4-8 per group). Approximately 20 mg of flash frozen rat gastrocnemius muscle was enriched for mitochondria using Cytochrome c Releasing Apoptosis Assay according to manufacturer instructions (Abcam, ab65311). Tissue was processed on ice using kit provided mitochondrial lysis buffers and a Tissue-Tearor 985370 (BioSpec Products, n=3 per group). Lysates were separated on 10% or 12% Bolt Bis-Tris Plus Gels (Thermofisher), and transferred to nitrocellulose membranes using iBlot 2 Gel Transfer Device (Thermofisher). Membranes were probed with primary antibodies rabbit monoclonal GLUD1 (1:1000, ab168352), mouse monoclonal PDH cocktail (bug/mL, ab110416), rabbit polyclonal PDK4 (1:50, ab71240), rabbit polyclonal TFAM (1:2000, ab131607), rabbit polyclonal COX4 (0.5 mg/ml, ab16056) and mouse monoclonal (3-actin (1:2000, ab8226; all antibodies from Abcam). Blot images were analyzed for band absorbance over background using GeneTools software (Syngene).

RNA Analysis

Total RNA was isolated using RNeasy Mini Kit (Qiagen) and cDNA was made using the High-Capacity cDNA Reverse Transcription Kit (Thermofisher) according to manufacturer instructions (n=4 per group). Taqman probes for SIRT4 (Hs01015516_g1) and PPIA (Hs04194521_s1) were assessed using a QuantStudio 6 Flex Real-Time PCR System (all from Thermofisher).

PASMC Oxygen Consumption Rate In Vitro

A Seahorse XFp Analyzer (Agilent) was used to measure oxygen consumption rate (OCR). PASMCs were seeded in XFp miniplates, treated with 5%, 15% or 30% well volume of PBS or EXSM and exposed to hypoxia (4% oxygen) for 24 hours (n=3 per group). The Cell MitoStress Test Assay was performed according to manufacturer instructions. In brief, after the three initial baseline OCR measurements, oligomycin (1 µM) was injected into all samples to inhibit ATP synthase (thereby blocking state 3 respiration). The remaining OCR is assumed proton leak. To determine the maximal OCR that cells can sustain, the proton ionophore (uncoupler) FCCP (4 µM) was injected. Lastly, a mix of rotenone and antimycin A (0.5 uM) was injected to inhibit electron flux through Complex III. Remaining OCR is due to the formation of mitochondrial ROS and non-mitochondrial sources. OCR values were normalized to total protein measurements per well using a BCA Assay kit (Thermofisher). All negative OCR values were reported as zero in analyzed data.

Rat Model of Semaxinib/Hypoxia-Induced PAH

All in vivo experiments approved by the Institutional Animal Care and Use Committee and were carried out by CorDynamics as previously described. In brief, randomized adult (200-300 g) male Sprague-Dawley rats (65 total; n=5 for normoxia control group, n=10 for all other groups) were administered a single subcutaneous dose of semaxanib (20 mg/kg) on day 1 of the study and maintained in chronic hypoxia (~13% oxygen) or normoxia for 28 days. All hypoxic groups were removed from hypoxia on day 29 and placed in normoxic conditions for treatment until day 56. Control and treatment groups were dosed with a single intravenous EXSM or PBS injection at the tail every 3 days from day 29 to day 53 (250 µL, approximately 2.5×10^7 exosomes per injection). All animals were allowed food and tab water ad libitum. On terminal day 56, rats were anesthetized by and intraperitoneal injection of ketamine/xylazine (80/10 mg/kg), a millar pressure catheter was introduced into the carotid artery to measure heart rate (HR), and a fluid-filled pressure catheter was introduced into the right jugular vein to measure pulmonary artery pressure (SPAP). After rats were euthanized, the heart was removed, infused with saline until clear, and ventricles were weighed separately (RV, RV/LV+S). Pulmonary arteries and gastrocnemius skeletal muscle were removed and frozen at −80° C. for metabolomics and protein analysis, respectively. Studies performed and unbiased data compiled by CorDynamics.

Mouse Model of Hypoxia-Induced PAH

All in vivo experiments approved by the Institutional Animal Care and Use Committee and were carried out by CorDynamics as previously described. On study day 1, randomized naïve male C57BL/6 mice were administered a single intravenous dose of EXSM or PBS (lateral tail vein injection, 200 uL, approximately 2×10^7 exosomes per treatment) prior to hypoxic exposure. On study day 2, normoxic mice (n=7) were maintained in ambient conditions, while hypoxic mice (n=8) were maintained in 10% oxygen for 21 days. All animals were allowed food and tab water ad libitum. On terminal day 22, mice were euthanized and a Millar pressure catheter was introduced through the right jugular vein to measure right ventricular systolic pressure (RVSP). The heart was removed and the right ventricle (RV) and left ventricle with septum (LV+S) were weighed separately. Studies performed and unbiased data compiled by CorDynamics.

Nanoparticle Tracking Analysis

Exosome particle analysis was outsourced to Particle Technology Group LLC nanoparticle tracking analysis services. Exosome concentration and size was measured using a Nanosight NS300 (Malvern) according to manufacturer instructions.

Transmission Electron Microscopy (TEM)

Exosome TEM imaging was outsourced to the University of North Carolina at Chapel Hill Microscopy Services Laboratory (MSL) in the Pathology and Laboratory Medicine Department. Exosomes were prepared by negative staining with 2% sodium phosphotungstate, pH 7.0 (PTA). Grids were floated on 15 µl droplets of exosome suspension and incubated for 20 minutes, transferred to a 25 µl droplet of 1% glutaraldehyde in 0.15M sodium phosphate buffer, pH 7.4 and fixed for 5 minutes. After a brief rinse on 2 sequential droplets of deionized water, the grids were transferred to a 25 µl droplet of 2% PTA and stained for 1 minute. Samples were observed with a JEOL JEM-1230 transmission electron microscope operating at 80 kV (JEOL USA, Peabody, Mass.) and digital images acquired using a Gatan Orius SC1000 CCD camera and Gatan Microscopy Suite 3.0 software (Gatan, Inc., Pleasanton, Calif.).

Statistical Analysis

All values are expressed as mean±standard error and analyzed using an unpaired, two-tailed student's t-test. All comparisons between experimental groups were performed using a one-way ANOVA with Tukey's multiple comparisons test using GraphPad PRISM 7.3 statistical software unless otherwise indicated.

Example 2.3—Results and Analysis

Bone Marrow MSC-Derived Exosomes are Enriched in Metabolic Proteins and Genes

To characterize bone marrow mesenchymal stromal cells (MSC) secreted exosomes, exosome protein, vesicle size, and metabolic protein and gene content were evaluated. Isolated exosomes expressed FLOT1, ICAM, ALIX, CD81, CD63, EpCAM, ANXA5, and TSG101 (exosome-specific proteins), and were devoid of GM130, a Golgi apparatus protein (cellular contamination; FIG. 44A). TEM imaging and nanoparticle tracking analysis demonstrated exosomes range between 50-150 nm in size and have an average concentration of 1×10^8 particles/mL (FIG. 44B and FIG. 44C). Proteomics and RNA sequencing analysis revealed exosomes are enriched with metabolic protein and gene content (FIG. 44D).

Exosomes Improve Amino Acid Metabolism in Hypoxia

Metabolic dysfunction consistent with the Warburg effect contributes to the pathogenesis of PAH. Pulmonary arterial smooth muscle cells (PASMC) cultured in hypoxia are often used as an in vitro tool to study the metabolic changes associated with PAH. Thus, a global metabolite analysis of human PASMC cultured in chronic hypoxia with exosome treatment was conducted to explore the effect of exosomes on metabolic dysfunction in PAH. These data revealed a decrease in amino acids (AA) after hypoxia exposure compared to normoxia control (FIG. 45A, left column), demonstrating a decline in global AA metabolism. Inversely, exosome treatment increased AA levels compared to hypoxia alone (FIG. 459A, right column). These data are indicative of an exosome-mediated boost in AA metabolism during chronic hypoxia exposure.

Further assessed are metabolite uptake and production via analysis of PASMC cell culture supernatant. Of the metabolites present in the supernatant, cysteine, glycine, serine, threonine, arginine, histidine, and glutamic acid were present in the cell culture growth media while alanine and proline were not. Hypoxic supernatant contained less alanine and proline than normoxic supernatant, reflecting a decrease in production. Exosome treatment increased these metabolites compared to hypoxic supernatant alone (FIG. 45B, top heat map). Importantly, the opposite was found in metabolite uptake of PASMC. AA contained in the culture media were found in higher levels in hypoxic supernatant compared to normoxic supernatant, suggesting a decline in AA uptake or cellular production, likely due to their diminished metabolism. Exosome treatment decreased levels of these metabolites, indicative of increased metabolite consumption compared to hypoxia alone (FIG. 45B, bottom heat map). These data demonstrate that chronic hypoxia suppresses both uptake and production of amino acids while exosome pre-treatment reinstates amino acid metabolism.

Exosomes Increase Glucose Oxidation and Prevent a Shift to Glycolysis, Mitochondrial Damage, and Increased Proliferation in Chronically Hypoxic PASMC A dysfunction in amino acid consumption could suggest a decrease in oxidative metabolism and thus a metabolic shift toward glycolysis. In support of this, PASMC are known to undergo a glycolytic shift after hypoxia exposure and in animal models of PAH. Herein, lactate levels were dramatically increased in the hypoxic supernatant compared to normoxia, consistent with increased rates of glycolysis.

Importantly, exosome treatment decreased lactate and glucose levels in the supernatant compared to hypoxia alone (FIG. 45C) reflecting increased glucose uptake and decreased lactate production. These data indicate increased flux into oxidative metabolism.

To further understand the exosome effects on glucose oxidation, TCA cycle metabolites in PASMC supernatant were assessed. While chronic hypoxia decreased TCA metabolites, exosome pre-treatment normalized these levels (FIG. 45D). The first metabolite within the TCA cycle, citrate, followed the same trend when measured independently. Citrate levels were decreased after hypoxic exposure and normalized with exosome treatment (FIG. 45E). These data demonstrate a decrease in TCA cycle metabolites after hypoxia exposure, an effect that was mitigated with exosome treatment.

In order to determine the functional impact of exosome treatment on oxidative phosphorylation, oxygen consumption rate (OCR) was measured in PASMC after acute (24 hr) hypoxia exposure. Exosome pre-treatment dramatically increased OCR of hypoxic PASMC in a dose-dependent manner, increasing OCR up to 15-fold over hypoxia control with exosome treatment (FIG. 45F). These data directly demonstrate a beneficial effect of exosomes on mitochondrial function in hypoxia. Because increased oxygen consumption indicates increased energy production in the cell, various building blocks of energy sources were assessed—creatine, phosphocreatine, nicotinamide, nicotinamide ribonucleotide, and adenosine. Acute hypoxia exposure decreased creatine, phosphocreatine, and nicotinamide ribonucleotide compared to normoxia, while exosome treatment increased these metabolites compared to hypoxia alone (FIG. 45G). The hypoxia-induced decrease in these energy precursors indicates a decrease in energy production through the creatine, NAD, and ATP pathways, which was curbed with exosome treatment. These data demonstrate that hypoxia exposure decreased oxygen consumption and energy production in PASMC, both of which were prevented by exosome treatment.

Because decreased TCA cycle metabolism and oxygen consumption are indicative of mitochondrial dysfunction, PASMCs were evaluated for genes associated with mitochondrial damage. Hypoxia exposure increased levels of heat shock protein 90 (HSP90), tumor necrosis factor alpha (TNF), and fas ligand TNF superfamily member 6 (FASLG), reflective of the mitochondrial damage seen in PAH (FIG. 45H). Inversely, cytochrome c oxidase subunit 4 (COX4), LIM homeobox transcription factor 1 beta (LMX1B), and tumor protein P53 (TP53), indicators of healthy mitochondrial function, were decreased after hypoxia exposure similar to PAH pathogenesis (FIG. 45H). Importantly, this gene expression profile was reversed by exosome treatment, suggesting exosomes prevent the mitochondrial damage associated with chronic hypoxia (FIG. 45H, right panel). Lastly, PASMC hyper-proliferation is a trademark characteristic of PAH pathogenesis and decreased mitochondrial function. Thus, PASMC hyper-proliferation in hypoxia after exosome exposure was assessed. While hypoxic exposure increased PASMC proliferation in vitro, exosome treatment decreased proliferation in a dose responsive manner (FIG. 45I).

Exosome Treatment Improves PAH Pathogenesis in a Rat Model

The translational relevance of these findings was evaluated in a semaxinib/hypoxia rat model of PAH. Exposure of rats to semaxinib/hypoxia resulted in a 4.5-fold increase in systolic pulmonary arterial pressure (SPAP) compared to control rats. In contrast, exosome treatment reduced SPAP compared to disease control (FIG. 46A). Additionally, semaxinib/hypoxia rats had decreased heart rate (HR), increased right ventricular weight (RV), and increased right ventricular to left ventricular and septum weight ratio (RV/LV+S) representative of the decreased cardiac output and vascular remodeling in PAH. Importantly, exosome treatment partially reversed this disease phenotype (FIGS. 46B, 46C and 46D). These data indicate exosome treatment reverses PAH pathogenesis.

Exosome Treatment Increases Mitochondrial Metabolism in a Rat Model of PAH

Because derangements in mitochondrial function are known to exist in PAH, the potential impact of exosome therapy on PAH-induced metabolic dysfunction was investigated. Metabolomics analysis of rat pulmonary arteries (PA) revealed decreased levels of TCA cycle metabolites in disease compared to control, while exosome treatment demonstrated an increase in these metabolites (FIG. 47A). Correlation analysis of SPAP and TCA cycle metabolites demonstrated a negative correlation, indicating rats with improved SPAP had elevated TCA cycle intermediates (FIG. 47B). These data mirror PASMC metabolomics data (FIGS. 45A-45I), demonstrating that exosome treatment increased flux through the TCA cycle both in vitro and in vivo.

Decreased TCA cycle function and subsequent dependence on glycolysis are known to result in the accumulation of fructose and sorbitol in PAH. Metabolomics data indicated a greater than 2-fold increase in fructose and sorbitol levels in the PA of disease rats compared to control, which was normalized with exosome treatment (FIG. 47C). Further, a positive correlation was seen between SPAP and both fructose and sorbitol, demonstrating that rats with improved SPAP had diminished levels of fructose and sorbitol (FIG. 47D). These findings complement PASMC in vitro data demonstrating that exosome treatment increases glucose flux through glucose oxidation and away from glycolysis (FIGS. 45A-45I). Additionally, redox couples such as glutathione/reduced glutathione (GSH/GSSG) and cysteine/cystine (Cys/CySS) are widely used as indicators of mitochondrial and extracellular oxidative stress in various disease models. Herein, GSH/GSSG and Cys/CySS ratios were decreased in PAH compared to control, while exosome treatment increased both ratios after hypoxia exposure (FIG. 47E). These data indicate that exosome treatment decreased oxidative stress in PAH.

Lastly, because mitochondrial dysfunction occurs in multiple organ systems in patients with PAH, the effect of exosomes on skeletal muscle mitochondrial transcription factor A (TFAM) was evaluated. Gastrocnemius muscle lysates enriched for mitochondria had diminished TFAM expression in semaxinib/hypoxia rats compared to control, while exosome treatment normalized these protein levels (FIG. 47F). These results indicate exosome treatment improves global mitochondrial health and integrity in PAH.

Exosomes Upregulate Pyruvate Dehydrogenase (PDH) and Glutamate Dehydrogenase (GLUD1) in Hypoxia In order to identify the mechanism by which exosomes improve TCA cycle metabolism in hypoxia and PAH, PASMC amino acids were mapped to their appropriate entry points into the TCA cycle. These data revealed a pattern wherein exosome treatment impacted specific entry points, namely the pyruvate and glutamine pathways. Hypoxic exposure decreased AA entering the TCA cycle through all entry points—acetyl-CoA, a-ketoglutarate, succinyl-CoA, fumarate, and oxaloacetate compared to normoxia (FIG. 48, left bars). Exosome treatment increased AA entering the TCA cycle through acetyl-CoA via pyruvate dehydrogenase (PDH) and a-ketoglutarate thru glutamate dehydrogenase (GLUD1) only (FIG. 48, right bars), demonstrating exosome treatment increased flux into the TCA cycle through targeting these pathways.

To further explore exosome therapeutic targeting of PDH and GLUD1, microarray gene expression analysis of PASMC in chronic hypoxia was performed. Both PDH and GLUD1 mRNA, known to be inhibited by HIF1-a signaling in hypoxia, are reduced in PAH. In support of these previous reports, microarray analysis indicated PDH and GLUD1 were downregulated in hypoxia compared to normoxia (FIGS. 49A and 49B, left panel), a phenotype which was prevented with exosome treatment (FIGS. 49A and 49B, right panel). Further, pyruvate dehydrogenase kinase (PDK4), an inhibitor of PDH which is upregulated in PAH patients, was elevated in hypoxia. This increase in gene expression was prevented by exosome treatment (FIG. 49B). Consistent with the metabolite data, these gene expression trends imply decreased flux into the TCA cycle after hypoxic exposure. Exosomes prevented this through upregulation of the PDH and GLUD1 pathways.

Since exosome treatment upregulates both PDH and GLUD1 gene expression in hypoxia, it was determined if protein levels were likewise regulated. To this end, PDH, GLUD1, and PDK4 protein expression was assessed in hypoxic PASMC. Hypoxic exposure decreased PDH and GLUD1 but increased PDK4 protein expression compared to normoxia while exosome treatment prevented these changes, maintaining high levels of PDH and GLUD1 and low levels of PDK4 protein (FIGS. 50A, 50B and 50C). Further, increasing doses of exosome treatment resulted in a dose responsive increase in PDH and GLUD1 and a decrease in PDK4 protein expression (FIGS. 50D, 50E and 50F). In complex, these data demonstrate exosome upregulation of PDH and GLUD1 pathways at both the gene and protein levels in prolonged hypoxia.

SIRT4: Exosome Treatment Targets Upstream Regulator of PDH and GLUD1

Sirtuin 4 (SIRT4) has been shown to inhibit both PDH and GLUD1 activity and metabolism through separate processes, though little is known about its activity in hypoxia. It is believed that (1) hypoxic exposure activates SIRT4 to serve as an energy-sparing safeguard in response to hypoxic stress and (2) exosome treatment inhibits SIRT4, removing the blockage and upregulating both PDH and GLUD1 pathways. In support of this, microarray gene expression revealed SIRT4 to be upregulated after chronic hypoxia and downregulated with exosome treatment compared to hypoxia control (FIG. 51A). These data indicate a hypoxia-induced upregulation of SIRT4 which could inhibit GLUD1 and PDH. Exosome treatment removes this SIRT4 blockage, restoring GLUD1 and PDH pathways.

Moreover, SIRT4 gene expression in PASMC with increasing time in hypoxia was assessed. Quantitative-RT-PCR showed SIRT4 gene expression increased over time in hypoxia-exposed PASMCs compared to normoxic control. Exosome pre-treatment downregulated SIRT4 gene expression after 7 and 14 days in hypoxia compared to hypoxic control alone (FIG. 51B). These data indicate SIRT4 upregulation is driven by sustained hypoxic exposure, while exosome treatment prevents this change. Additionally, increasing doses of exosomes decreased SIRT4 gene expression (FIG. 51C), supporting the notion that exosomes downregulate SIRT4 gene expression in hypoxia even at low doses. These data support that SIRT4, upstream of PDH and GLUD1, functions to reduce nutrient flux into the mitochondria under conditions of hypoxic stress. Exosomes may function to release this block by inhibiting SIRT4 and reestablishing flux through the TCA cycle and mitochondrial metabolism.

Role of Exosomes in Mitochondrial Metabolism in PAH

The data herein indicate that in hypoxic PASMC, SIRT4 is activated as an energy sparing safeguard to allow cells to survive under hypoxic stress. SIRT4, upstream regulator of mitochondrial PDH and GLUD1, decreases pyruvate and glutamine entry into the TCA cycle by inhibiting these enzymatic entry points. Decreased PDH activity is further exacerbated by the activation of known inhibitor, PDK4. This blockage results in an overall reduction of mitochondrial function (FIG. 52, left panel). Exosome treatment inhibits SIRT4 and PDK4, potentially removing the blockage on PDH and GLUD1 and restoring glutamine and pyruvate flux into the TCA cycle, thereby reestablishing mitochondrial function (FIG. 52, right panel).

Additional Analysis

The current example examined the potential role of exosome therapy in pulmonary arterial hypertension (PAH)-associated mitochondrial dysfunction. While a glycolytic shift occurs in PAH, data herein demonstrate that exosomes promote flux into the tricarboxylic acid (TCA) cycle, resulting in elevated oxidative phosphorylation. Evidence has been provided that exosomes promote anaplerosis through expression of pyruvate dehydrogenase (PDH) and glutamate dehydrogenase (GLUD1). Further, it was demonstrated that exosomes inhibit sirtuin 4 (SIRT4) expression, and suggest that curbing SIRT4, upstream of PDH and GLUD1, contributes to the exosome-mediated improvement in mitochondrial function. Taken together, the results indicate that exosome treatment improves mitochondrial function by jumpstarting the TCA cycle through provision of nutrients.

Pulmonary arterial hypertension is associated with decreased mitochondrial function, an underlying perturbation contributing to disease. Commonly, animal models use prolonged hypoxia to induce remodeling of the vascular smooth muscle, leading to chronic vasoconstriction and hyperplasia of vascular smooth muscle cells, as seen in PAH. Importantly, this hypoxia exposure results in mitochondrial perturbations consistent with those seen in PAH patients. In an effort to capture this phenotype in vitro, human pulmonary arterial smooth muscle cells (PASMC) were exposed to low oxygen for two weeks. Consistent with PAH patients, the prolonged hypoxia regimen resulted in hyper-proliferation of PASMCs (data not shown), elevated lactate production and decreased metabolite entry into the TCA cycle (FIGS. 45A-45I). These data support the use of chronic hypoxia as a model of PAH-associated mitochondrial dysfunction. Importantly, exosome treatment rescued the effects of hypoxia exposure, decreasing lactate production and increasing TCA cycle metabolites. Further, providing definitive evidence of rescued mitochondrial function, exosome treatment increased oxygen consumption after hypoxia exposure in a dose-dependent manner, (FIG. 45F). These data were confirmed using a semaxinib/hypoxia rat model of PAH. Exosomes increased TCA cycle metabolites and decreased polyol pathway metabolites in semaxinib/hypoxia tissue, indicative of an elevation in oxidative phosphorylation (FIGS. 47A-47F).

The concept of extracellular vesicles containing mitochondrial components, such as mitochondrial proteins and mRNA, is not new. In fact, intracellular mitochondrial transfer has been shown by multiple groups. In these studies, vesicles have been suggested to participate in horizontal transfer of intact mitochondria, leading to improvements in mitochondrial function. However, herein exosomes generated from bone marrow MSC are not able to consume oxygen, indicating the lack of an intact electron transport chain. Additionally, the use of size exclusion chromatography to isolate exosomes herein result in particles in the 50-200 nm size range (FIGS. 44A-44D) while intact mitochondria range from 0.5-10 μm. Therefore, the potential transfer of intact mitochondria is unlikely to cause the observed improvements in mitochondrial dysfunction. It has been shown that exosomes contain mitochondrial proteins, mtDNA, and mitochondrial genes (FIGS. 44A-44D). It is believed that the transfer of this mitochondrial protein and genetic material functions to boost mitochondrial function via host cell remodeling. The mechanism by which exosomes improve oxidative phosphorylation was determined.

Mapping of metabolite entry into the TCA cycle resulted in a clear exosome-mediated induction of two distinct entry points, glutamate and pyruvate (FIG. 48). These data indicate regulation of key enzymes within these pathways. Glutamate dehydrogenase (GLUD1) converts glutamate to the TCA cycle metabolite, α-ketoglutarate. Shown to be inhibited in severe hypoxia and an in vitro model of PAH, a decrease in GLUD1 activity is consistent with the decline in TCA cycle function in PAH. Here it was shown that chronic hypoxia results in a deficit in GLUD1 both at the gene and protein levels (FIGS. 49A-49B, 50A-50F). Exosome exposure rescued mRNA and protein expression of GLUD1 in parallel with heightened TCA cycle metabolites, indicative of increased nutrient flow into the TCA cycle.

Pyruvate dehydrogenase (PDH) converts pyruvate into acetylCoA, linking glycolysis to the TCA cycle. PDH consists of four enzymatic components: pyruvate dehydrogenase (E1), dihydrolipoamide acetyltransferase (E2), lipoamide dehydrogenase (E3) and E3-binding protein (BP) which are highly regulated. Composed of a heterotetramer of two alpha and two beta subunits, the E1α site is specifically inhibited through phosphorylation by pyruvate dehydrogenase kinase 4 (PDK4). Importantly, elevations in PDK4 protein and diminished PDH activity are common in PAH patients. In agreement with previous studies, a hypoxia-mediated increase in PDK4 gene and protein levels and subsequent decline in PDH were shown consistent with PAH. Interestingly, exosomes induce pyruvate dehydrogenase (PDH) gene expression through E1 subunit β and via inhibition of pyruvate dehydrogenase kinase (PDK; FIGS. 49A-49B). These data suggest the potential of exosomes to modulate both subunits in the E1 enzyme (E1α through inhibition of PDK4 and E1β through direct induction of gene expression). Redundant activation in this way may be needed to fully improve flux through the PDH complex. Beyond increases in PDH gene regulation, FIGS. 50A-50F demonstrates a dose-responsive regulation of PDH and PDK4 proteins, highly indicative of an exosome-mediated restoration of PDH in the context of mitochondrial dysfunction.

Increased flux through GLUD1 and PDH might be sufficient to increase mitochondrial function. This is supported by experiments examining dichloroacetate (DCA), a PDK inhibitor, as a potential therapeutic for metabolic dysfunction in PAH. DCA studies propose increased PDH activity alone could benefit PAH patients. Herein, the increase in flux through both PDH and GLUD1 make exosomes an exciting therapeutic strategy for combating the metabolic dysfunction associated with PAH. Exosomes have proven effective in treating other aspects of the disease, including peripheral pulmonary arteriolar remodeling and lung inflammation. Therefore, exosomes provide a multi-faceted treatment for pulmonary arterial hypertension, improving vascular remodeling and the underlying metabolic disorder in disease.

Lastly, results herein describe the involvement of sirtuin 4 (SIRT4) in the pathogenesis of PAH. SIRT4 is known to function as an ADP-ribosyltransferase. Previous studies have shown that genetic inhibition of SIRT4 increased oxygen consumption. Further, SIRT4 prevented hypoxia-induced apoptosis after acute hypoxia exposure. Given that SIRT4 has been shown to inhibit GLUD1 and PDH, SIRT4 may protect against hypoxia-induced cell death by reducing metabolite entry into the TCA cycle via these two nutrient entry points. However, SIRT4 may become chronically activated after prolonged hypoxia, contributing to mitochondrial dysfunction. In support of this, an increase in SIRT4 gene expression with increased hypoxia exposure (FIG. 51A) was demonstrated. Exosome treatment reduced SIRT4 gene expression, even at low treatment volume (FIG. 51B), indicating that exosomes could mediate SIRT4 regulation.

The invention claimed is:

1. A method of treating pulmonary hypertension, comprising administering to a subject in need thereof isolated extracellular vesicles or exosomes obtained from mesenchymal stromal cells, wherein the isolated extracellular vesicles or exosomes are selected to have increased expression of one or more expression products of genes in the glycolysis pathway as compared to the average amount of the expression products in all extracellular vesicles or exosomes obtained from the mesenchymal stromal cells.

2. The method of claim 1, wherein the extracellular vesicles or exosomes comprise at least 20% more expression of the expression products compared to the average amount of the same expression product in all extracellular vesicles or exosomes obtained from the mesenchymal stromal cells.

3. The method of claim 1, wherein the expression product of genes in the glycolysis pathway is selected from the group consisting of pyruvate kinase (PK), AGI, aldolase (ALDO), aldolase fructose-bysphosphate A (ALDOA), enolase 3 (ENO3), glucose-6-phosphate isomerase (GPI), hexokinase 2 (HK2), hexokinase 3 (HK3), phosphofructokinase 1 (PFK), phosphoglucomutase 1 (PGM), triosephosphate isomerase (TPI), glyceraldehyde 3-phosphate dehydrogenase (GAPDH), enolase (ENO), and phosphoglycerate mutase (PGAM).

4. The method of claim 3, wherein the expression product is pyruvate kinase (PK).

5. The method of claim 1, wherein the isolated extracellular vesicles or exosomes normalize glucose oxidation in lung tissue of the subject.

6. The method of claim 1, wherein the isolated extracellular vesicles or exosomes have a pyruvate kinase (PK) activity of at least 0.15 nmol/min/mL.

7. The method of claim 1, wherein the isolated extracellular vesicles or exosomes are capable of increasing O2 consumption by smooth muscle cell (SMC) lysates subjected to a 24-hour hypoxia exposure by at least 20% compared to control SMC cell lysates subjected to a 24-hour hypoxia exposure and treated with PBS control.

8. The method of claim 1, wherein the isolated extracellular vesicles or exosomes express one or more of flotillin-1 (FLOT1), intracellular adhesion molecule (ICAM), ALIX, CD81, CD63, epithelial cell adhesion molecule (EpCAM), annexin A5 (ANXA5), and tumor susceptibility gene 101 (TSG101), and/or wherein the isolated extracellular vesicles or exosomes do not express Cis-golgi matrix protein 130 (GM130).

9. The method of claim 1, wherein the isolated extracellular vesicles or exosomes upregulate glutamate dehydrogenase (GLUD1) and/or pyruvate dehydrogenase (PDH) gene expression in the subject, downregulate pyruvate dehydrogenase kinase 4 (PDK4) gene expression in the subject, and/or downregulate sirtuin4 (SIRT4) gene expression in the subject.

10. The method of claim 1, wherein:
(a) the subject suffers from increased expression of HSP90 associated with mitochondria damage, and the isolated extracellular vesicles or exosomes downregulate the expression of HSP90;
(b) the subject suffers from increased expression of tumor necrosis factor (TNF) associated with mitochondria damage, and the isolated extracellular vesicles or exosomes downregulate the expression of TNF;
(c) the subject suffers from increased expression of fas ligand TNF superfamily member 6 (FASLG) associated with mitochondria damage, and the isolated extracellular vesicles or exosomes downregulate the expression of FASLG;
(d) the subject suffers from decreased expression of cytochrome c oxidase subunit 4 (COX4) associated with mitochondria damage, and the isolated extracellular vesicles or exosomes upregulate the expression of COX4;
(e) the subject suffers from decreased expression of LIM homeobox transcription factor 1 beta (LMX1B) associated with mitochondria damage, and the isolated extracellular vesicles or exosomes upregulate the expression of LMX1B; and
(f) the subject suffers from decreased expression of tumor protein P53 (TP53) associated with mitochondria damage, and the isolated extracellular vesicles or exosomes upregulate the expression of TP53.

11. The method of claim 1, wherein the subject suffers from increased proliferation of pulmonary arterial smooth muscle cells (PASMC), and the isolated extracellular vesicles or exosomes decrease the proliferation of PASMC.

12. The method of claim 1, wherein:
(a) the subject suffers from increased right ventricular weight associated with pulmonary arterial hypertension (PAH), and the isolated extracellular vesicles or exosomes decrease the right ventricular weight of the subject;
(b) the subject suffers from increased right ventricular to left ventricular and septum weight ratio associated with PAH, and the isolated extracellular vesicles or exosomes decrease the right ventricular to left ventricular and septum weight ratio of the subject;
(c) the subject suffers from increased heart rate associated with PAH, and the isolated extracellular vesicles or exosomes decrease the heart rate of the subject; and
(d) the subject suffers from decreased cardiac output associated with PAH, and the isolated extracellular vesicles or exosomes increase the cardiac output of the subject.

13. The method of claim 1, wherein the subject suffers from decreased expression of mitochondrial transcription factor A (TFAM) associated with mitochondria damage, and wherein the isolated extracellular vesicles or exosomes upregulate the expression of TFAM.

14. The method of claim 1, further comprising administering sildenafil to the subject.

15. The method of claim 1, wherein the isolated extracellular vesicles or exosomes are capable of reducing Right Ventricular Systolic Pressure (RVSP) of mice subjected to a three-week chronic hypoxia exposure by at least 10% compared to control mice subjected to a three-week chronic hypoxia exposure and treated with PBS.

16. The method of claim 15, wherein the isolated extracellular vesicles or exosomes express one or more of flotillin-1 (FLOT1), intracellular adhesion molecule (ICAM), ALIX, CD81, CD63, epithelial cell adhesion molecule (EpCAM), annexin A5 (ANXA5), and tumor susceptibility gene 101 (TSG101), and/or wherein the isolated extracellular vesicles or exosomes do not express Cis-golgi matrix protein 130 (GM130).

17. The method of claim 15, wherein the isolated extracellular vesicles or exosomes upregulate glutamate dehydrogenase (GLUD1) and/or pyruvate dehydrogenase (PDH) gene expression in the subject, downregulate pyruvate dehydrogenase kinase 4 (PDK4) gene expression in the subject, and/or downregulate sirtuin4 (SIRT4) gene expression in the subject.

18. The method of claim 15, wherein:
(a) the subject suffers from increased expression of HSP90 associated with mitochondria damage, and the isolated extracellular vesicles or exosomes downregulate the expression of HSP90;
(b) the subject suffers from increased expression of tumor necrosis factor (TNF) associated with mitochondria damage, and the isolated extracellular vesicles or exosomes downregulate the expression of TNF;
(c) the subject suffers from increased expression of fas ligand TNF superfamily member 6 (FASLG) associated with mitochondria damage, and the isolated extracellular vesicles or exosomes downregulate the expression of FASLG;
(d) the subject suffers from decreased expression of cytochrome c oxidase subunit 4 (COX4) associated with mitochondria damage, and the isolated extracellular vesicles or exosomes upregulate the expression of COX4;
(e) the subject suffers from decreased expression of LIM homeobox transcription factor 1 beta (LMX1B) associated with mitochondria damage, and the isolated extracellular vesicles or exosomes upregulate the expression of LMX1B; and
(f) the subject suffers from decreased expression of tumor protein P53 (TP53) associated with mitochondria damage, and the isolated extracellular vesicles or exosomes upregulate the expression of TP53.

19. The method of claim 15, wherein the subject suffers from decreased expression of mitochondrial transcription factor A (TFAM) associated with mitochondria damage, and wherein the isolated extracellular vesicles or exosomes upregulate the expression of TFAM.

20. The method of claim 15, further comprising administering sildenafil to the subject.

* * * * *